(12) United States Patent
Nicholson

(10) Patent No.: US 11,697,003 B2
(45) Date of Patent: *Jul. 11, 2023

(54) VASCULATURE NAVIGATION SYSTEMS AND METHODS

(71) Applicant: Andrew Nicholson, Knoxville, TN (US)

(72) Inventor: Andrew Nicholson, Knoxville, TN (US)

(73) Assignee: TICI 3 Therapeutics, Inc., Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/401,996

(22) Filed: Aug. 13, 2021

(65) Prior Publication Data

US 2022/0168549 A1   Jun. 2, 2022

Related U.S. Application Data

(63) Continuation-in-part of application No. 17/107,791, filed on Nov. 30, 2020, now Pat. No. 11,090,466.

(51) Int. Cl.
  *A61M 25/00* (2006.01)
  *A61M 25/09* (2006.01)
  *A61M 39/06* (2006.01)

(52) U.S. Cl.
  CPC ............ *A61M 25/09* (2013.01); *A61M 39/06* (2013.01); *A61M 2025/0046* (2013.01); *A61M 2039/062* (2013.01); *A61M 2205/0222* (2013.01)

(58) Field of Classification Search
  CPC ................... A61M 2025/0057; A61M 25/0071
  See application file for complete search history.

(56) References Cited

U.S. PATENT DOCUMENTS

| | | |
|---|---|---|
| 3,788,326 A | 1/1974 | Jacobs |
| 4,173,981 A | 11/1979 | Mortensen |

(Continued)

FOREIGN PATENT DOCUMENTS

| | | |
|---|---|---|
| DE | 212017000340 U1 | 4/2020 |
| JP | 2020049277 A | 4/2020 |

(Continued)

OTHER PUBLICATIONS

MICROVENTION—Wedge Microcatheter—Downloaded Feb. 3, 2021—Available from Internet <URL: https://www.microvention.com/product/wedge>.

(Continued)

*Primary Examiner* — William R Carpenter
(74) *Attorney, Agent, or Firm* — Gallium Law; Wesley Schwie, Esq.; Isabel Fox

(57) ABSTRACT

A vasculature navigation system may include a dilator having a proximal end and a distal end located opposite the proximal end, the dilator comprising a guidewire lumen extending between the proximal end and the distal end, the dilator defining a proximal portion and a distal portion located opposite the proximal portion. In some embodiments, the vasculature navigation system also includes an access port located at the proximal end of the dilator, a distal port located at the distal end of the dilator, and a hemostasis valve coupled to the proximal portion of the dilator. The hemostasis valve may be configured to control fluid flow between the proximal portion and the distal portion. In some embodiments, a flush port is coupled to the proximal portion of the dilator and located distal to the hemostasis valve, and the flush port is coupled to a fluid supply source.

20 Claims, 42 Drawing Sheets

(56) References Cited

U.S. PATENT DOCUMENTS

| | | | |
|---|---|---|---|
| 4,927,418 A * | 5/1990 | Dake | A61M 25/007 604/528 |
| 5,098,405 A | 3/1992 | Peterson | |
| 5,318,531 A | 6/1994 | Leone | |
| 5,333,620 A | 8/1994 | Moutafis | |
| 5,514,092 A | 5/1996 | Forman | |
| 5,797,857 A | 8/1998 | Obitsu | |
| 5,800,408 A * | 9/1998 | Strauss | A61M 25/007 604/246 |
| 5,810,012 A | 9/1998 | Lynch | |
| 5,817,057 A * | 10/1998 | Berenstein | A61M 25/0122 604/95.01 |
| 5,891,110 A | 4/1999 | Larson | |
| 6,179,828 B1 * | 1/2001 | Mottola | A61M 25/0075 604/533 |
| 6,295,990 B1 | 10/2001 | Lewis | |
| 6,613,066 B1 | 9/2003 | Fukaya | |
| 6,632,200 B2 | 10/2003 | Guo | |
| 6,652,472 B2 | 11/2003 | Jafari | |
| 6,723,073 B2 | 4/2004 | Ley | |
| 6,837,870 B2 | 1/2005 | Duchamp | |
| 6,905,481 B2 | 6/2005 | Sirimanne | |
| 6,966,896 B2 | 11/2005 | Kurth | |
| 7,008,412 B2 | 3/2006 | Maginot | |
| 7,115,134 B2 | 10/2006 | Chambers | |
| 7,641,645 B2 | 1/2010 | Schur | |
| 7,766,868 B2 | 8/2010 | Goode | |
| 8,048,004 B2 | 11/2011 | Davis | |
| 8,262,671 B2 | 9/2012 | Osypka | |
| 8,403,912 B2 | 3/2013 | McFerran | |
| 8,454,536 B2 | 6/2013 | Raulerson | |
| 8,715,276 B2 | 5/2014 | Thompson | |
| 9,119,656 B2 | 9/2015 | Bose | |
| 9,408,667 B2 | 8/2016 | Okazaki | |
| 9,504,805 B2 | 11/2016 | Vreeman | |
| 9,681,882 B2 | 6/2017 | Garrison | |
| 10,105,525 B2 | 10/2018 | Braga | |
| 10,376,675 B2 | 8/2019 | Mitchell | |
| 10,426,497 B2 | 10/2019 | Chou | |
| 10,485,435 B2 | 11/2019 | Griswold | |
| 10,543,006 B2 | 1/2020 | Bonne, I | |
| 10,682,493 B2 | 6/2020 | Tran | |
| 10,743,893 B2 | 8/2020 | Garrison | |
| 11,090,466 B1 * | 8/2021 | Nicholson | A61M 39/06 |
| 2003/0040694 A1 | 2/2003 | Dorros | |
| 2005/0256503 A1 | 11/2005 | Hall | |
| 2006/0229573 A1 | 10/2006 | Lamborne | |
| 2010/0204634 A1 * | 8/2010 | Baxter | A61M 25/007 604/537 |
| 2010/0217276 A1 | 8/2010 | Garrison | |
| 2013/0035628 A1 | 2/2013 | Garrison | |
| 2014/0228808 A1 | 8/2014 | Webster | |
| 2014/0257245 A1 | 9/2014 | Rosenbluth | |
| 2015/0099936 A1 | 4/2015 | Burdulis | |
| 2018/0049759 A1 | 2/2018 | Thomas | |
| 2018/0193042 A1 * | 7/2018 | Wilson | A61B 17/12109 |
| 2019/0117250 A1 | 4/2019 | Farhangnia | |
| 2019/0336265 A1 | 11/2019 | Batiste | |
| 2020/0171277 A1 | 6/2020 | Garrison | |

FOREIGN PATENT DOCUMENTS

| | | |
|---|---|---|
| WO | 2005049110 A2 | 6/2005 |
| WO | 2019027380 A1 | 2/2019 |

OTHER PUBLICATIONS

TELEFLEX—Pronto Extraction Catheters—Downloaded Feb. 3, 2021—Available from Internet <URL: https://www.teleflex.com/usa/en/product-areas/interventional/peripheral-interventions/pronto-extraction-catheters/index.html>.

TELEFLEX—Turnpike Catheters—Downloaded Feb. 3, 2021—Available from Internet <URL: https://www.teleflex.com/usa/en/product-areas/interventional/peripheral-interventions/turnpike-catheter/>.

Frolich Am, Kim W, Stribrny K, et al—The novel Tenzing 7 delivery catheter designed to deliver intermediate catheters to the face of embolus without crossing: clinical performance predicted in anatomically challenging model—Journal of NeuroInterventional Surgery—Sep. 3, 2020—doi: 10.1136/neurintsurg-2020-016412—Downloaded Feb. 3, 2021—Available from Internet <URL: https://jnis.bmj.com/content/eariy/2020/09/03/neurintsurg-2020-016412>.

PENUMBRA—Penumbra Jet 7 Max—Feb. 27, 2020—Downloaded Feb. 3, 2021—Available from Internet <URL: https://www.accessdata.fda.gov/cdrh_docs/pdf19/K191946.pdf>.

B. Braun Medical Inc.—Contiplex Tuohy: Non-stimulating catheter system for continuous nerve block.—Downloaded Feb. 3, 2021—Available from Internet <URL: https://www.bbraunusa.com/en/products/b/contiplex-tuohy.html>.

* cited by examiner

VASCULATURE NAVIGATION SYSTEMS AND METHODS

CROSS-REFERENCE TO RELATED APPLICATIONS

The entire contents of the following application are incorporated by reference herein: U.S. application Ser. No. 17/107,791; filed Nov. 30, 2020; and entitled CATHETER SYSTEMS AND DEVICES FOR ACUTE ISCHEMIC THROMBECTOMY.

BACKGROUND

Field

Various embodiments disclosed herein relate to catheter systems. Certain embodiments relate to catheter systems for performing a thrombectomy or an embolectomy.

Description of Related Art

Mechanical thrombectomy is a procedure that removes clots through endovascular intervention to restore blood flow to the brain during acute ischemic stroke. Acute Ischemic Stroke ("AIS") can be caused by thrombus, embolus or other occlusions in regions of the internal carotid artery such as the Petrous segment, Cavernous segment and/or Cerebral segment, or the middle cerebral artery, such as the MCA bifurcation, the M1 segment, and/or the M2 segment. Approaches for performing thrombectomy or embolectomy to treat AIS include accessing the vasculature and navigating a balloon guiding catheter to the carotid artery at a location upstream from the occlusion, typically at a proximal location in the artery such as the cervical segment of the ICA. After the balloon is inflated to provide antegrade blood flow cessation, retrieval devices can be passed through the balloon guiding catheter to retrieve the embolus. Thrombectomy tools such as stent retrievers, aspiration catheters, or both can be delivered directly to the embolus through the guiding catheter to complete the retrieval process, after which the balloon is deflated and the retrieval and guide catheters are retracted to the access point.

Navigation through the vasculature to the face of the occlusion can often be difficult, due to the distal edge of a balloon guiding catheter or another primary device (e.g., sheath, aspiration catheter, other guide catheter, and the like) becoming "stuck" or stopped on the ledge of a blood vessel, such as the ostium of the ophthalmic artery, or by carotid plaque or lesions elsewhere in the vasculature, which is also known as "shelf effect." Some efforts have been made to reduce shelf effect through the use of microcatheters, where the primary device is tracked over a microcatheter, and the microcatheter is tracked over a guidewire. However, shelf effect may still be an issue when there is a significant difference between the inner diameter of the primary device and the outer diameter of the microcatheter, as the gap between the microcatheter and the primary device may still become "stuck" during navigation through the vasculature.

For example, stroke aspiration catheters tracked over existing microcatheters can still become stuck or stopped on the ledge of the ostia, such as the ostium of the ophthalmic artery, when the ledge of the stroke catheter makes contact with the edge of the arterial origin. As such, further advancement of the catheter through the vasculature may become much more challenging or impossible when using existing technologies.

Numerous attempts have been made to develop solutions to reduce the shelf effect issues faced by clinicians performing various procedures. For example, U.S. Pat. No. 7,641,645, assigned to AngioDynamics, Inc., of Queensbury, N.Y., USA, discloses a "Combination Thrombolytic Infusion Catheter and Dilator System" that includes an internal dilator removably coupled to a drug delivery catheter. However, the infusion catheter is intended to administer lytic agents to grafts that are used to connect a vein to an artery for bypass and/or dialysis procedures, rather than to treat AIS via an intercranial procedure, such as a thrombectomy.

Another example of an attempt to reduce shelf effect is disclosed in U.S. Pat. No. 10,682,493, assigned to MicroVention, Inc., of Aliso Viejo, Calif., USA. The '493 patent discloses "Intravascular Treatment Site Access" via a device intended to reduce the gap between a catheter and a guidewire. The patented device includes a guidewire with an enlarged distal portion. The device does not include a microcatheter, dilator, or another intermediary device intended to track over the guidewire between the guidewire and an outer catheter.

Yet another example is the "Transcarotid Neurovascular Catheter" disclosed in U.S. Patent Application No. 2020/0171277, assigned to Silk Road Medical, Inc., of Sunnyvale, Calif., USA. The claimed device comprises a neurovascular catheter designed for direct insertion into the carotid artery. As a result, the claimed device requires a working length significantly shorter than the working length required for a catheter/internal device (e.g., microcatheter, dilator, or the like) designed for insertion in a femoral artery or other artery located further from the brain than the carotid artery. In addition, like the '493 patent, the '277 application discloses a neurovascular catheter without an internal/intermediary device.

U.S. Pat. No. 9,408,667, assigned to Olympus Corporation of Tokyo, Japan, discloses a "Guide Sheath and Guide Sheath System." The patented sheath comprises a tubular sheath designed for providing anchoring support upon insertion into the pericardial cavity. Rather than aiding in navigation through the vasculature, the guide sheath is intended to hold the system in position.

Another device designed to reduce shelf effect is the "Wedge Microcatheter" produced by MicroVention, Inc. The device includes an enlarged bulb segment and claims to "optimize SOFIA 6F Catheter navigation past tortuous bifurcations allowing SOFIA 6F Catheter to access extremely challenging occlusion locations." As indicated, the MicroVention device is specifically described for use with the SOFIA 6F catheter, which severely limits the utility of the device. A device designed for use with any stroke catheter would greatly improve upon the utility currently provided by the MicroVention device.

The Tenzing 7 Delivery Catheter, produced by Route 92 Medical of San Mateo, Calif., USA, is another device aimed at reducing shelf effect. The tapered delivery catheter is designed to "deliver intermediate catheters to the face of an embolus without crossing." Because the delivery catheter is specifically designed to "not disturb" the embolus, it is not designed for use over a guidewire, as guidewires generally contact the embolus.

SUMMARY

The disclosure includes a catheter system comprising an elongated access assist device having a proximal end and a distal end located opposite the proximal end, the elongated access assist device comprising a guidewire lumen extending between the proximal end and the distal end, the elongated access assist device defining a proximal portion and a distal portion located opposite the proximal portion. The catheter system may also include an access port located at the proximal end of the elongated access assist device, the access port configured to receive a guidewire, and a distal port located at the distal end of the elongated access assist device, the distal port configured to further receive the guidewire. In many embodiments, the catheter system further includes a hemostasis valve coupled to the proximal portion of the elongated access assist device, the hemostasis valve configured to control fluid flow between the proximal portion and the distal portion, and a flush port coupled to the proximal portion of the elongated access assist device and located distal to the hemostasis valve, wherein the flush port is configured to couple to a fluid supply source. The catheter system may include a tapered portion defining at least part of the distal portion of the elongated access assist device, wherein an outer surface of the tapered portion tapers downward toward the distal end, and a plurality of microperforations coupled to at least the distal portion of the elongated access assist device, the plurality of microperforations configured to release fluid from the fluid supply source.

In some embodiments, the hemostasis valve is integrated into the elongated access assist device. The fluid supply source may include a supply of at least one of saline and contrast dye. In many embodiments, the guidewire lumen is configured to receive the guidewire such that the guidewire extends from the access port of the elongated access assist device through the distal port of the elongated access assist device.

The tapered portion may define a length of less than or equal to twenty centimeters. In many embodiments, the plurality of microperforations are substantially evenly spaced and dispersed across the tapered portion. The plurality of microperforations may be configured to facilitate a substantially continuous release of fluid.

In some embodiments, the catheter system further comprises a first marker band coupled to a distal tip of the tapered portion, wherein the first marker band comprises a radiopaque material. The system may include a second marker band coupled to the elongated access assist device proximal to the tapered portion, wherein the second marker band comprises radiopaque material. In some embodiments, the radiopaque material comprises at least one of iridium and platinum.

The system may further comprise a neurovascular sheath sized and configured to slideably receive at least a portion of the elongated access assist device, where the neurovascular sheath defines an inner diameter and the elongated access assist device defines an outer diameter. The outer diameter may be about 90% of the inner diameter. The inner diameter of the neurovascular sheath may define a diameter of about 0.088 inches and the outer diameter of the elongated access assist device may define a diameter of about 0.079 inches.

In some embodiments, the system further comprises a neurovascular aspiration catheter sized and configured to slideably receive at least a portion of the elongated access assist device, where the neurovascular aspiration catheter defines an inner diameter and the elongated access assist device defines an outer diameter. The outer diameter may be about 90% of the inner diameter. The inner diameter of the neurovascular aspiration catheter may define a diameter of about 0.072 inches and the outer diameter of the elongated access assist device may define a diameter of about 0.065 inches.

In some embodiments, the tapered portion defines a proximal outer diameter of about 0.068 inches, a proximal inner diameter of about 0.02 inches, a distal outer diameter of about 0.023 inches, whereby the distal outer diameter is located distal the proximal outer diameter, and a distal inner diameter of about 0.018 inches, whereby the distal inner diameter is located distal the proximal inner diameter. In some embodiments, the tapered portion defines a symmetrical conical shape. The tapered portion may define an asymmetrical conical shape.

In many embodiments, the system further comprises a hydrophilic coating located on at least a portion of an exterior surface of the elongated access assist device. The elongated access assist device may define a working length of about 133 centimeters. The elongated access assist device may define a working length of about 91 centimeters. In some embodiments, the distal port defines a guidewire lumen diameter of about 0.02 inches.

The disclosure includes a vasculature navigation system comprising a dilator having a proximal end and a distal end located opposite the proximal end, the dilator comprising a guidewire lumen extending between the proximal end and the distal end, the dilator defining a proximal portion and a distal portion located opposite the proximal portion. The system may further comprise an access port located at the proximal end of the dilator and configured to receive a guidewire, and a distal port located at the distal end of the dilator, the distal port configured to further receive the guidewire. In some embodiments, the system includes a hemostasis valve coupled to the proximal portion of the dilator, the hemostasis valve configured to control fluid flow between the proximal portion and the distal portion. The system may include a flush port coupled to the proximal portion of the dilator and located distal to the hemostasis valve, wherein the flush port may be configured to couple to a fluid supply source. The system may also include a tapered portion defining at least part of the distal portion of the dilator, wherein an outer surface of the tapered portion tapers downward toward the distal end.

In many embodiments, the vasculature navigation system further comprises a plurality of microperforations coupled to at least a portion of an exterior surface of the dilator, the plurality of microperforations configured to release fluid from the fluid supply source. The plurality of microperforations may be configured to release a substantially continuous flow of fluid from the fluid supply source. In some embodiments, each microperforation of the plurality of microperforations defines a diameter of about 0.01 inches on the exterior surface of the dilator. Each microperforation of the plurality of microperforations may define an aperture.

The fluid supply source may be pressurized to an extent sufficient to enable propulsion of the dilator upon release of fluid via the plurality of microperforations. In some embodiments, the fluid is pressurized within the dilator to the extent sufficient to enable propulsion of the dilator as the fluid is released from the plurality of microperforations. The fluid supply source may comprise a supply of saline.

In some embodiments, the plurality of microperforations is arranged in a spiral configuration around the exterior surface of the dilator. Each microperforation of the plurality of microperforations may be evenly spaced from an adjacent microperforation. The plurality of microperforations may be coupled to the proximal portion of the dilator.

In many embodiments, the system further comprises a hydrophilic coating located on the distal portion of the dilator, wherein the hydrophilic coating is configured to reduce friction between the dilator and a patient's vasculature. The plurality of microperforations and the hydrophilic coating may enable navigation of the dilator through a patient's vasculature by reducing friction between the dilator and the patient's vasculature. In some embodiments, the plurality of microperforations may be located proximal to the hydrophilic coating, and the fluid released from the plurality of microperforations may be configured to flow over the hydrophilic coating.

In some embodiments, the dilator comprises a reinforcement structure located within a wall of the dilator, the reinforcement structure defining a coil shape. The reinforcement structure may be located within substantially an entire length of the dilator. In some embodiments, the reinforcement structure comprises a round wire.

The dilator may be configured to be received by a primary device such that at least the tapered portion of the dilator extends distal a distal end of the primary device, and the dilator may comprise a hydrophilic coating configured to reduce friction between the dilator and the primary device.

The disclosure may include a method of navigating a dilator through a patient's vasculature, and the method may comprise inserting, via an access site, the dilator into the patient's vasculature, wherein the dilator comprises an access port located at a proximal end of the dilator and configured to receive a guidewire, a distal port located at a distal end of the dilator and configured to further receive the guidewire, a hemostasis valve coupled to a proximal portion of the dilator and configured to control fluid flow between the proximal portion and a distal portion, a flush port coupled to the proximal portion of the dilator and configured to couple to a fluid supply source, and a plurality of microperforations coupled to an exterior surface of the dilator. In some embodiments, the method further comprises pressurizing the fluid supply source to a pressure sufficient to enable propulsion of the dilator and releasing, via the plurality of microperforations, at least a portion of fluid from the pressurized fluid supply source, wherein releasing at least the portion of fluid is configured to enable propulsion of the dilator through the patient's vasculature. The method may further comprise inserting, over the dilator, a primary device into the patient's vasculature, wherein the primary device is configured to perform a treatment.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

DETAILED DESCRIPTION

Figure 1:
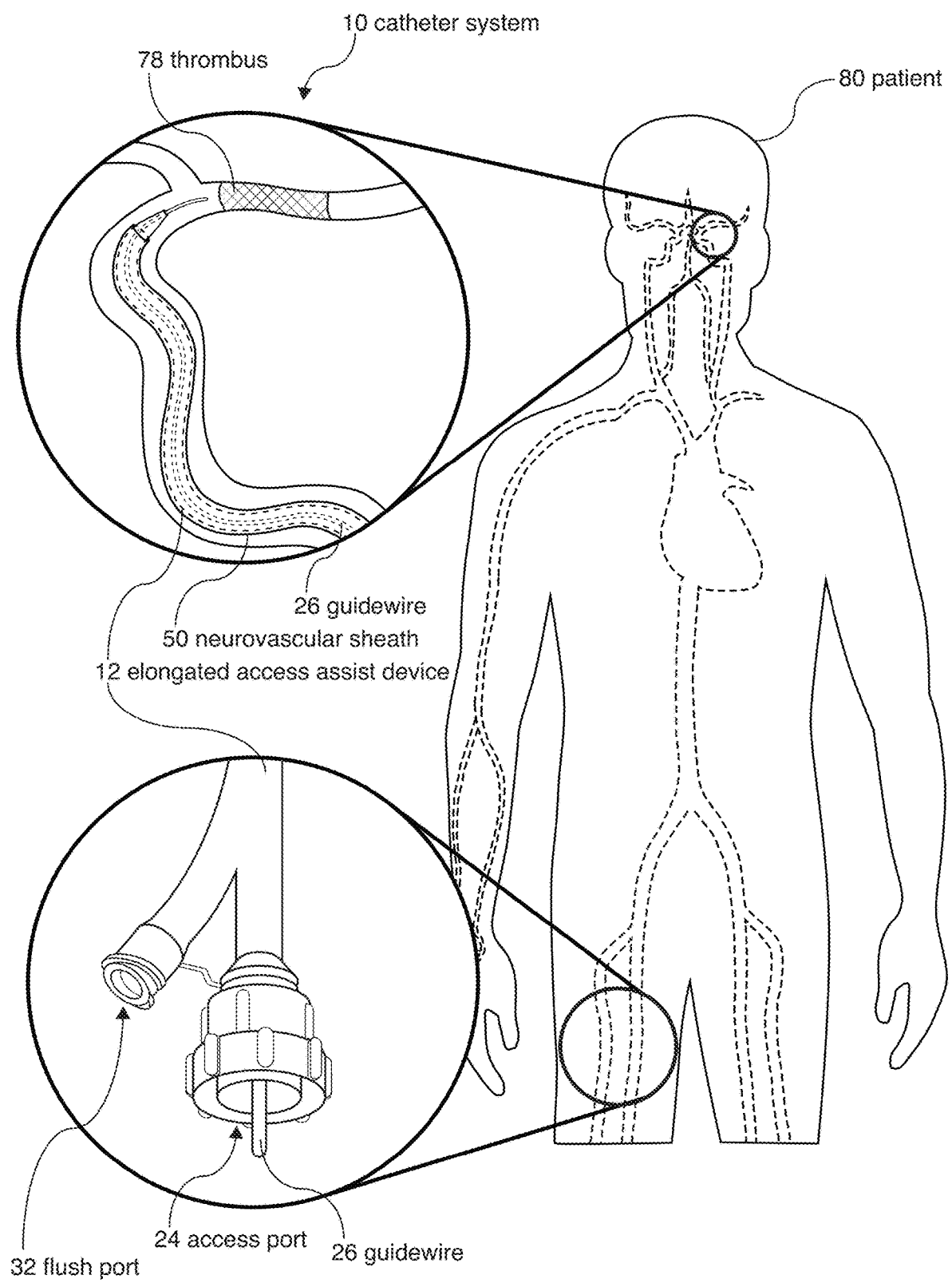
FIG. 1 illustrates a diagrammatic view of a patient undergoing a procedure for removal of a thrombus using an elongated access assist device, according to some embodiments.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. All such aspects or advantages are not necessarily achieved by any particular embodiment. For example, various embodiments may be carried out in a manner that achieves or optimizes one advantage or group of advantages as taught herein without necessarily achieving other aspects or advantages as may also be taught or suggested herein.

Introduction

An objective of the present invention is to provide a catheter system that reduces shelf effect by providing a smooth and soft transition between the distal edge of the access assist device and the conjunctive primary device (e.g., neurovascular sheath, guide catheter, aspiration catheter, and the like).

LIST OF REFERENCE NUMERALS

10—catheter system
12—elongated access assist device
14—proximal end
16—distal end
18—guidewire lumen
20—proximal portion
22—distal portion
24—access port
26—guidewire
28—distal port
30—hemostasis valve
31—port
32—flush port
34—fluid supply source
36—tapered portion
38—outer surface (of tapered portion)
40—plurality of microperforations
42—fluid
44—marker band
44a—first marker band
44b—second marker band
44c—third marker band
46—distal tip
48—distance from distal tip
50—neurovascular sheath
52—inner diameter (of neurovascular sheath)
54—outer diameter (of access assist device)
56—neurovascular aspiration catheter
57—outer diameter (of access assist device)
58—inner diameter (of neurovascular aspiration catheter)
60—proximal outer diameter (tapered portion)
62—proximal inner diameter (tapered portion)
64—distal outer diameter (tapered portion)
66—distal inner diameter (tapered portion)
68—symmetrical conical shape
70—asymmetrical conical shape
71—asymmetrical conical shape
72—hydrophilic coating
74—exterior surface (of elongated access assist device)
76—working length
78—thrombus
80—patient
82—taper length
100—vasculature navigation system
102—dilator
104—proximal end
106—distal end
110—proximal portion
112—distal portion
114—access port
116—guidewire
120—hemostasis valve
122—flush port
123—fluid
124—fluid supply source
126—tapered portion
128—outer surface (of tapered portion)
130—plurality of microperforations
132—exterior surface (of dilator)
134—spiral configuration
136—hydrophilic coating
138—reinforcement structure
140—inner shaft
142—outer shaft
144—PTFE liner
146—inner PEBA layer
148a—first outer section
148b—second outer section
148c—third outer section
148d—fourth outer section
150—diameter FIG. 1 illustrates a diagrammatic view of a patient 80 undergoing a procedure to remove a thrombus 78 using a catheter system 10. As shown, the system 10 may include an elongated access assist device 12 as well as a guidewire 26, which may extend through an interior portion of the elongated access assist device 12. In many embodiments, the elongated access assist device 12 includes an access port 24 and a flush port 32 located adjacent a proximal end of the elongated access assist device 12. As shown in FIG. 1, the elongated access assist device 12 may extend through an interior portion of a primary device, such as a neurovascular sheath 50, which is discussed further on with regards to FIG. 21.

FIG. 1 shows the thrombus 78 located in a cranial region of the patient 80. In some embodiments, the thrombus 78 is located in a region of the internal carotid artery ("ICA") or the middle cerebral artery ("MCA") of the patient 80. The proximal end 14 of the elongated access assist device 12 is shown adjacent a groin region of the patient 80. In many embodiments, the elongated access assist device 12 is inserted into the vasculature through an arteriotomy located in the common femoral artery of the patient 80. The arteriotomy may be located in an artery other than the common femoral artery, though is usually located in a groin or leg region of the patient 80. In some embodiments, the arteriotomy is located in the radial artery near the lower arm or wrist region of the patient 80.

Figure 2:
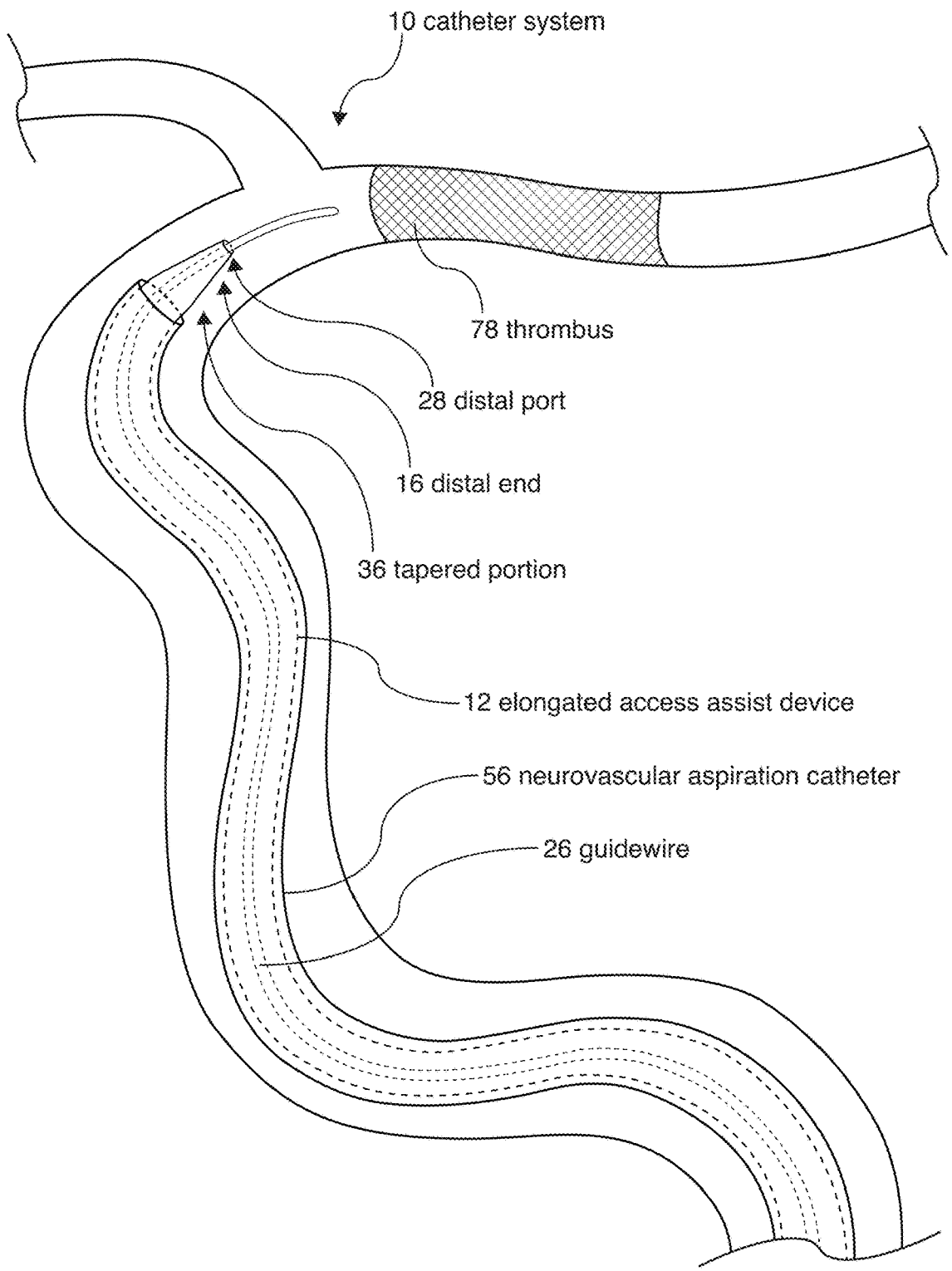
FIG. 2 illustrates a perspective view of a distal portion of an elongated access assist device, according to some embodiments.

FIG. 2 shows a more detailed view of the elongated access assist device 12 located in the vasculature near the thrombus 78. As demonstrated, in many embodiments, a distal end 16 of the elongated access assist device 12 comprises a tapered portion 36, which tapers down to a distal port 28. Stated differently, an outer surface of the tapered portion 36 tapers downward toward the distal end 16. The distal port 28 may enable the removal of the thrombus 78 by providing an opening for the thrombus 78 to enter the elongated access assist device 12 and exit the patient 80 through the access port 24. In some embodiments, the elongated access assist device 12 is retracted prior to removal of the thrombus 78.

The distal port 28 may also provide an opening for the guidewire 26 to protrude from the distal end 16 of the elongated access assist device 12. In some embodiments, the guidewire 26 extends beyond the distal end 16 in order to facilitate navigation of the elongated access assist device 12 through the vasculature. The guidewire 26 may also be configured to puncture the thrombus 78. For example, in a mechanical thrombectomy procedure, the guidewire 26 may be used to physically break apart the thrombus 78 prior to, or simultaneously with, the application of aspiration (e.g., suction) to the elongated access assist device 12 such that the fragments of the thrombus 78 are pulled through the elongated access assist device 12 via the aspiration force. Alternatively, an aspiration catheter may be used to remove the thrombus 78. For example, the elongated access assist device 12 may be advanced to the face of the thrombus 78 while located at least partially within a primary device, such as a sheath. The elongated access assist device 12 may then be removed and replaced with a smaller elongated access assist device 12. The sheath may then be removed and replaced with and aspiration catheter, which is tracked over the smaller elongated access assist device 12. Finally, upon removal of the smaller elongated access assist device 12 from the aspiration catheter, the aspiration force may be applied to the aspiration catheter to facilitate removal of the thrombus 78.

In many embodiments, the tapered portion 36 facilitates navigation of the elongated access assist device 12 throughout the vasculature, especially more tortuous sections such as the aortic arch, the common carotid arteries, the internal carotid arteries, the cerebral arteries, the ostium of the ophthalmic artery, and posterior neurovasculature. It should be noted that the cited arteries are included for example and form a nonlimiting list. The elongated access assist device 12 may be configured to navigate portions of the vasculature not specifically stated in this disclosure. In some embodiments, the tapered portion 36 reduces the "shelf effect" discussed in the Background section of this disclosure by providing a smooth and soft transition between the distal end 16 of the elongated access assist device 12 and the conjunctive primary device (e.g., neurovascular sheath 50, guide catheter, aspiration catheter 56, and the like; not shown in FIG. 2). Different primary devices and the transition between the elongated access assist device 12 and each primary device will be shown in, and discussed further with reference to, FIGS. 21-26. As shown in FIG. 2, the elongated access assist device 12 extends through an interior portion of a neurovascular aspiration catheter 56.

Figure 3:
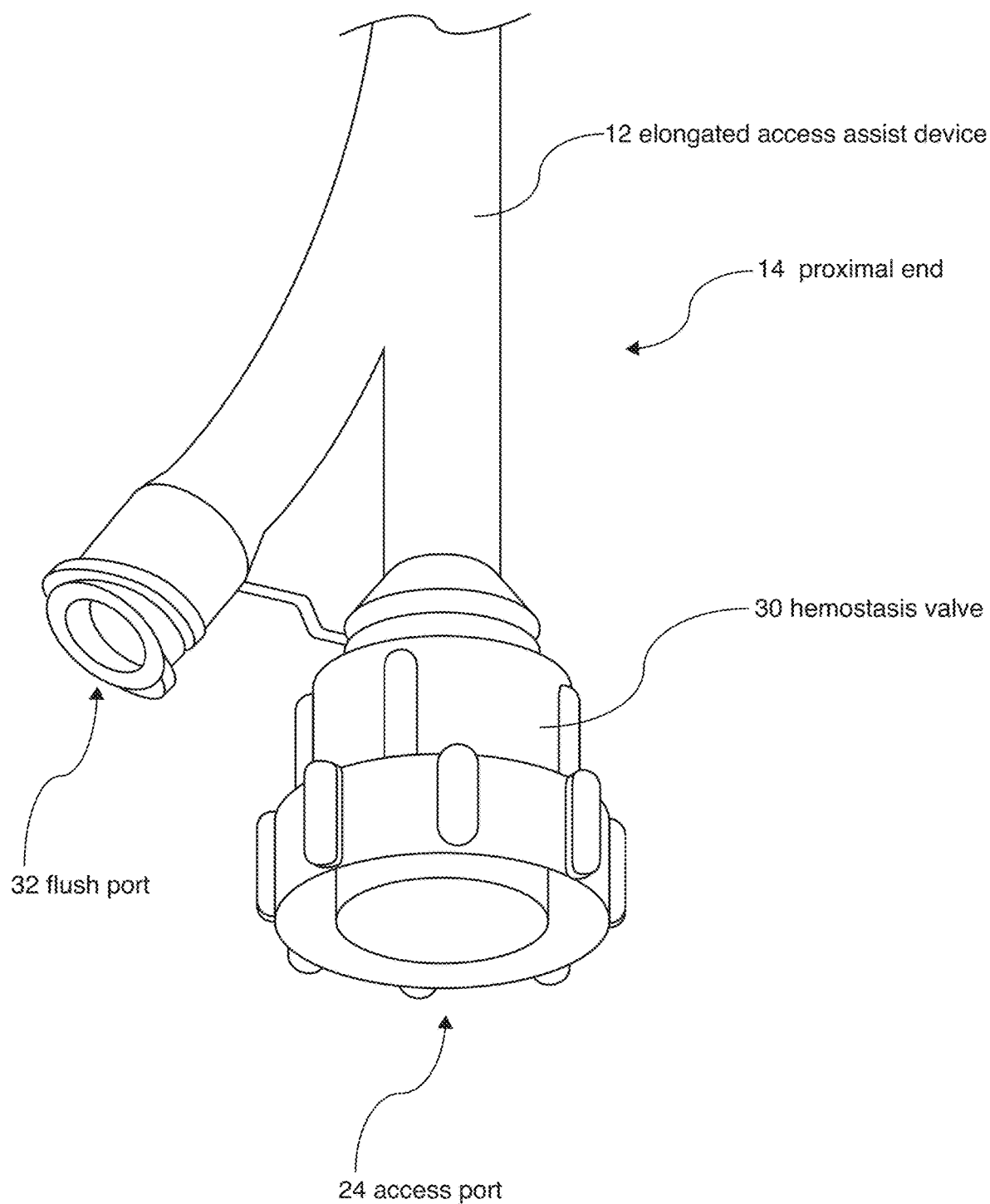
FIG. 3 illustrates a perspective view of a proximal portion of an elongated access assist device, according to some embodiments.

FIG. 3 shows a more detailed view of the proximal end 14 of the elongated access assist device 12, including the flush port 32, access port 24, and hemostasis valve 30. In many embodiments, the proximal end 14 is located opposite the distal end 16, shown in FIG. 2. It should be noted that the access port 24 and the hemostasis valve 30 may be considered the same element of the elongated access assist device 12. In other words, the hemostasis valve 30 may be integrated into the elongated access assist device 12, rather than a separate element coupled to the elongated access assist device 12. Accordingly, reference to the access port 24 may also be considered reference to the hemostasis valve 30, and vice versa. In some embodiments, the elongated access assist device 12 does not include a hemostasis valve 30.

Though not shown in FIG. 3, in many embodiments, the access port 24 is configured to receive the guidewire 26, which extends through the body of the elongated access assist device 12 and through the distal port 28, as shown in FIGS. 1 and 2. The access port 24 may also be configured to receive any other device inserted into the elongated access assist device 12, such as a microcatheter, dilator, and the like. In some embodiments, the flush port 32 is configured to couple to a fluid supply source, which will be discussed in greater detail later in the disclosure. As illustrated in FIG. 3, the flush port 32 may be located distal to the hemostasis valve 30. In many embodiments, both the flush port 32 and the hemostasis valve 30 are located on a proximal portion, adjacent the proximal end 14, of the elongated access assist device 12. The flush port 32 may be configured to couple directly to the hemostasis valve 30.

The hemostasis valve 30 may be configured to control fluid flow between the proximal portion and the distal portion of the elongated access assist device 12. For example, during a thrombectomy procedure, the hemostasis valve 30 may prevent backflow of blood from the distal portion out through the proximal portion of the elongated access assist device 12. In some embodiments, the hemostasis valve 30 comprises a rotating seal configured to allow the insertion of the guidewire 26 while reducing leakage of blood out of the access port 24 during the procedure. The rotating seal may be loosened to allow movement of the guidewire 26, then tightened when the guidewire 26 is in the desired location within the elongated access assist device 12 and/or the vasculature. In some embodiments, the rotating seal is threadably coupled to the hemostasis valve 30. Any suitable type of seal other than a rotating seal may be used.

Figure 4:
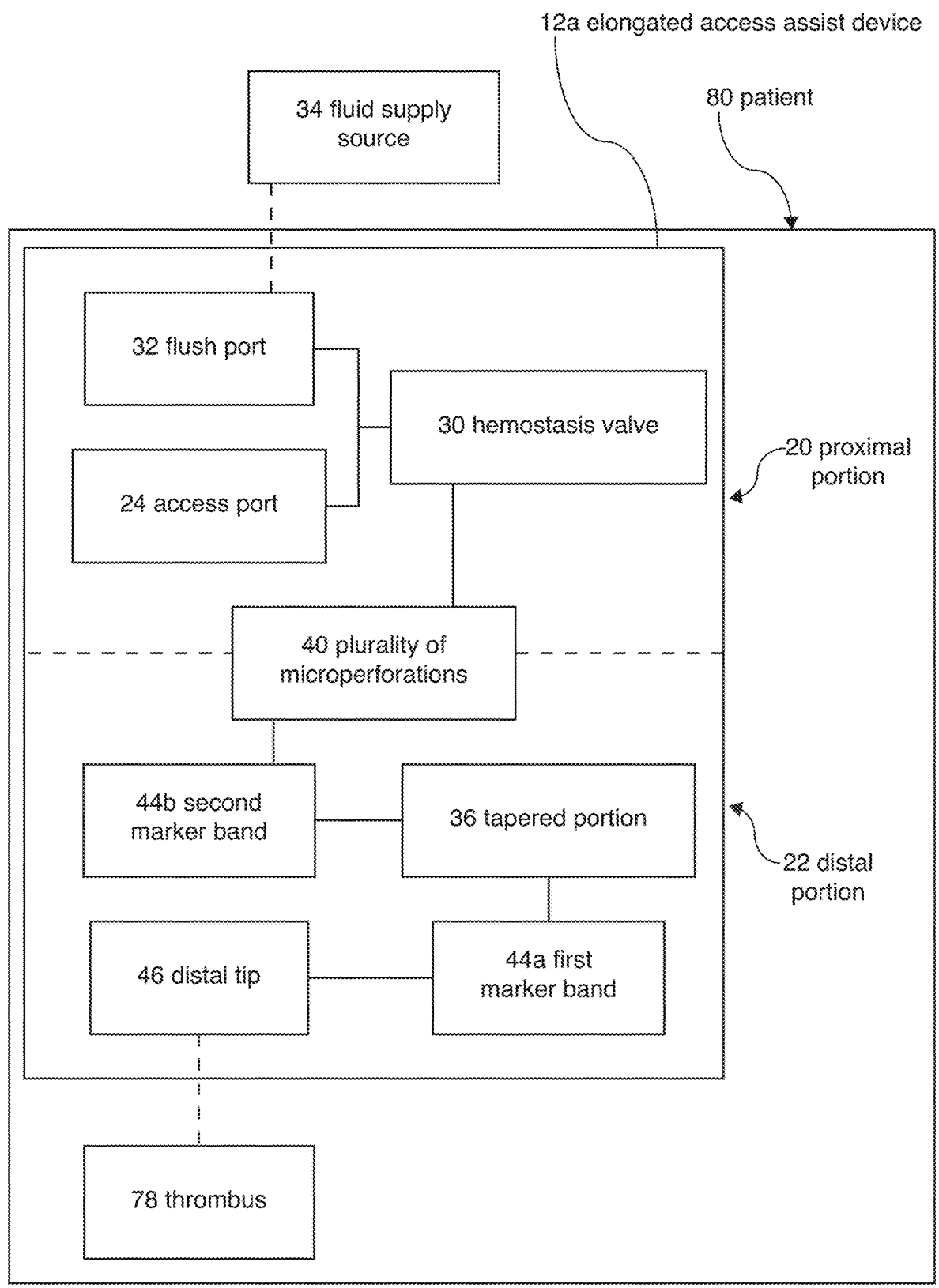
FIGS. 4 and 5 illustrate schematic representations of a catheter system, according to some embodiments.
Figure 5:
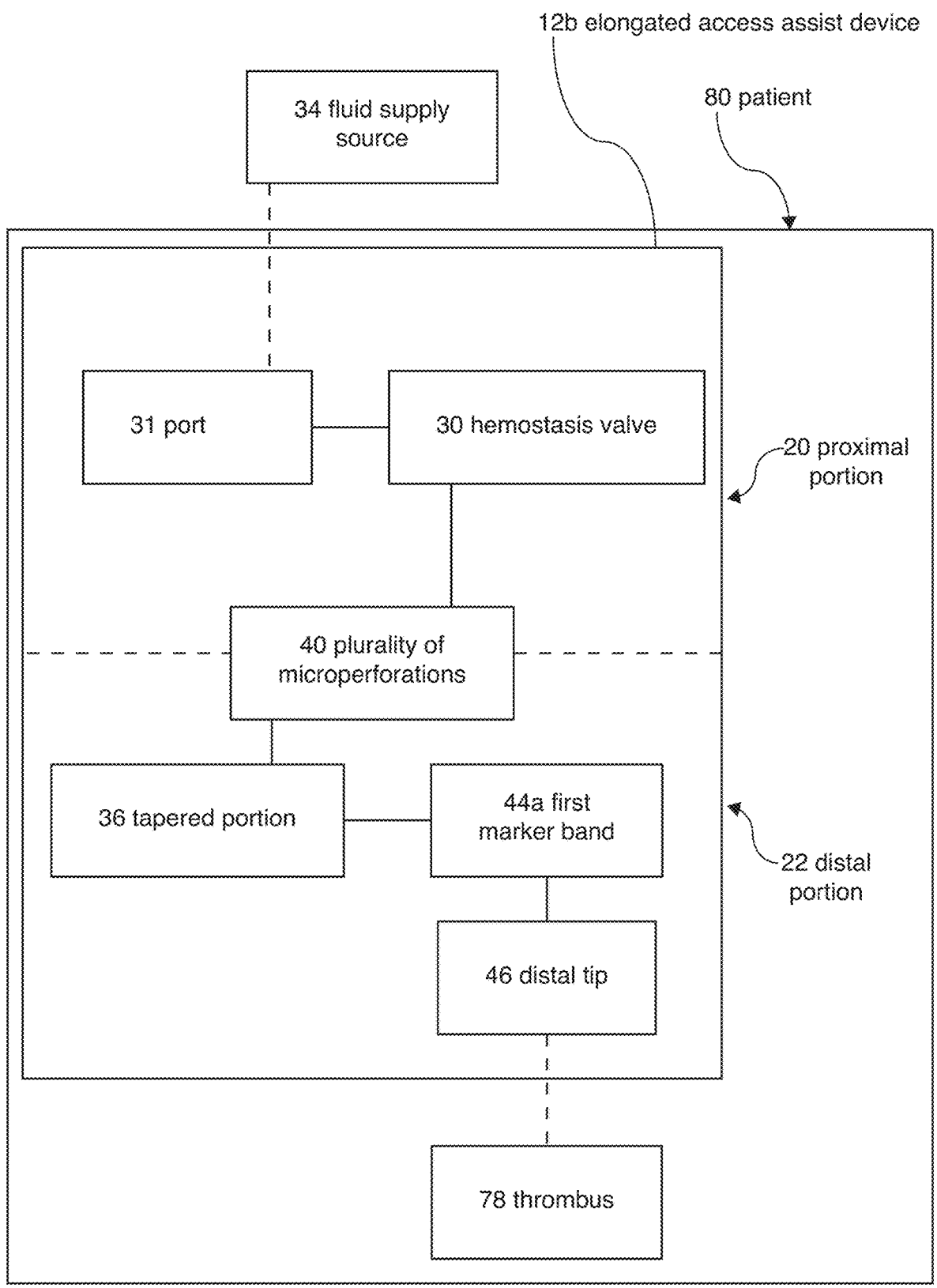

FIGS. 4 and 5 illustrate schematic representations of the catheter system 10, including some components of the elongated access assist device 12, the patient 80, the fluid supply source 34, and the thrombus 78. FIG. 4 shows a schematic of an elongated access assist device 12a, while FIG. 5 shows a schematic of another elongated access assist device 12b, including fewer components than the embodiment illustrated in FIG. 4. FIGS. 4 and 5 may be considered to show the "flow" of a device (e.g., guidewire) or fluid (e.g., saline) through the elongated access assist device 12a, 12b. FIGS. 4 and 5 also illustrate the proximal portion 20 and distal portion 22 of the elongated access assist device 12a, 12b, and which components are located in each portion, according to some embodiments. As such, the "flow" through the elongated access assist device 12a, 12b illustrated in FIGS. 4 and 5 moves from the most proximal location to the most distal location.

For example, referring to FIG. 4, fluid may flow from the fluid supply source 34 through the flush port 32 of the elongated access assist device 12a. As such, the elongated access assist device 12 may be considered to be in fluid communication with the fluid supply source 34. The access port 24 and flush port 32 are shown converging in the hemostasis valve 30, as, in some embodiments, the hemostasis valve 30 comprises the flush port 32 and the access port 24. From the hemostasis valve 30, the fluid may flow to and, for at least a portion of the fluid, through the plurality of microperforations 40. In some embodiments, the fluid flows through an annular space within the elongated access assist device 12.

The plurality of microperforations 40 are shown in both the proximal portion 20 and distal portion 22 of the elongated access assist device 12a because, in many embodiments, the plurality of microperforations 40 are located in both portions 20, 22 of the elongated access assist device 12a. The fluid remaining in the elongated access assist device 12a (i.e., the fluid that was not released through the plurality of microperforations 40) continues in a distal direction through the elongated access assist device 12a to the second marker band 44b, which, in some embodiments, is located immediately proximal to the tapered portion 36. As the fluid moves through an interior portion of the elongated access assist device the fluid may pass by the second marker band 44b through the tapered portion 36, whereby the fluid passes by the first marker band 44a, which, in some embodiments, is located substantially immediately proximal to the distal tip 46. As shown in FIGS. 1 and 2, the distal tip 46 may be located adjacent the thrombus 78. The patient 80 is also included in FIG. 4 located adjacent the proximal portion 20. In this context, the "patient 80" may be considered to represent an arteriotomy in the patient 80, where the elongated access assist device 12a is inserted.

It should be noted that though the "flow" discussed with reference to FIG. 4 is discussed in terms of the flow of fluid, substantially the same path may be taken by a guidewire 26, though the guidewire 26 would not originate from the fluid supply source 34, enter the flush port 32, and thereby exit through the plurality of microperforations 40. It should also be noted that the fluid "meeting" the first and/or second marker bands 44a, 44b does not necessarily imply contact between the fluid and the marker bands 44a, 44b. For example, the fluid may flow through an interior portion of the elongated access assist device 12a while the first and second marker bands 44a, 44b are located on an exterior portion of the device 12a. In some embodiments, the fluid does come into contact with the first and/or second marker bands 44a, 44b, as the fluid is released through the plurality of microperforations 40 on the surface of the elongated access assist device 12a.

FIG. 5 illustrates a similar schematic representation as compared to FIG. 4, but shows fewer components of the elongated access assist device 12b. For example, the embodiment shown in FIG. 5 may only include one port 31, which may serve as either the access port 24, the flush port 32, or both. Furthermore, the embodiment shown in FIG. 5 may omit a second marker band 44b. As such, in some embodiments, the elongated access assist device 12b includes only a single marker band, the first marker band 44a. The elongated access assist device 12b may not differentiate between an access port 24 and the hemostasis valve 30, and therefore only include the hemostasis valve 30, as illustrated in FIG. 5. It should also be noted that rather than being located in both the proximal portion 20 and the distal portion 22, as demonstrated in FIGS. 4 and 5, the plurality of microperforations 40 may be located in either the proximal portion 20 or the distal portion 22. In some embodiments, the plurality of microperforations 40 are coupled to at least the distal portion 22 of the elongated access assist device 12. Embodiments of the elongated access assist device 12 showing the plurality of microperforations 40 in different configurations are depicted in FIGS. 6-13.

Figure 6:
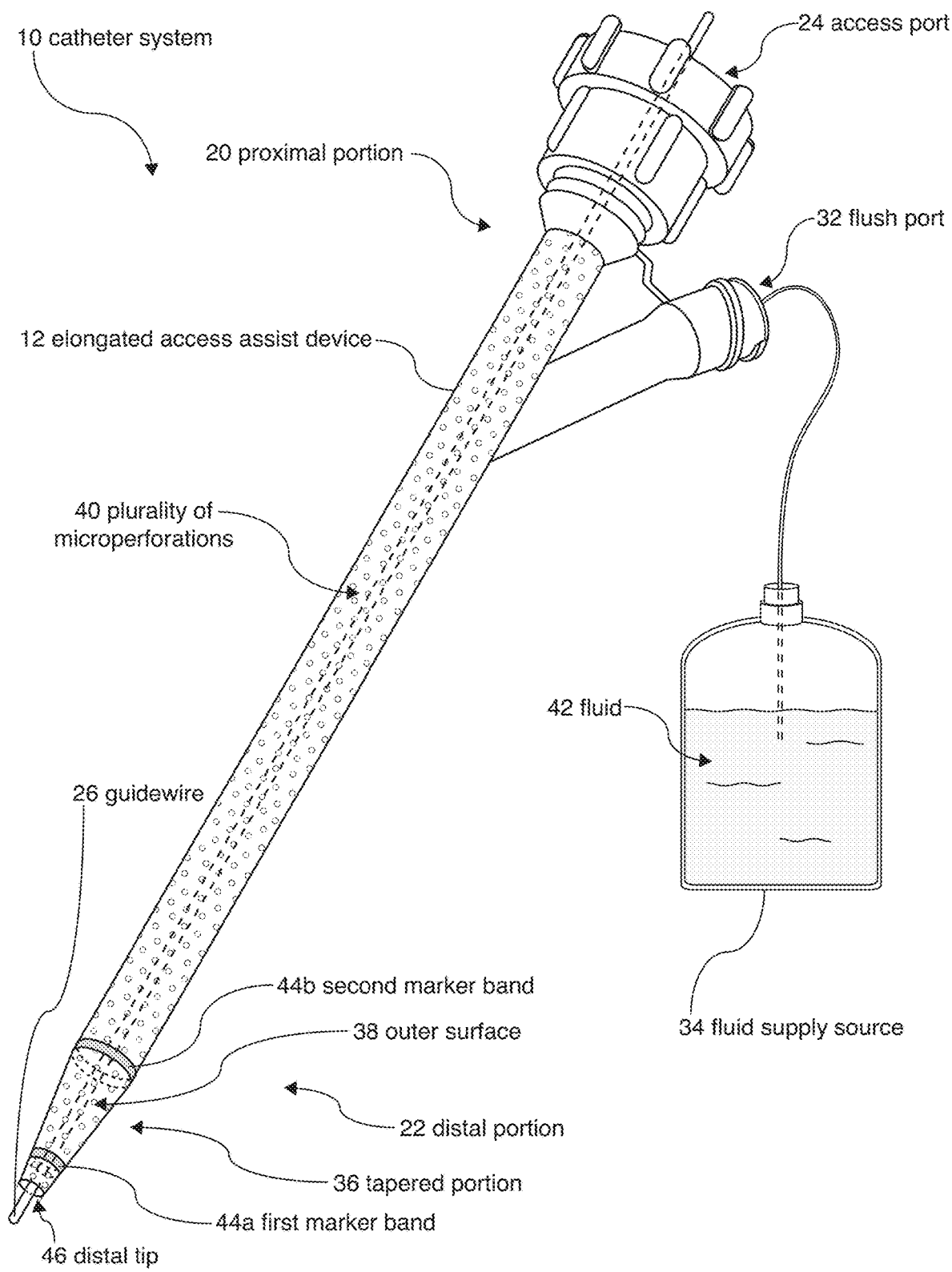
FIGS. 6, 7, 8, 9, 10, 11, 12, and 13 illustrate perspective views of a catheter system including a plurality of microperforations, according to some embodiments.

Referring now to FIG. 6, an embodiment of the catheter system 10 is shown. As illustrated, the system 10 may include an elongated access assist device 12 comprising a proximal portion 20 and a distal portion 22 located opposite the proximal portion 20. Though illustrated as unequal lengths, the proximal portion 20 may be the proximal half of the elongated access assist device 12 comprising approximately 50% of the length, and the distal portion 22 may be the distal half of the elongated access assist device 12 comprising approximately 50% of the length. In some embodiments, as shown in FIG. 6, the proximal portion 20 comprises less than half (e.g., 1% to 49%) of the working length of the elongated access assist device 12. As well, in some embodiments, the proximal portion 20 may comprise more than half (e.g., 51% to 99%) of the working length of the elongated access assist device 12. Accordingly, in some embodiments, the distal portion 22 comprises less than half (e.g., 1% to 49%) of the working length of the elongated access assist device 12. And in some embodiments, the distal portion 22 comprises more than half (e.g., 51% to 99%) of the working length of the elongated access assist device 12.

In some embodiments, the proximal portion 20 includes the access port 24 and the flush port 32. As previously stated, the access port 24 may comprise a hemostasis valve 30. As such, the proximal portion 20 may also include the hemostasis valve 30. In some embodiments, the distal portion 22 includes the tapered portion 36, the distal tip 46, the first marker band 44a, and the second marker band 44b. The guidewire 26 may be configured to extend from the access port 24 to the distal tip 46, and through the distal port 28, as shown in FIG. 2. In some embodiments, the elongated access assist device 12 comprises a guidewire lumen extending between the proximal end 14 and the distal end 16, wherein the guidewire lumen is configured to receive the guidewire 26. The guidewire lumen will be discussed in greater detail later in the disclosure.

FIGS. 6-13 show the fluid supply source 34 coupled to the flush port 32. The fluid supply source 34 may be coupled to the flush port 32 via numerous mechanisms, including a threadable coupling, a heat bonded coupling, a friction fit, and/or the like. In many embodiments, the fluid supply source 34 is detachably coupled to the flush port 32. The fluid supply source 34 may fixedly couple to the flush port 32. In some embodiments, the fluid supply source 34 is configured to couple to the access port 24, rather than the flush port 32. The fluid supply source 34 may be configured to couple to both the access port 24 and the flush port 32. The fluid supply source 34 may couple to both the access port 24 and the flush port 32 substantially simultaneously. In many embodiments, the fluid 42 of the fluid supply source 34 comprises at least one of saline, contrast dye, any type of bioabsorbable media, and the like. The fluid 42 may comprise another substance used in thrombectomy procedures, such as a lytic agent. In some embodiments, the fluid 42 is released from the fluid supply source 34 and through the flush port 32 into the elongated access assist device 12 in a substantially continuous manner. The fluid 42 may be released in a controlled and/or restricted manner. In some embodiments, the fluid 42 is released in a passive manner. At least one of the flush port 32 and the fluid supply source 34 may include a mechanism to control the flow of fluid, such as a pressure-activated valve.

Figure 7:
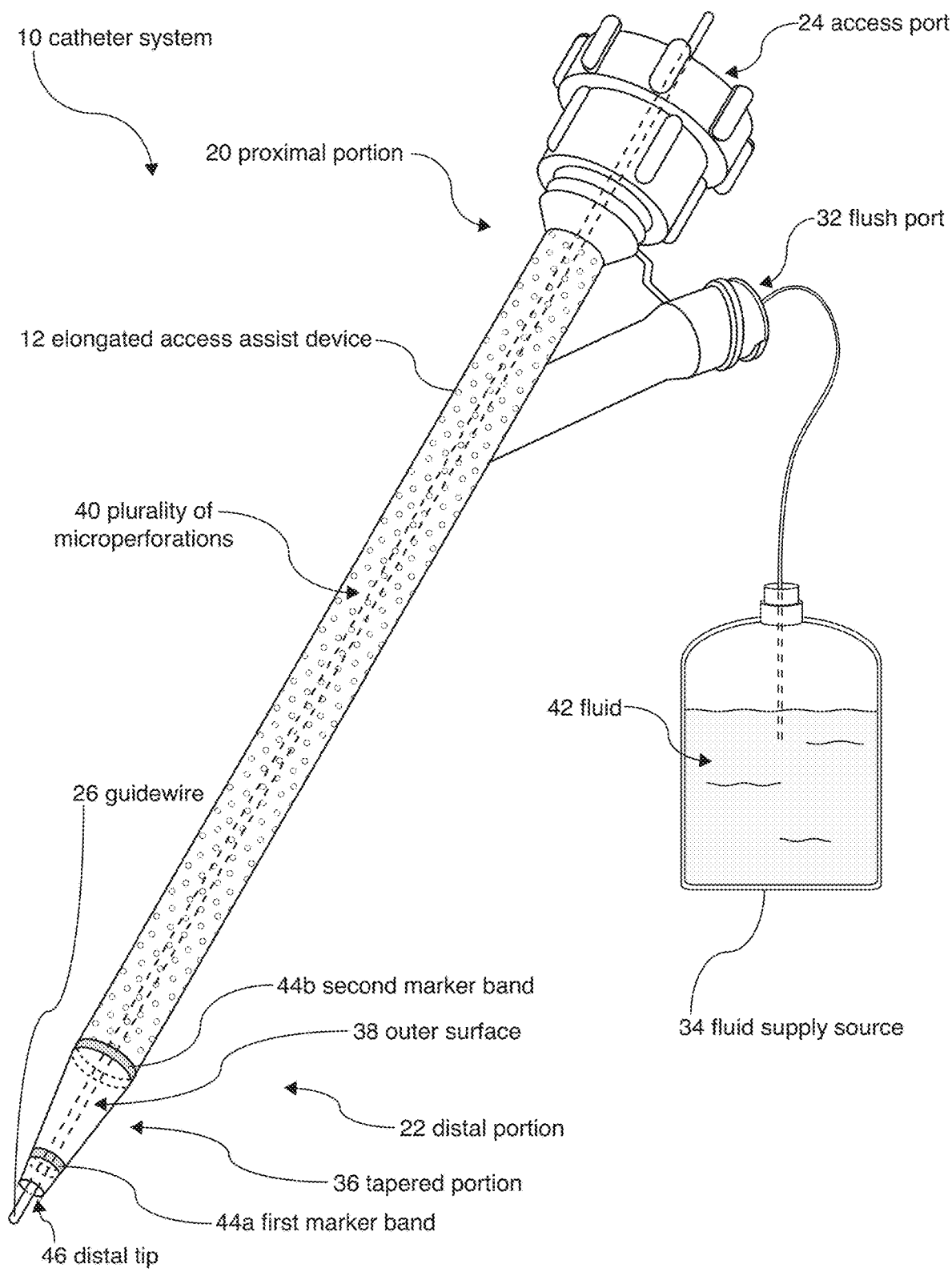
Figure 8:
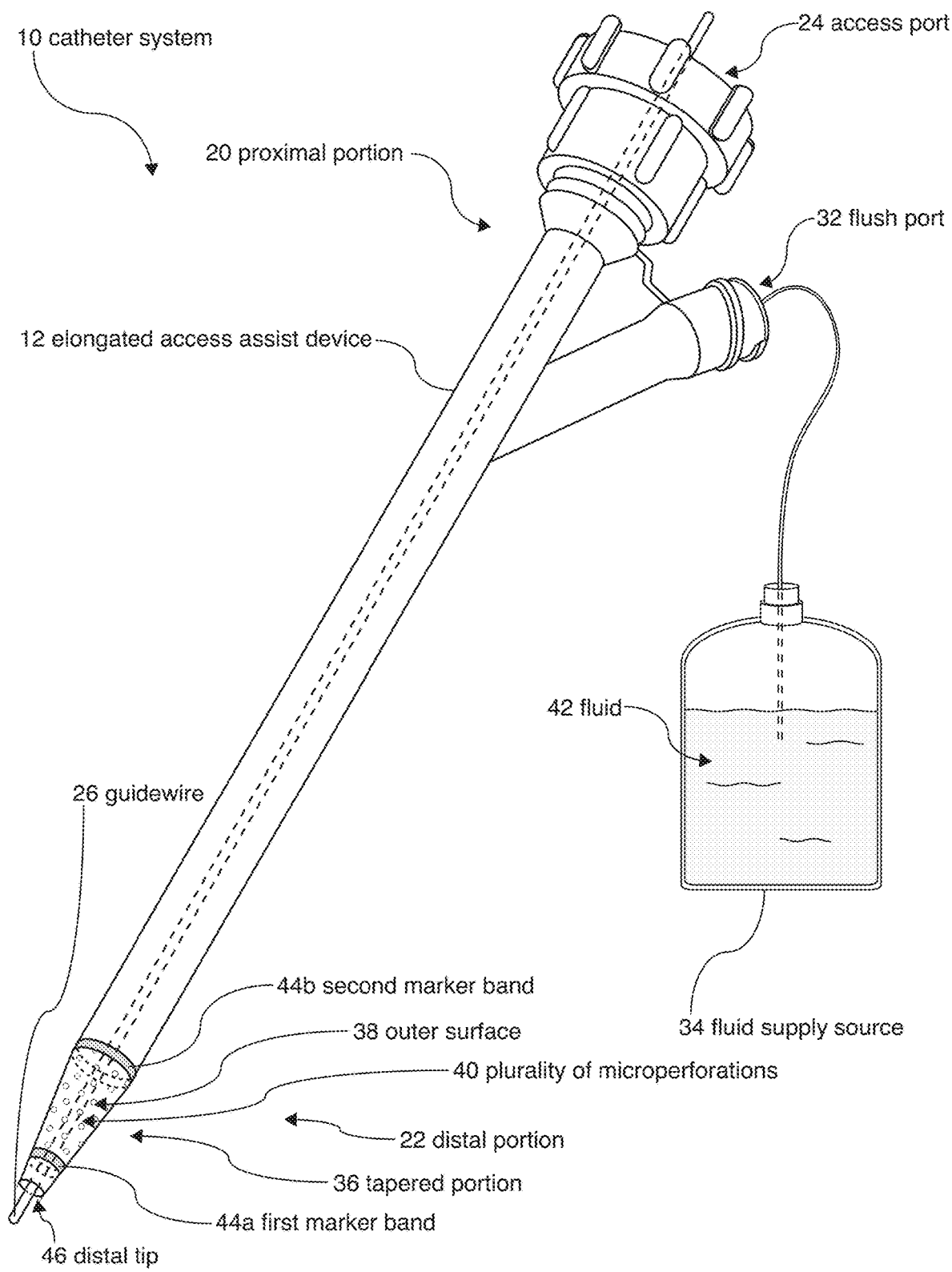
Figure 9:
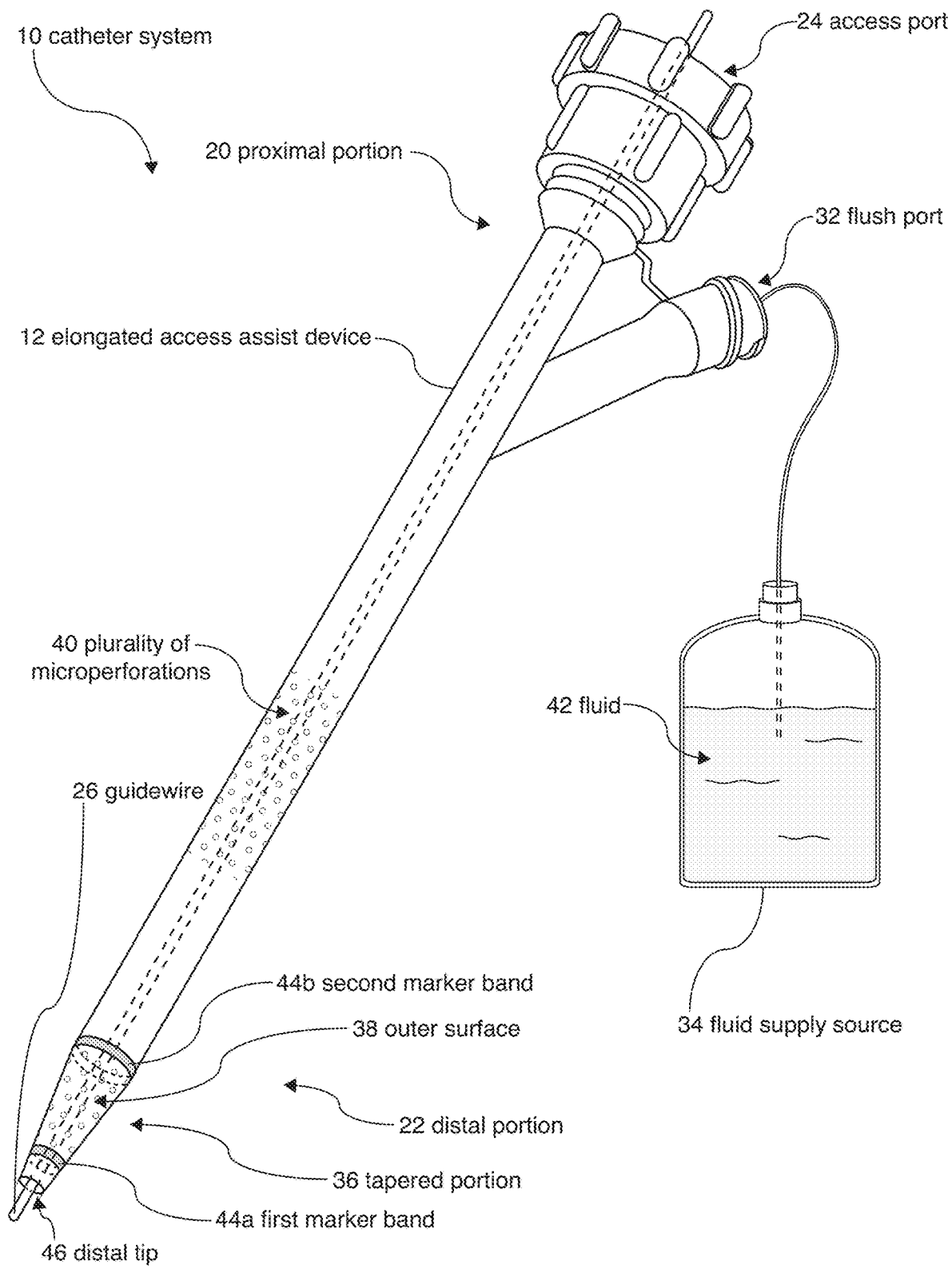
Figure 10:
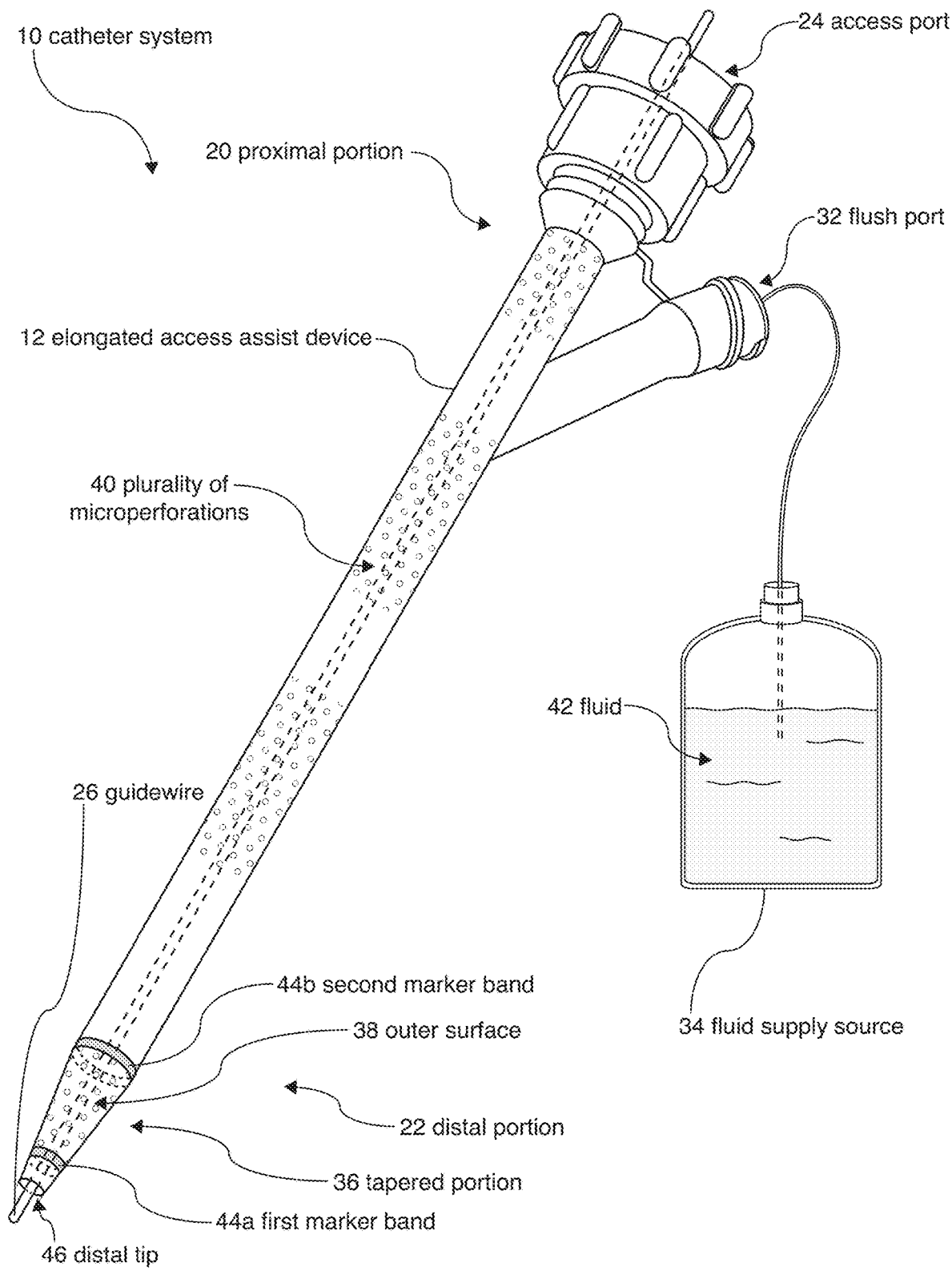
Figure 11:
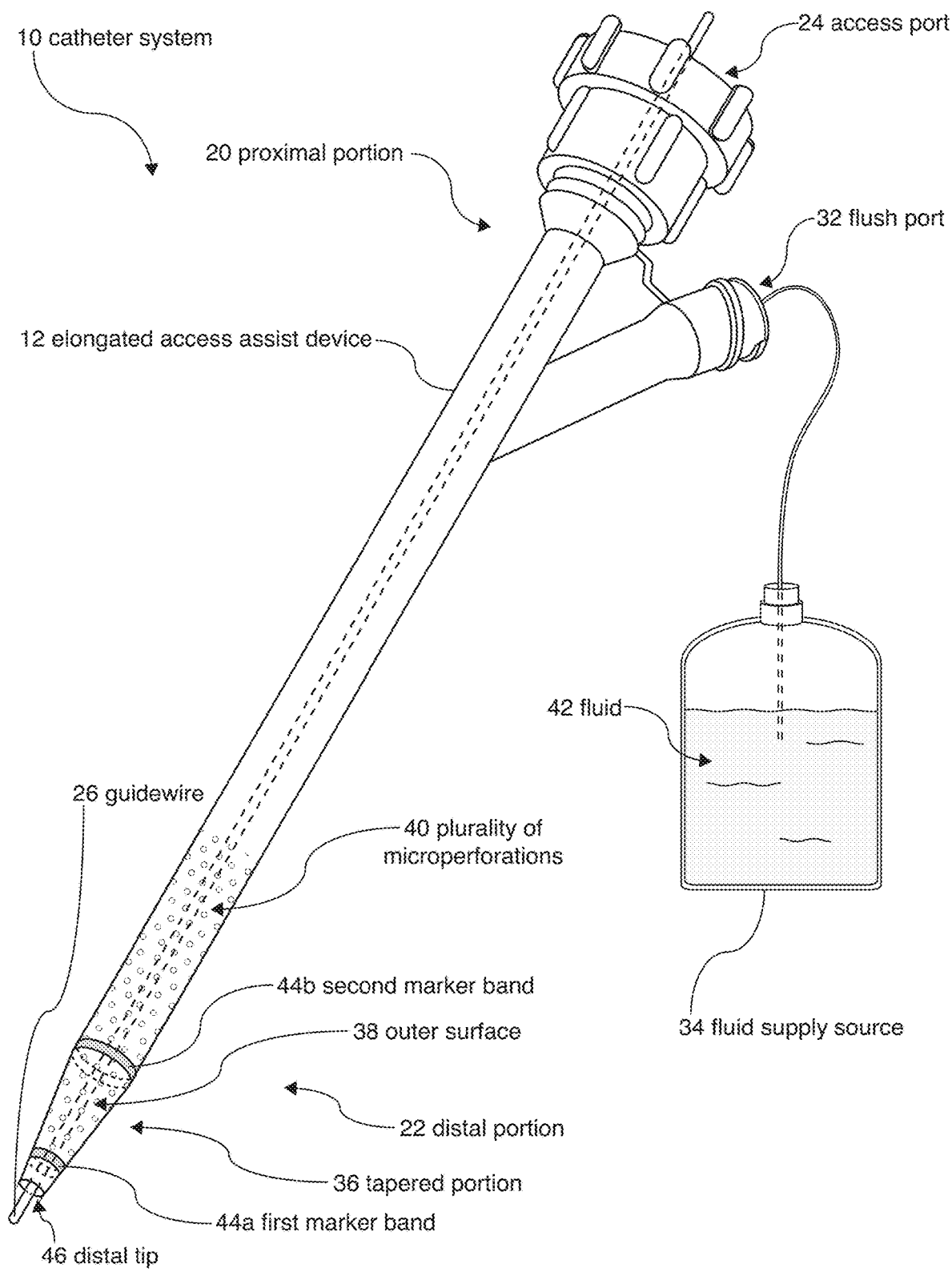
Figure 12:
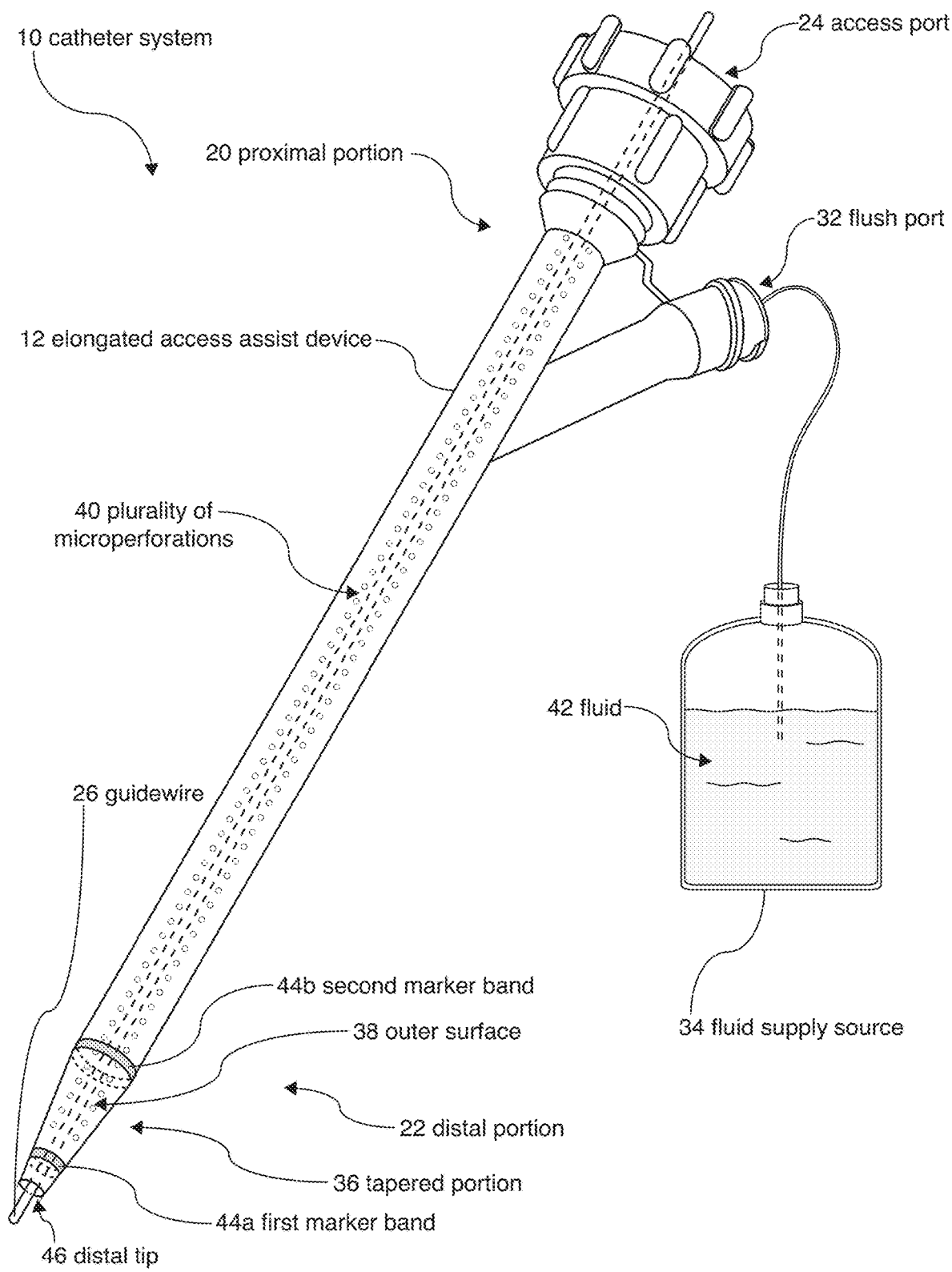
Figure 13:
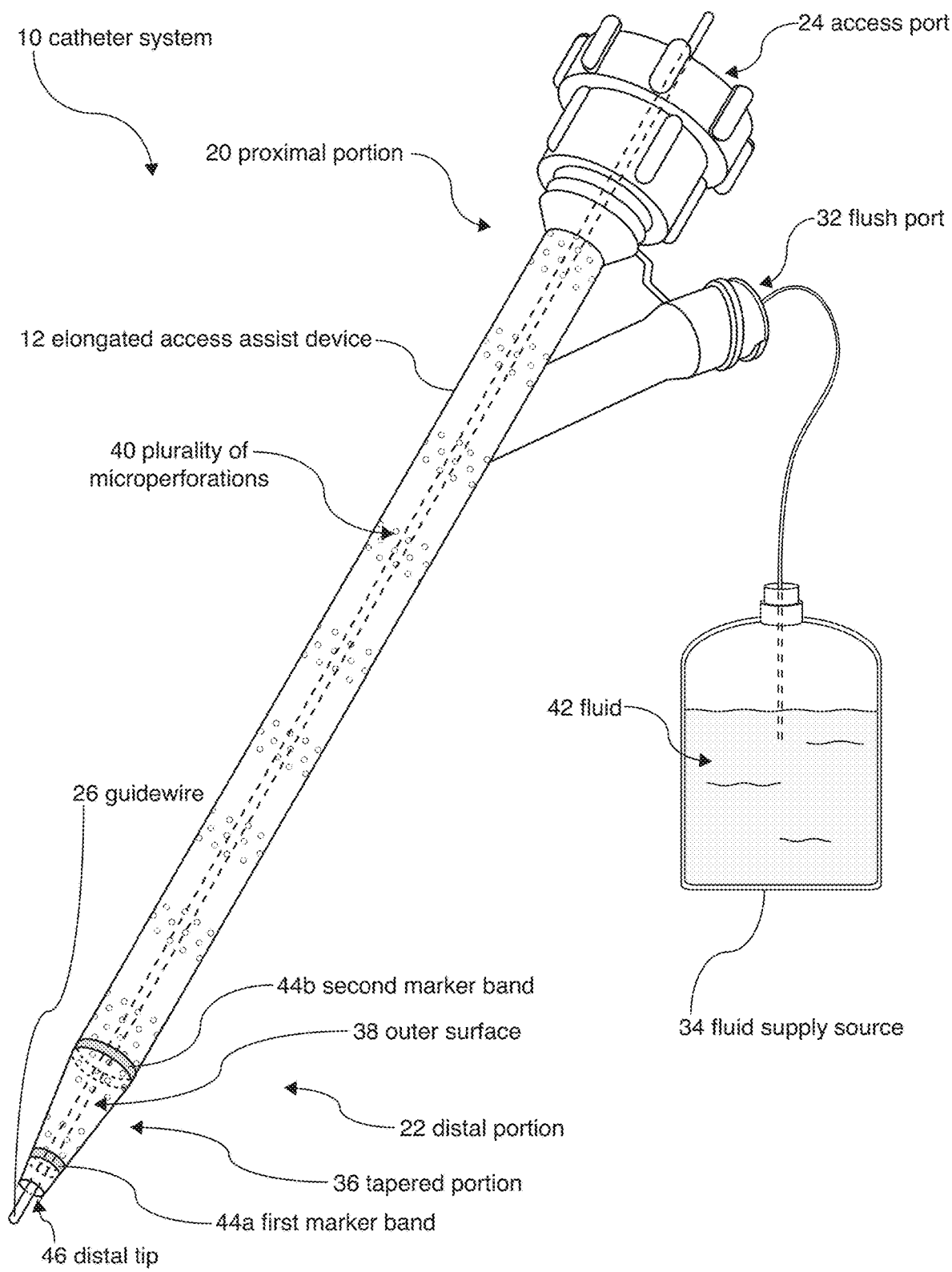

As discussed with reference to FIGS. 4 and 5, and as illustrated in FIG. 6, the plurality of microperforations 40 may be located on both the proximal portion 20 and the distal portion 22. As also illustrated in FIG. 6, the plurality of microperforations 40 may be located on both the body and the tapered portion 36 of the elongated access assist device 12. As illustrated in FIG. 7, the plurality of microperforations 40 may be located only on the body of the elongated access assist device 12. In some embodiments, as shown in FIG. 8, the plurality of microperforations 40 are located only on the tapered portion 36. The plurality of microperforations 40 may be substantially evenly spaced and dispersed across the tapered portion 36. FIG. 9 illustrates that the plurality of microperforations 40 may be located in two distinct areas of the elongated access assist device 12, such as on the tapered portion 36 and another area on the body of the device 12, as shown. In some embodiments, as demonstrated by FIG. 10, the plurality of microperforations 40 are located in more than two distinct areas of the elongated access assist device 12. FIG. 11 illustrates that the plurality of microperforations 40 may be located on the tapered portion 36 and on part of the body of the elongated access assist device 12. FIG. 11 shows the plurality of microperforations 40 extending proximally from the tapered portion 36, but still on the distal portion 22 of the device 12, such that the plurality of microperforations 40 cover a continuous section of the device 12, rather than two distinct areas, as shown in FIG. 9. In some embodiments, as illustrated in FIG. 12, the plurality of microperforations 40 extend along the elongated access assist device 12 in at least one substantially straight line. FIG. 13 shows that the plurality of microperforations 40 may extend along the elongated access assist device 12 in small clusters, rather than a straight line or even dispersion.

It should be noted that the embodiments shown in FIGS. 6-13 include only some of the possible arrangements of the plurality of microperforations 40 on the elongated access assist device 12. Other arrangements may include: a single straight line of microperforations, a wavy line of microperforations, multiple wavy lines of microperforations, a corkscrew spiral of microperforations, microperforations on only a portion of the tapered portion 36, microperforations on only a portion of the body of the device 12, microperforations on only one side of the device 12, unevenly dispersed microperforations, and any number of other possible arrangements and/or combinations therein. The elongated access assist device 12 may include no microperforations. In many embodiments, each microperforation of the plurality of microperforations 40 defines a shape and/or size similar to a pinhole. Each microperforation may define any other suitable shape, such as triangular, rectangular, ovoid, and the like.

In many embodiments, the plurality of microperforations 40 are configured to facilitate a substantially continuous release (i.e., perfusion) of fluid 42. The release of fluid 42 may further aid in navigation through tortuous anatomy by reducing friction between the vasculature and the elongated access assist device 12. As previously discussed, in many embodiments, the elongated access assist device 12 is configured to be slideably received by a primary device, such as a neurovascular sheath or aspiration catheter. The plurality of microperforations 40, with the associated perfusion of saline or another fluid 42, may also reduce friction between the device 12 and the primary device, particularly during insertion and/or removal of the elongated access assist device 12 from the primary device, and vice versa.

Figure 14:
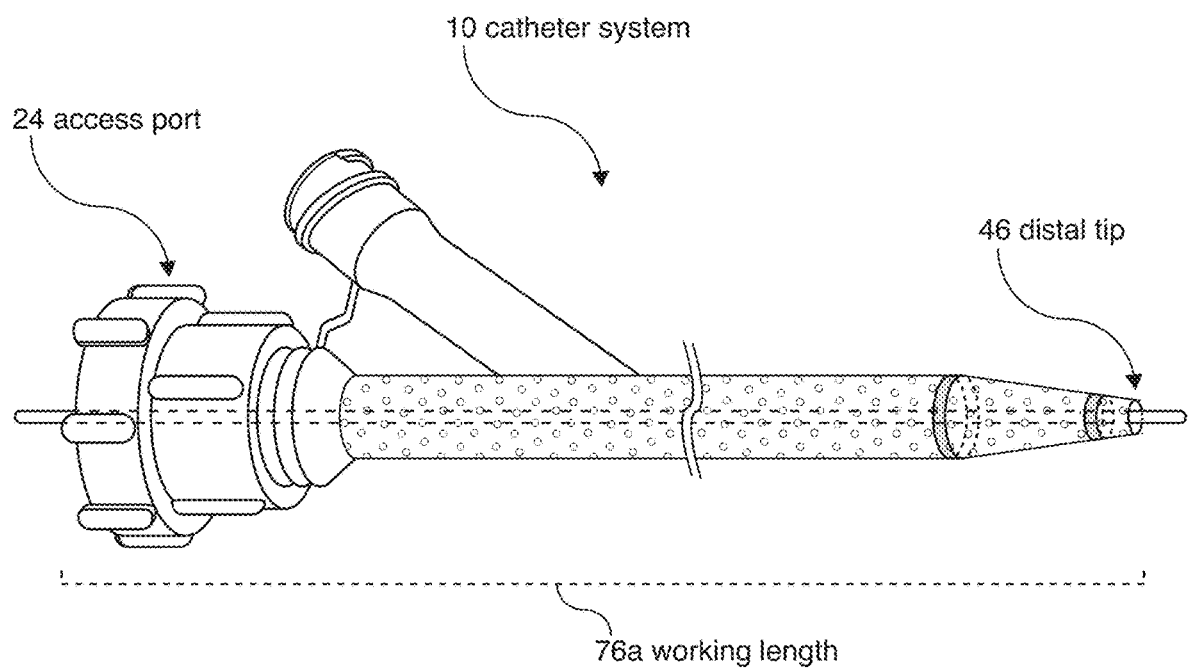
FIGS. 14 and 15 illustrate perspective views of a working length of a catheter system, according to some embodiments.
Figure 15:
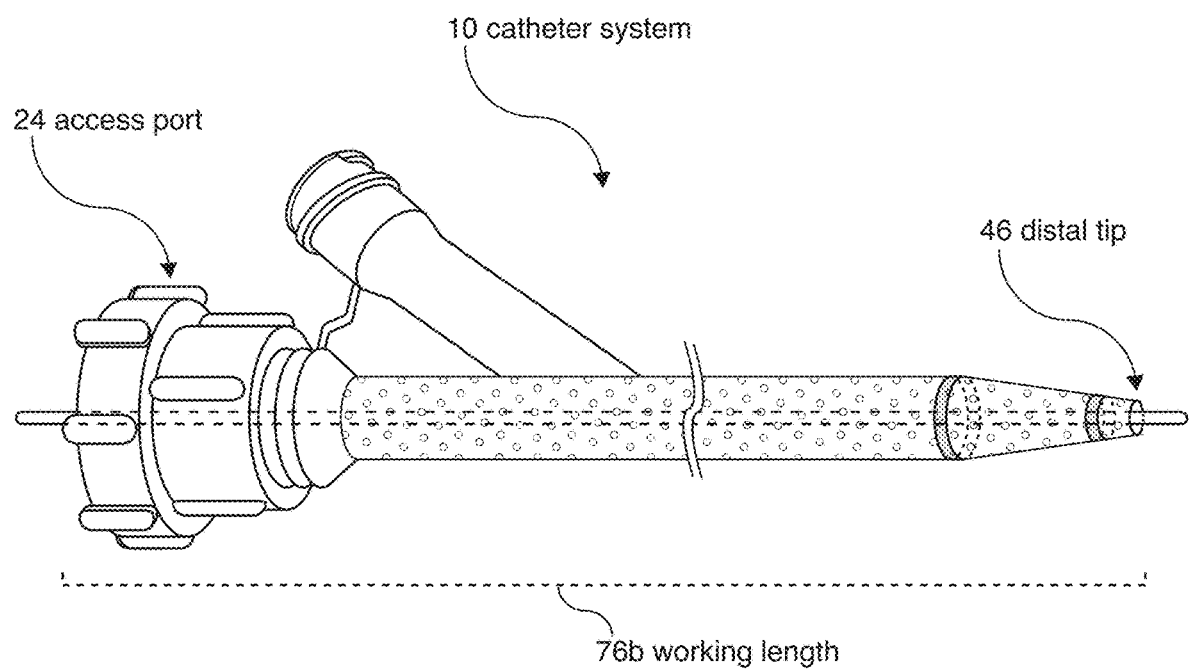

Referring now to FIGS. 14 and 15, two embodiments of the catheter system 10 are shown. As indicated in FIG. 14, the system 10 may define a working length 76a. FIG. 15 shows that the system 10 may define a working length 76b that is different from the working length 76a. The following table includes some possibilities for working lengths, but is intended to be nonlimiting. The system 10 may define a working length not included in the following table. In addition, the following example lengths may be considered approximate lengths. For example, the provided length of 81 cm may be considered "about" 81 cm. As such, a working length between 80 cm and 82 cm may be considered "about" 81 cm. It should be noted that "working length" is intended to define the length of the elongated access assist device 12 from the access port 24 to the distal tip 46.

| Possible Working Lengths |
| --- |
| 81 cm |
| 91 cm |
| 106 cm |
| 130 cm |
| 133 cm |
| 150 cm |
| 160 cm |

Figure 16:
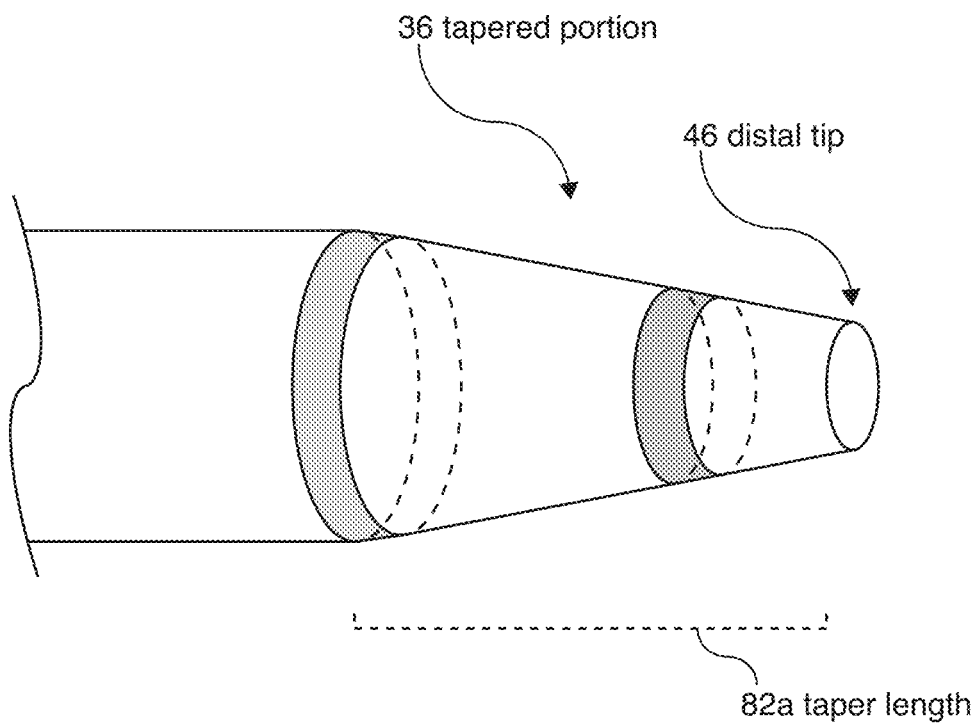
FIGS. 16 and 17 illustrate perspective views of a taper length of a tapered portion of an elongated access assist device, according to some embodiments.
Figure 17:
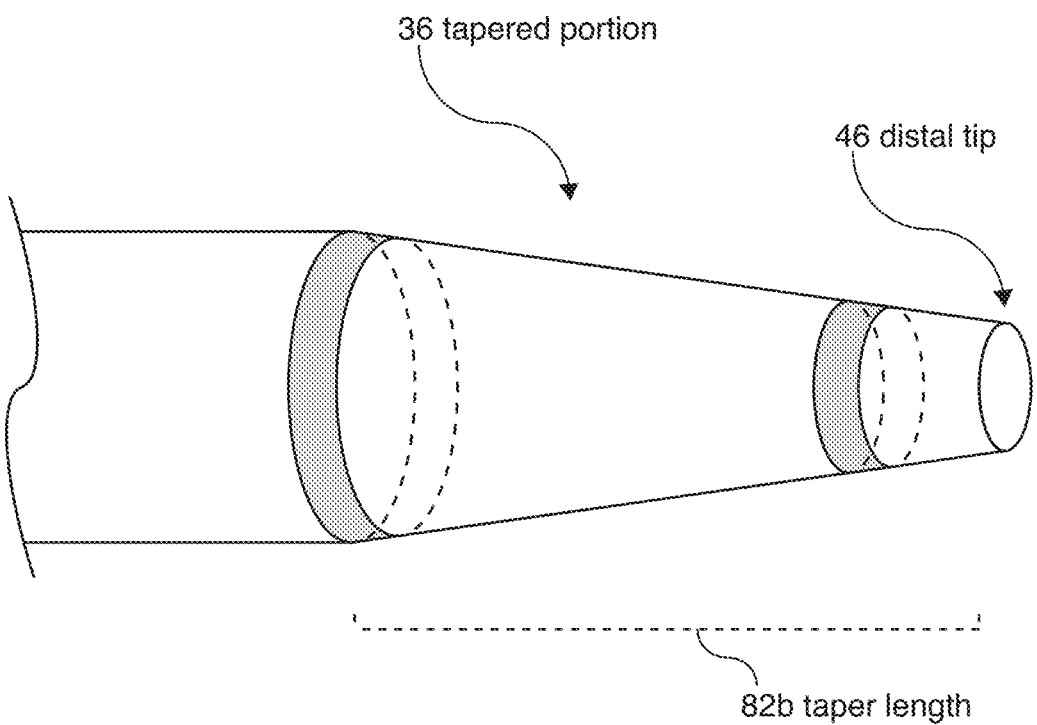

FIGS. 16 and 17 show different embodiments of the tapered portion 36 of the elongated access assist device 12. FIG. 16 illustrates an embodiment with a taper length 82a, while FIG. 17 illustrates an embodiment with a taper length 82b. As shown, the taper length 82a may define a shorter length than the taper length 82b. Similar to the working lengths, the following table includes some possibilities for taper lengths, but is intended to be nonlimiting. The tapered portion 36 may define a taper length not included in the following table. In addition, the following example lengths may be considered approximate lengths. For example, the provided length of 5 cm may be considered "about" 5 cm. As such, a taper length between 4.75 cm and 5.25 cm may be considered "about" 5 cm. The tapered portion 36 may define at least part of the distal portion 22, and generally comprises less than half of the elongated access assist device 12. In many embodiments, the taper length 82a, 82b is limited to a shorter length (e.g., 1-5 cm). A longer taper extends further from the primary device, and may be more difficult to control and navigate through the vasculature. A relatively short taper length 82a, 82b may provide the ideal balance between having the smooth transition created by the tapered portion 36, while still remaining close to the distal edge of the primary device and thus having the supportive structure and "pushing power" of the primary device.

| Possible Taper Lengths |
| --- |
| 1 cm |
| 2 cm |
| 5 cm |
| 10 cm |
| 20 cm |

Figure 18:
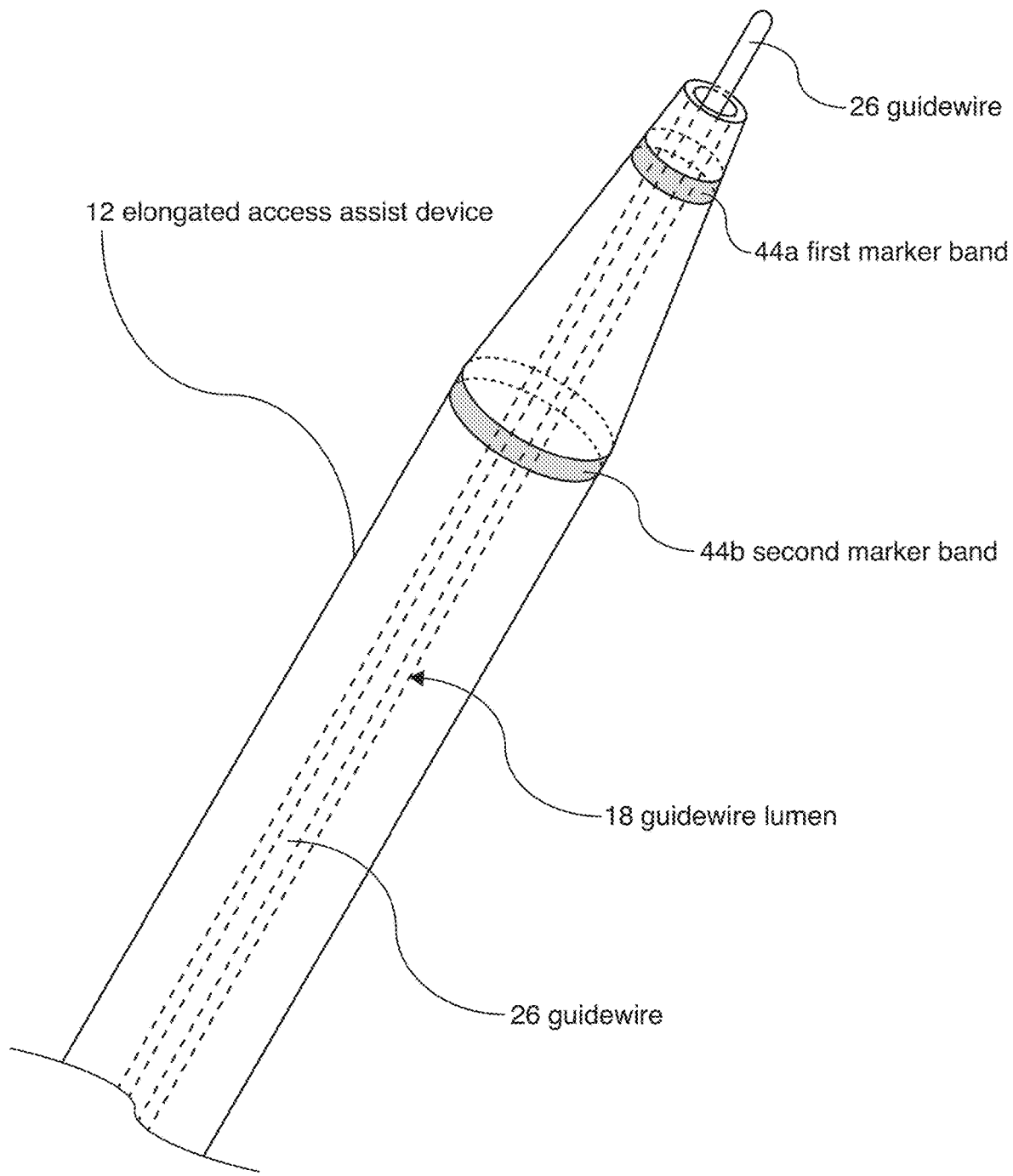
FIG. 18 illustrates a perspective view of an elongated access assist device including a guidewire lumen, according to some embodiments.

FIG. 18 illustrates an embodiment of the elongated access assist device 12 including a guidewire lumen 18. As discussed with reference to FIG. 6, the elongated access assist device 12 may comprise a guidewire lumen 18 extending between the proximal end 14 and the distal end 16, wherein the guidewire lumen 18 is configured to receive the guidewire 26. In many embodiments, the guidewire lumen 18 is substantially centered within the elongated access assist device 12. The guidewire lumen 18 may be located off-center, such that it is closer to one side of the elongated access assist device 12 than another (i.e., asymmetric). In some embodiments, the guidewire lumen 18 defines a constant diameter. The guidewire lumen 18 may define a varying diameter; for example, the guidewire lumen 18 may taper in a manner similar to the elongated access assist device 12.

The following table includes some example inner diameters of the guidewire lumen 18, as well as the corresponding guidewire 26 outer diameters. It should be noted that, similar to the two tables above, the listed values represent only a few examples and are intended to be nonlimiting. At least one of the guidewire 26 and the guidewire lumen 18 may define diameters not included in the table. In addition, each size guidewire 26 is not limited to a specific size of guidewire lumen 18. For example, a 0.014" guidewire 26 may be configured to be received by a 0.016" lumen 18, a 0.018" lumen 18, or a 0.02" lumen 18.

| Guidewire OD | Guidewire Lumen ID |
| --- | --- |
| 0.018" | 0.02" |
| 0.016" | 0.018" |
| 0.014" | 0.016" |

Figure 19:
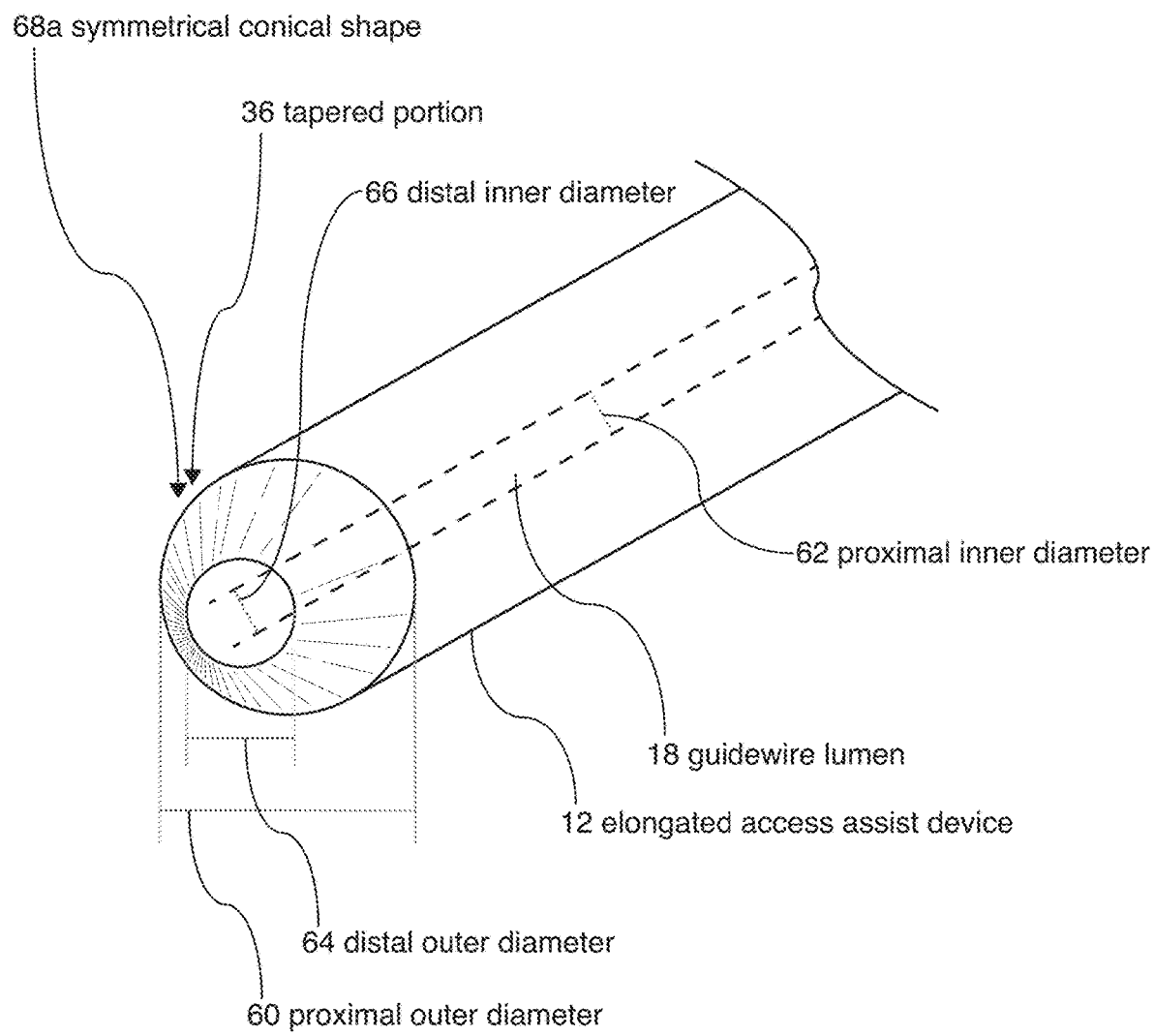
FIGS. 19 and 20 illustrate front perspective views of an elongated access assist device, according to some embodiments.

FIG. 19 illustrates a front perspective view of the elongated access assist device 12, including the guidewire lumen 18. FIG. 19 also shows an embodiment where the guidewire lumen 18 is tapered, as indicated by the difference seen between the proximal inner diameter 62 and the distal inner diameter 66. In some embodiments, the proximal inner diameter 62 is the inner diameter of the guidewire lumen 18 throughout the body of the elongated access assist device 12. The distal inner diameter 66 may be the inner diameter of the guidewire lumen 18 at the distal-most portion of the tapered portion 36; for example, at the distal tip 46 and/or distal port 28. FIG. 19 also includes the proximal outer diameter 60 and the distal outer diameter 64. Similar to the proximal inner diameter 62, the proximal outer diameter 60 may be considered the outer diameter of the elongated access assist device 12 throughout the non-tapered body portion of the device 12. The distal outer diameter 64 may be considered the outer diameter at the distal tip 46 and/or distal port 28. In some embodiments, the distal outer diameter 64 is 0.023" and the distal inner diameter 66 is 0.018". The proximal inner diameter 62 may be 0.02", and the proximal outer diameter 60 may be 0.068". Each of the listed diameters is included by way of example only, and the disclosed invention is not in any way limited to the stated diameters.

Figure 20:
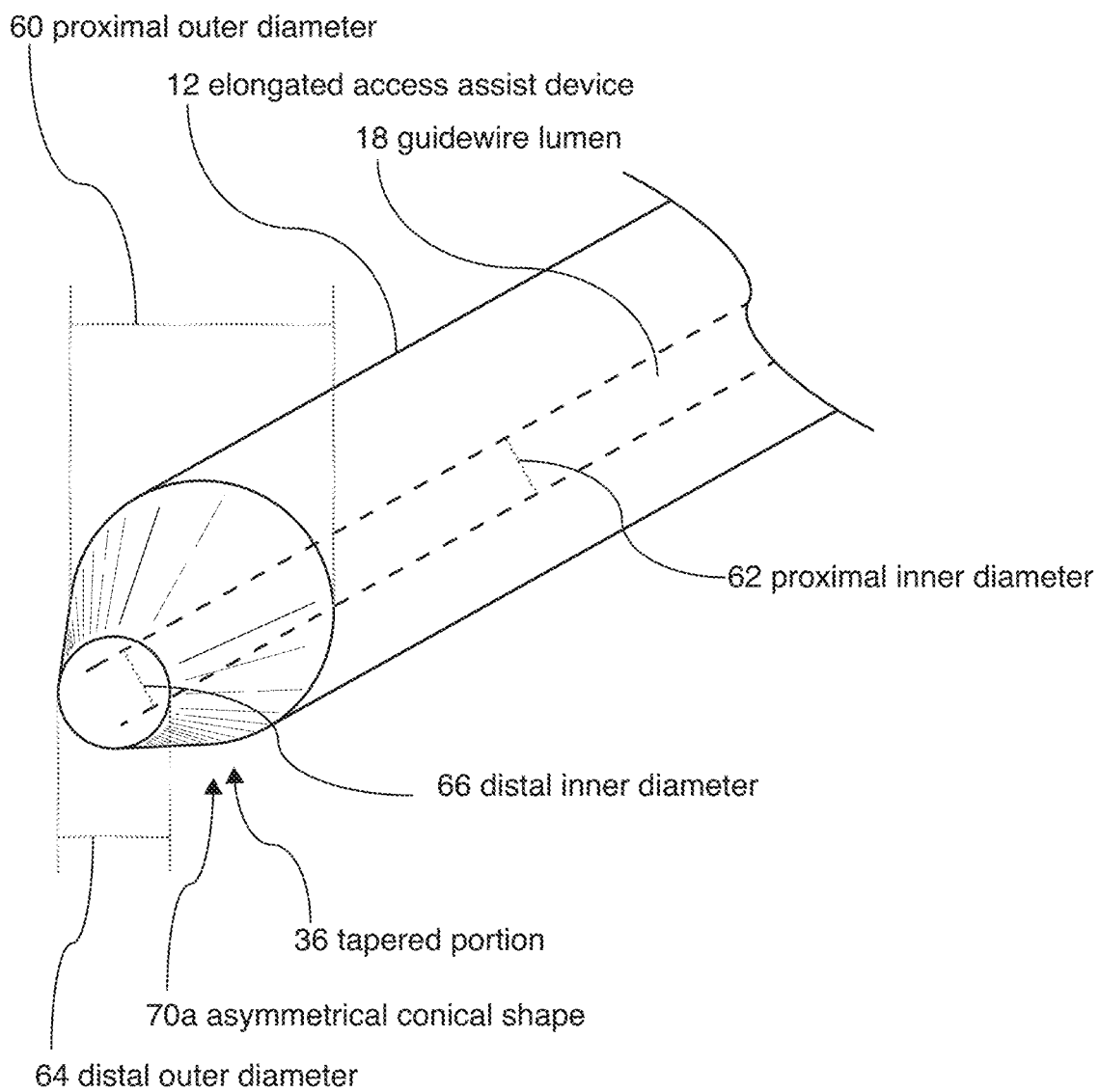
Figure 21:
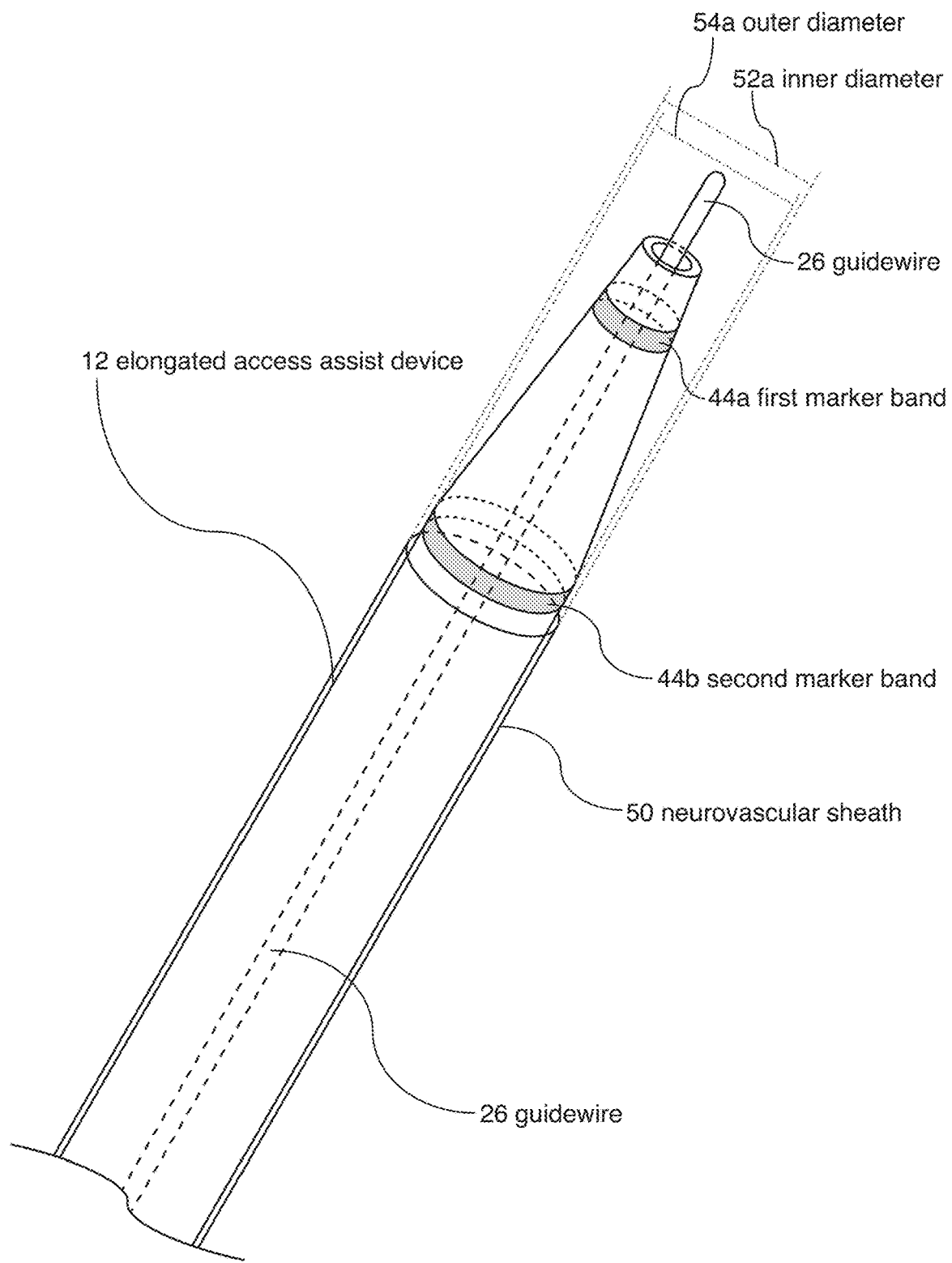
FIGS. 21, 22, and 23 illustrate perspective views of a neurovascular sheath tracked over an elongated access assist device, according to some embodiments.
Figure 22:
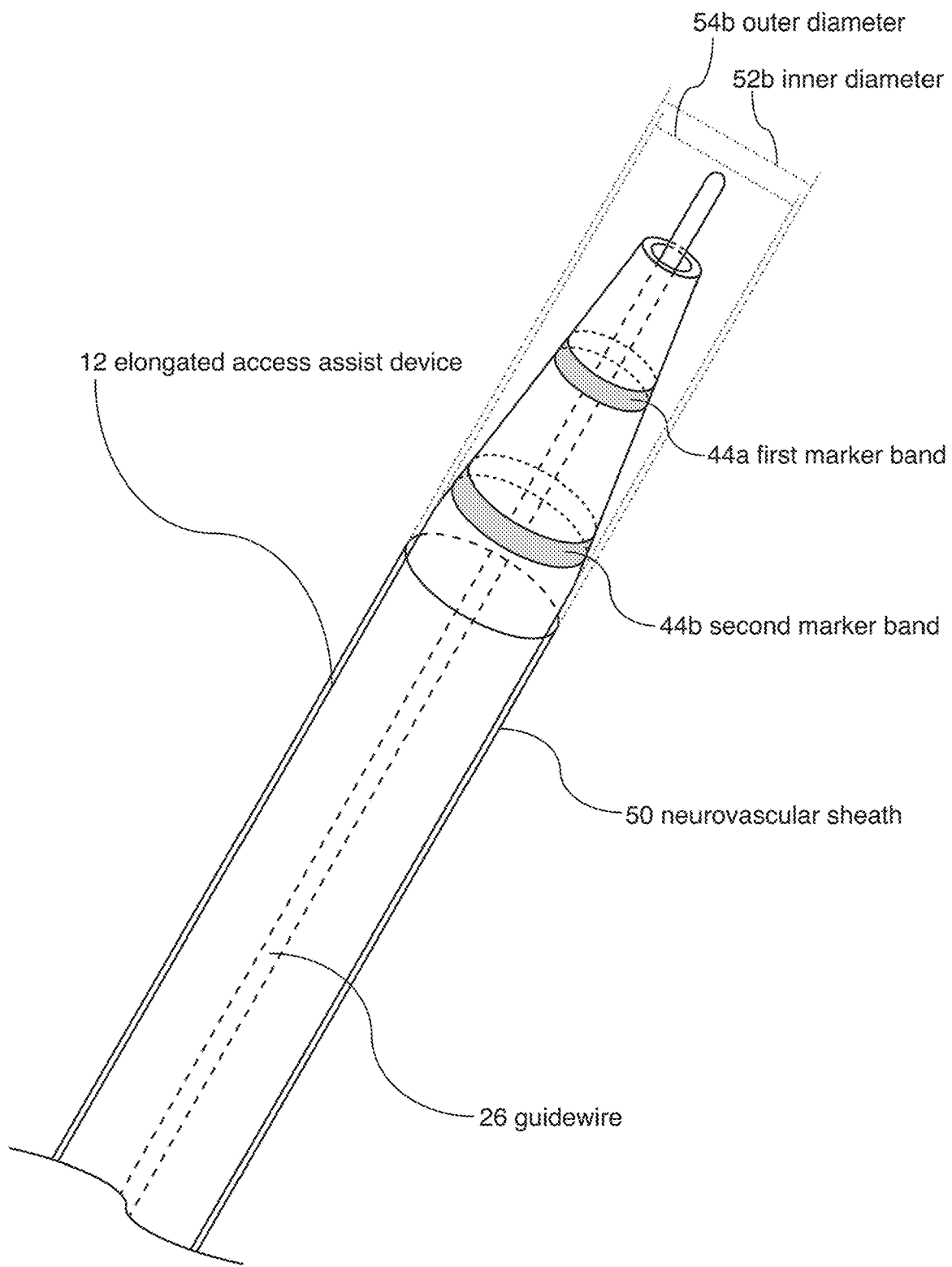

FIG. 19 also indicates that the drawing shows a symmetrical conical shape 68a of the tapered portion 36. FIG. 20 is similar to FIG. 19, but shows that the tapered portion 36 defines an asymmetrical conical shape 70a. The embodiment illustrated in FIG. 20 may include similar, the same, or different diameters for the proximal outer diameter 60, the proximal inner diameter 62, the distal outer diameter 64, and/or the distal inner diameter 66. The symmetrical and asymmetrical conical shapes 68a, 70a will be discussed in greater detail later in the disclosure. FIG. 21 illustrates the concept of the elongated access assist device 12 used in conjunction with a primary device, such as a neurovascular sheath 50. The primary device may be a device other than a neurovascular sheath 50, such as, but not limited to, a neurovascular aspiration catheter (shown in FIGS. 24-26), a neurovascular distal access catheter, and/or a neurovascular guidecatheter. As previously discussed, in many embodiments, the elongated access assist device 12 is placed through the primary device, and is configured to extend beyond the distal edge of the primary device, as shown in FIGS. 21 and 22. At least the tapered portion 36 of the elongated access assist device 12 may be configured to extend beyond the distal edge of the primary device.

In many embodiments, the elongated access assist device 12 defines an outer diameter 54a and the neurovascular sheath 50 defines an inner diameter 52a, as shown in FIG. 21. In order to maximize support of the neurovascular sheath 50 by the elongated access assist device 12, and to minimize the shelf effect created by the gap between the outer diameter 54a and the inner diameter 52a, it may be ideal to reduce the size of the gap. For example, in many embodiments, the outer diameter 54a of the elongated access assist device 12 may define a diameter that comprises about 90% of the inner diameter 52a of the neurovascular sheath 50. The following table presents some example outer diameters for the elongated access assist device 12 and inner diameters for a primary device. As with the previous tables, the values are included by way of example only and are intended to be nonlimiting. It should be noted, as indicated below the table, that the values in the table are calculated based on embodiments where the outer diameter of the elongated access assist device 12 is 90% of the inner diameter of the primary device. In some embodiments, the outer diameter encompasses a percentage other than 90% of the inner diameter. For example, the outer diameter may be 85%, 95%, 97%, 99%, etc. of the inner diameter.

| OD Access Assist Device | ID Primary Device* |
|---|---|
| 0.08" | 0.089" |
| 0.079" | 0.088" |
| 0.071" | 0.079" |
| 0.068" | 0.076" |
| 0.065" | 0.072" |
| 0.064" | 0.071" |
| 0.061" | 0.068" |
| 0.057" | 0.063" |
| 0.054" | 0.06" |
| 0.049 | 0.054" |
| 0.032" | 0.035" |
| 0.024" | 0.027" |
| 0.023" | 0.025" |

*based on OD of access device = 90% of ID of primary device

FIG. 21 also includes the first marker band 44a and the second marker band 44b. In many embodiments, as illustrated in FIG. 21, the first marker band 44a is located adjacent the distal port 28 of the elongated access assist device 12, and the second marker band 44b is located substantially immediately proximal to the tapered portion 36. As such, the second marker band 44b may be considered an indicator of the "beginning," when moving in a distal direction, of the tapered portion 36. The first marker band 44a may also be considered coupled to the distal tip 46 of the tapered portion 36, and the second marker band 44b may be considered coupled to the elongated access assist device 12 proximal to the tapered portion 36. In many embodiments, both the first marker band 44a and the second marker band 44b comprise a radiopaque material. The first and second marker bands 44a, 44b will be discussed further with reference to FIGS. 34-47.

FIG. 22 shows a similar embodiment of the elongated access assist device 12 shown in FIG. 21, but demonstrates different placement of the first and second marker bands 44a, 44b. In the embodiment of FIG. 22, the second marker band 44b is located more distally as compared to the second marker band 44b shown in FIG. 21. As such, the second marker band 44b in FIG. 22 is located further "down" the tapered portion 36, and may not serve as an indication of the "beginning" of the tapered portion 36. In contrast, the first marker band 44a is located more proximally as compared to the first marker band 44a shown in FIG. 21. As such, FIG. 22 shows that, in some embodiments, the first marker band 44a is slightly further removed from the distal tip 46 of the elongated access assist device 12. The distance between the distal tip 46 and the first marker band 44a will be discussed in greater detail with reference to FIGS. 34 and 35.

In addition, FIG. 22 includes an outer diameter 54b of the elongated access assist device 12 and an inner diameter 52b of the neurovascular sheath 50. In some embodiments, the outer diameter 54b is different from the outer diameter 54a of FIG. 21, and the inner diameter 52b is different from the inner diameter 52a of FIG. 21. As a nonlimiting example, the outer diameter 54a may define 0.079" and the inner diameter 52a may define 0.088", while the outer diameter 54b may define 0.057" and the inner diameter 52b may define 0.063". In some embodiments, the outer diameter 54a and inner diameter 52a define smaller diameters than the outer diameter 54b and inner diameter 52b.

Figure 23:
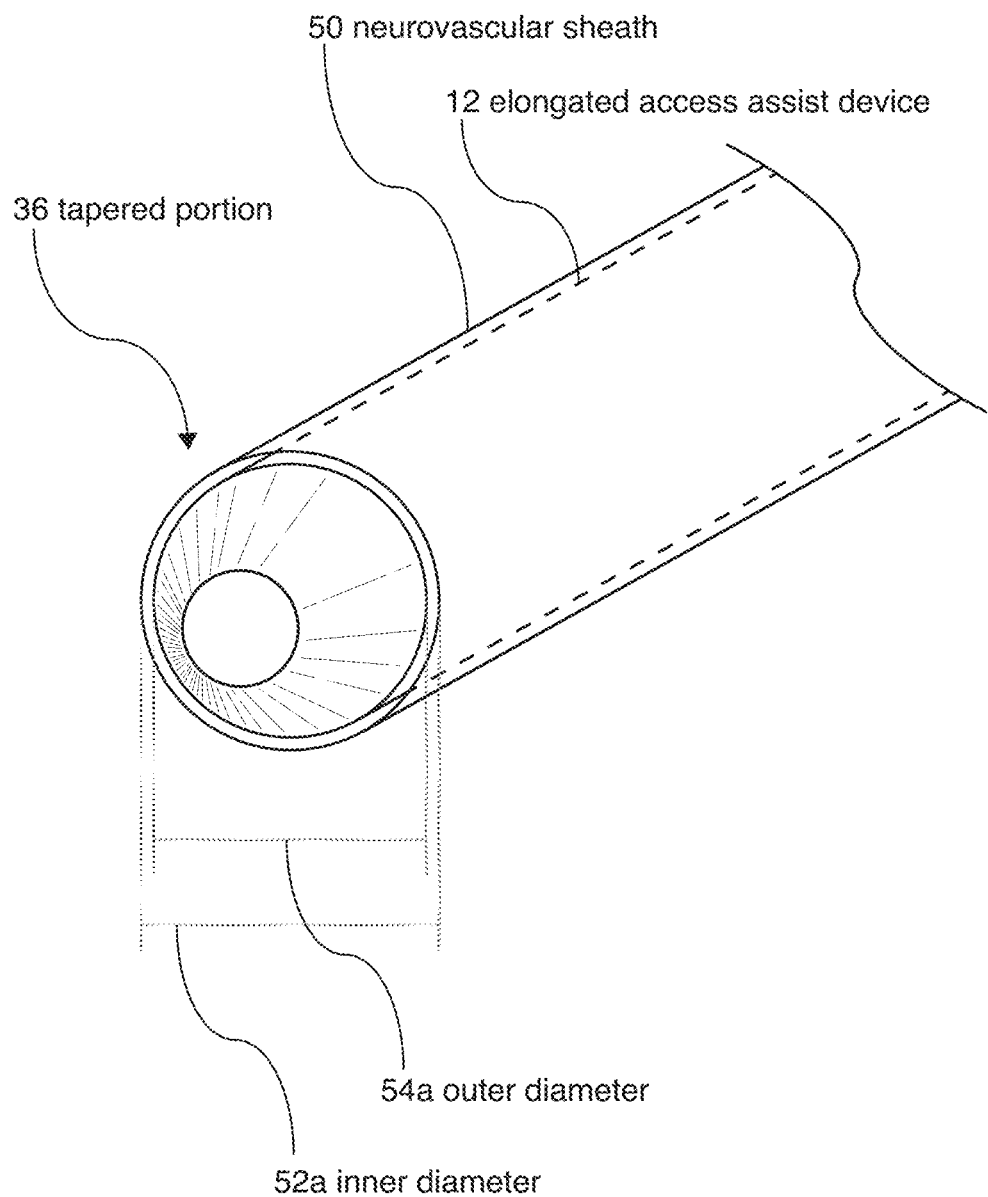

FIG. 23 shows a front perspective view, similar to FIGS. 19 and 20, of the neurovascular sheath 50 tracked over the elongated access assist device 12. FIG. 23 also demonstrates, with greater clarity, the difference between the outer diameter 54a of the elongated access assist device 12 and the inner diameter 52a of the neurovascular sheath 50. A small difference, such as the one shown in FIGS. 21-23, results in a small gap between the device 12 and the sheath 50, thereby providing a smooth transition from the tapered portion 36 of the device 12 to the neurovascular sheath 50 to reduce the shelf effect. The conical tip design of the tapered portion 36 also helps provide the smooth transition and ease navigation and trackability of the catheter system 10 through tortuous anatomy. As previously discussed, the perfusion of saline through the plurality of microperforations 40 may further ease navigation and trackability by reducing friction between the system 10 and the vasculature, and also by reducing friction between the elongated access assist device 12 and the primary device, such as the neurovascular sheath 50. It should be noted that FIG. 23 illustrates a symmetrical conical shape of the tapered portion 36, though the tapered portion 36 may define an asymmetrical conical shape. The tapered portion 36 may define a non-conical tapered shape.

Figure 24:
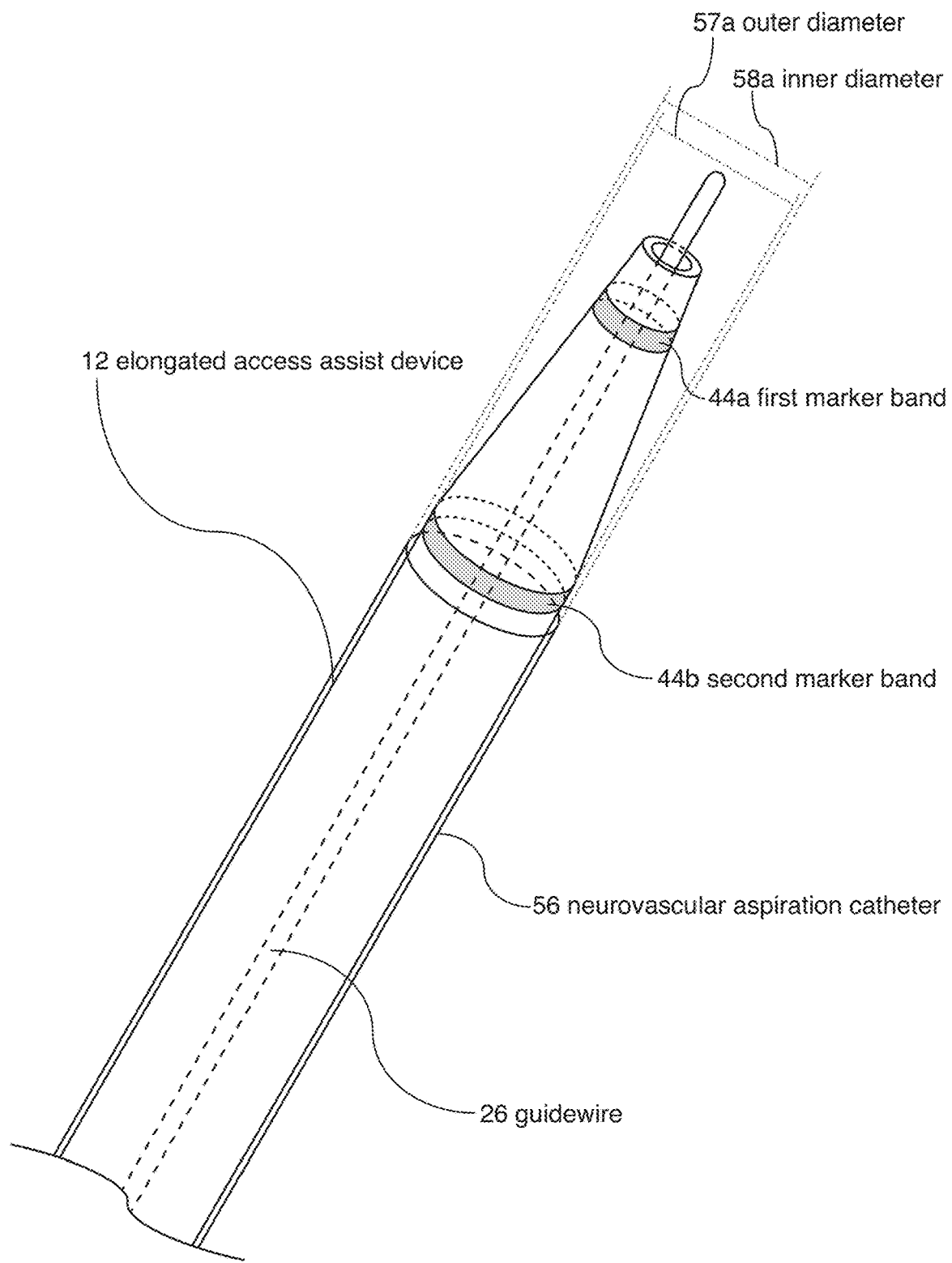
FIGS. 24, 25, and 26 illustrate perspective views of a neurovascular aspiration catheter tracked over an elongated access assist device, according to some embodiments.
Figure 25:
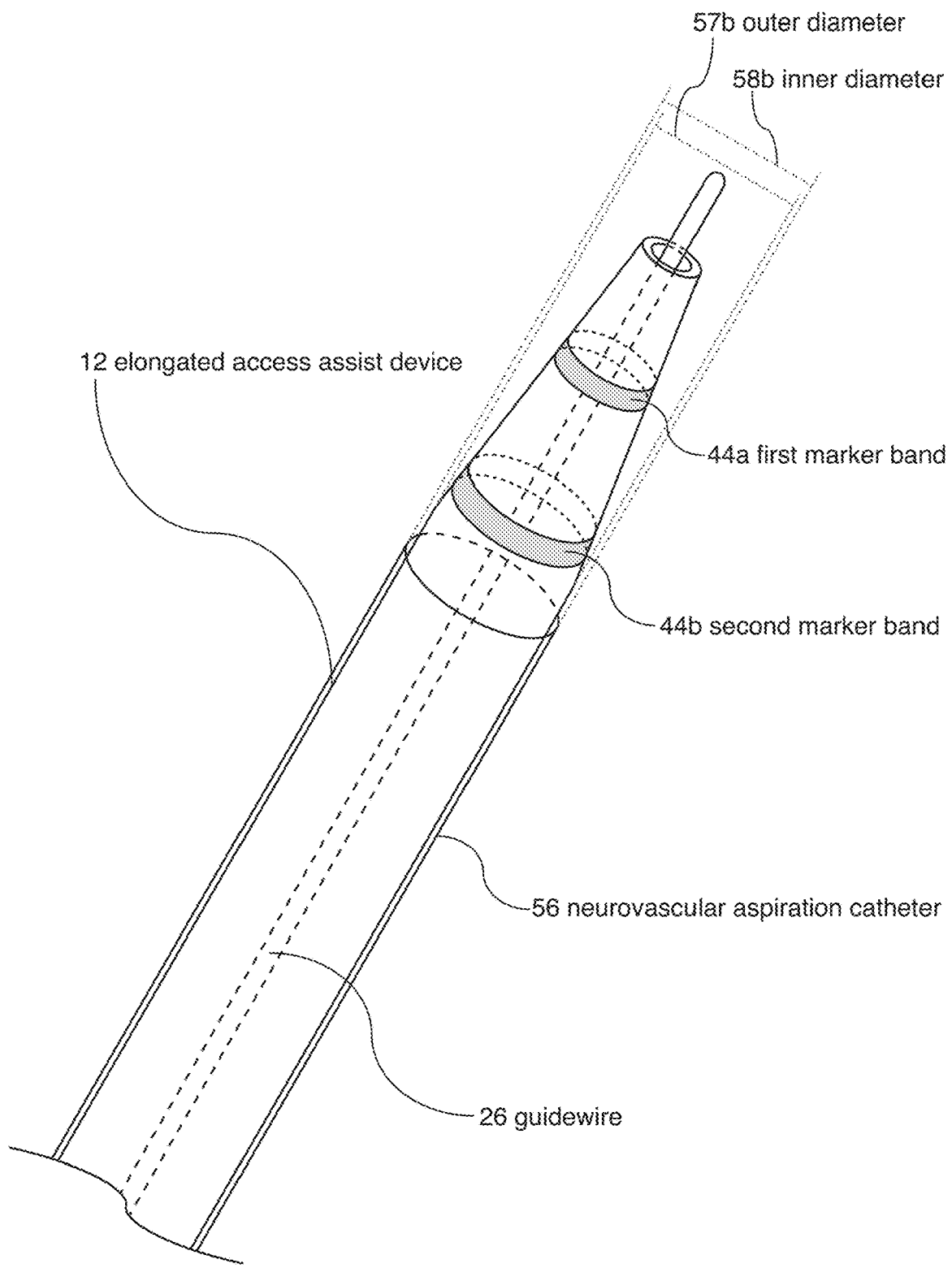
Figure 26:
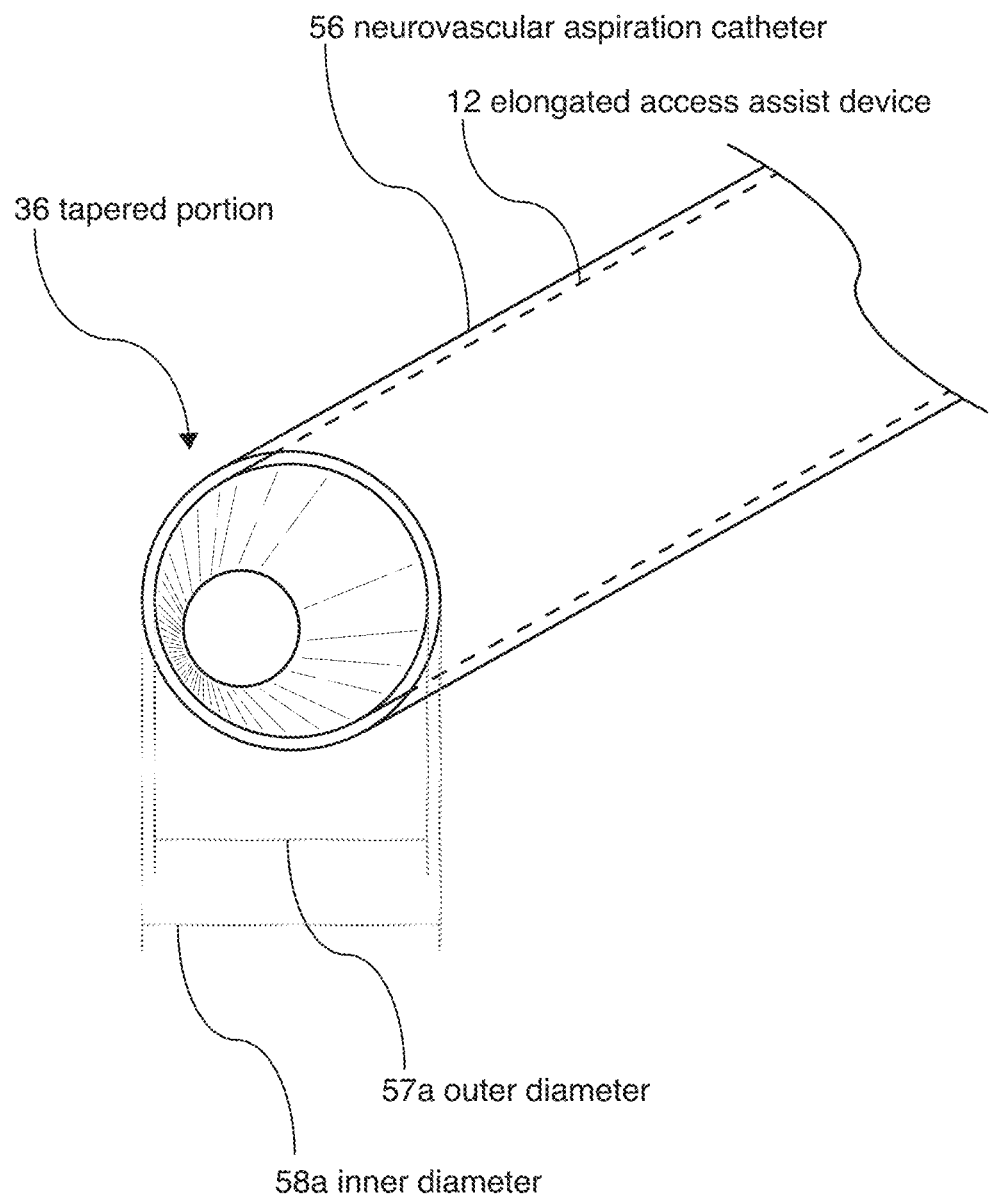

FIGS. 24-26 are similar to FIGS. 21-23, but show a different primary device. Instead of a neurovascular sheath 50, FIGS. 24-26 demonstrate that, in some embodiments, the elongated access assist device 12 is used in conjunction with a neurovascular aspiration catheter 56. The neurovascular aspiration catheter 56 may define an inner diameter 58a, while the elongated access assist device 12 may define an outer diameter 57a, as indicated in FIG. 24. FIG. 25 shows another embodiment of the system 10 including the neurovascular aspiration catheter 56, and shows that the device 12 may define an outer diameter 57b and the catheter 56 may define an inner diameter 58b. Each of the outer diameter 57a, the outer diameter 57b, the inner diameter 58a, and the inner diameter 58b may define diameters provided in the table above included with the discussion of FIG. 21. In some embodiments, at least one of the outer diameter 57a, the outer diameter 57b, the inner diameter 58a, and the inner diameter 58b defines a diameter not provided in the table above. FIG. 25, like FIG. 22, also shows the first and second marker bands 44a, 44b with adjusted locations as compared to FIG. 24. FIG. 26, like FIG. 23, shows a front perspective view of the neurovascular aspiration catheter 56 tracked over the elongated access assist device 12, and demonstrates the small gap between the device 12 and the catheter 56, as a result of the similar diameters 57a and 58a.

Figure 27:
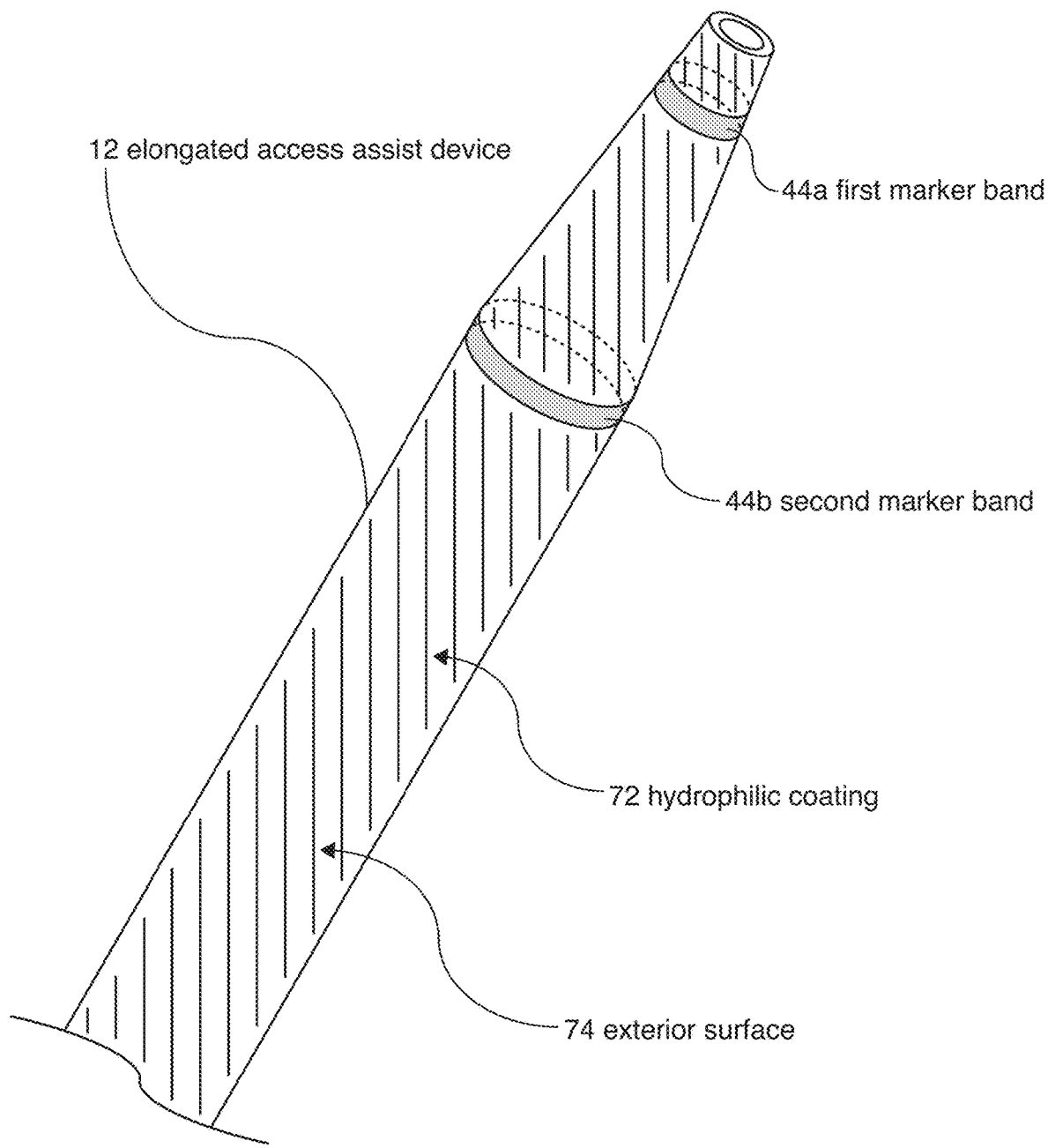
FIGS. 27, 28, 29, 30, 31, 32, and 33 illustrate perspective views of an elongated access assist device including a hydrophilic coating, according to some embodiments.
Figure 28:
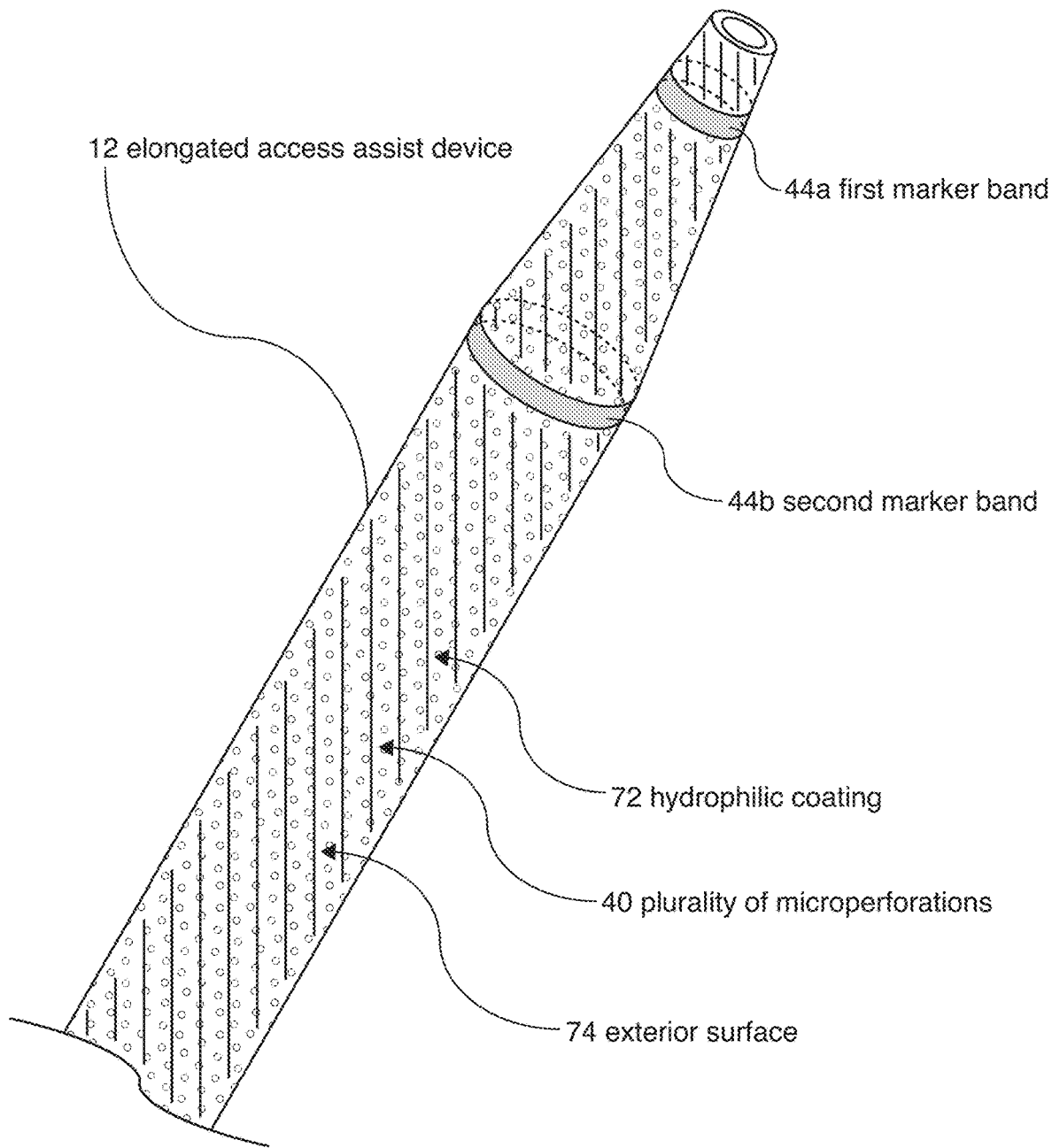
Figure 29:
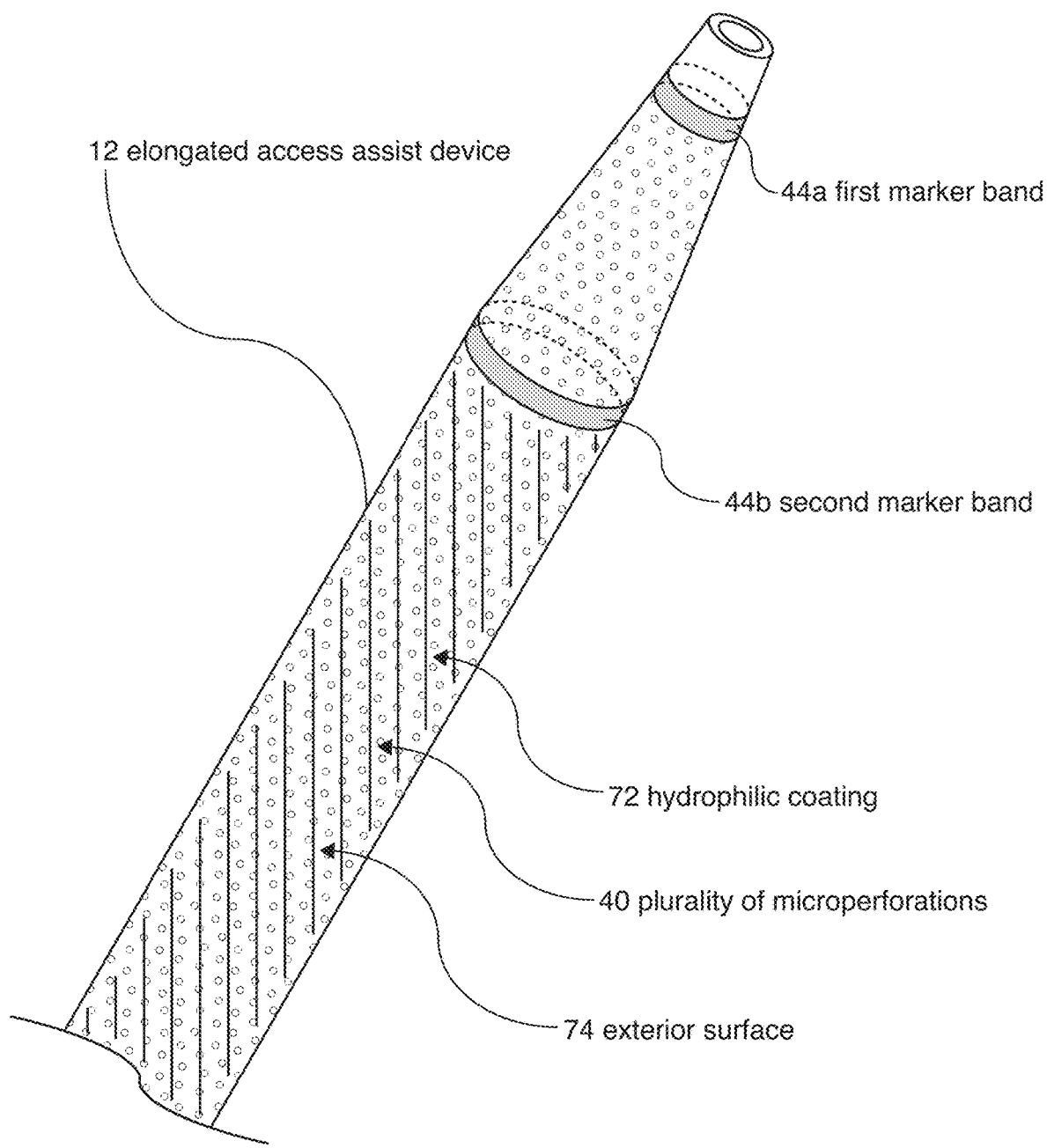
Figure 30:
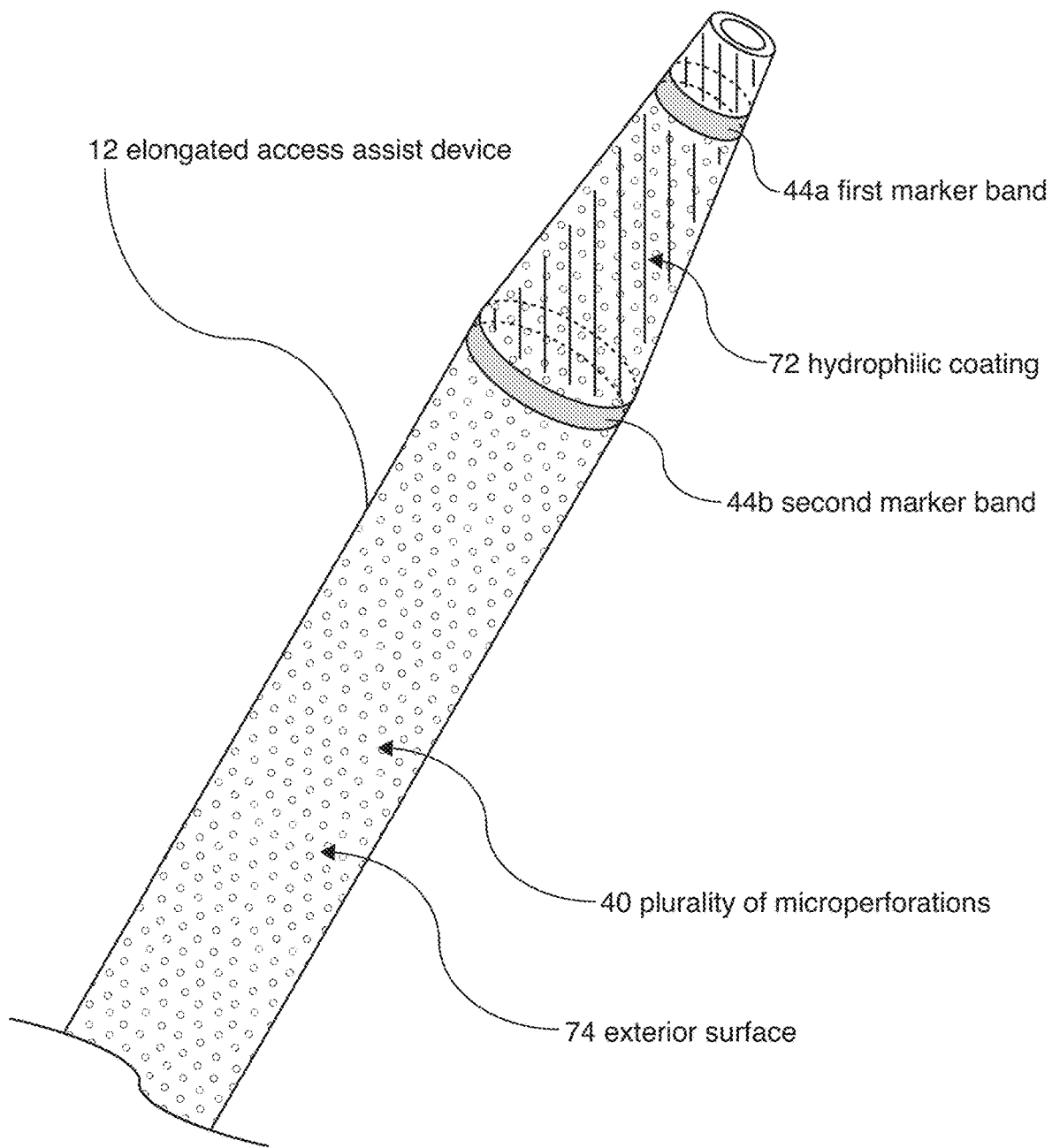
Figure 31:
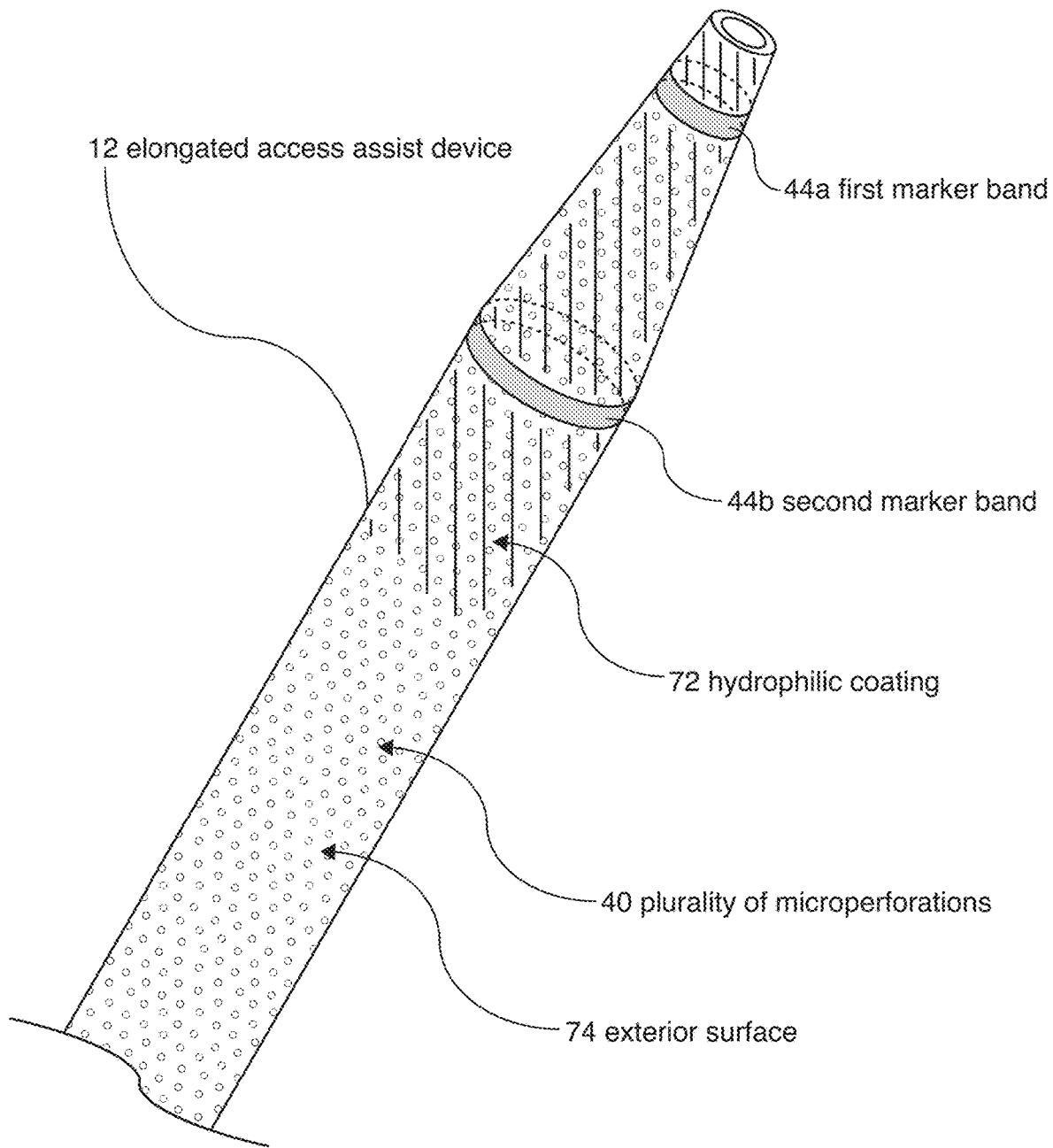
Figure 32:
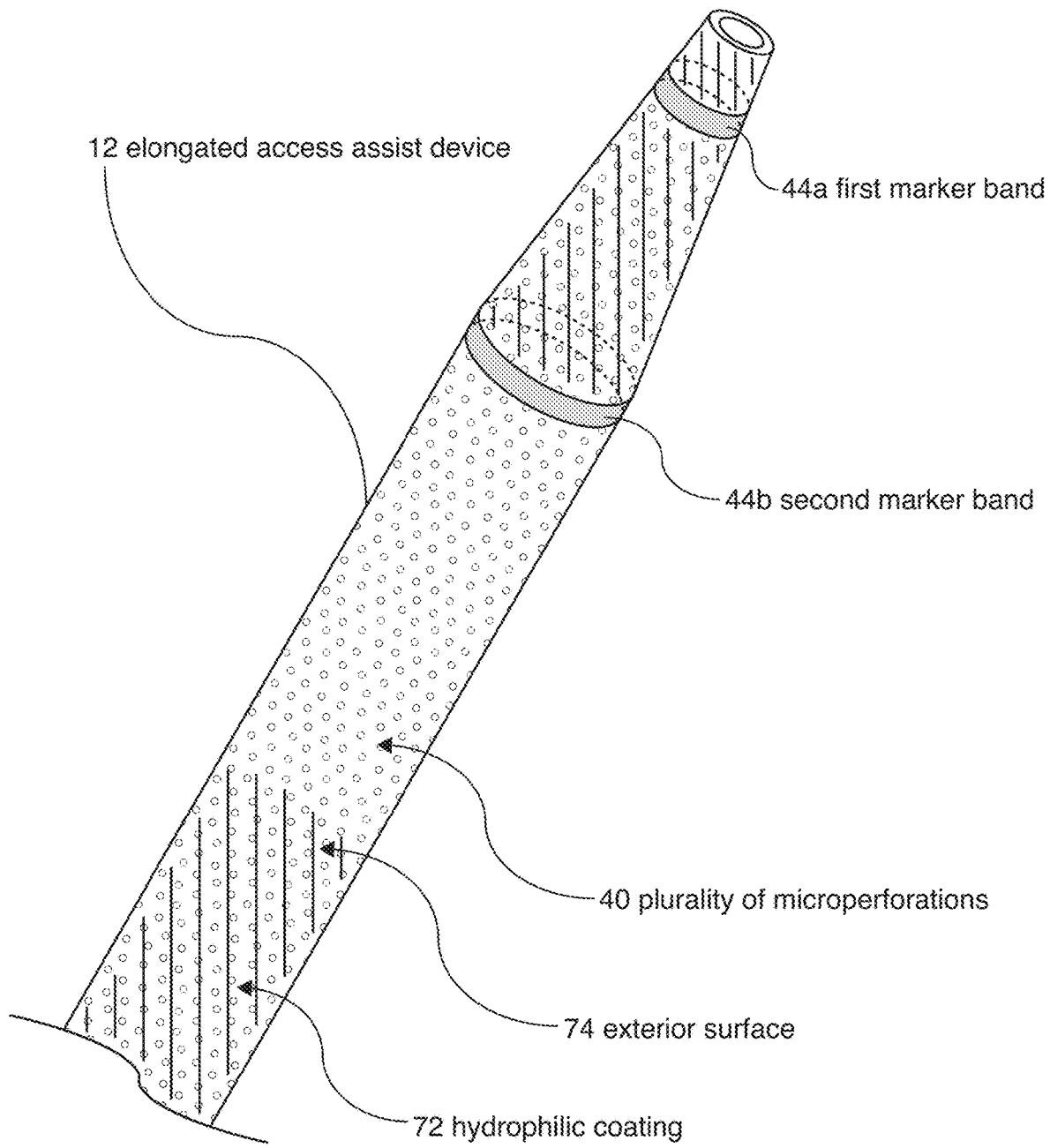
Figure 33:
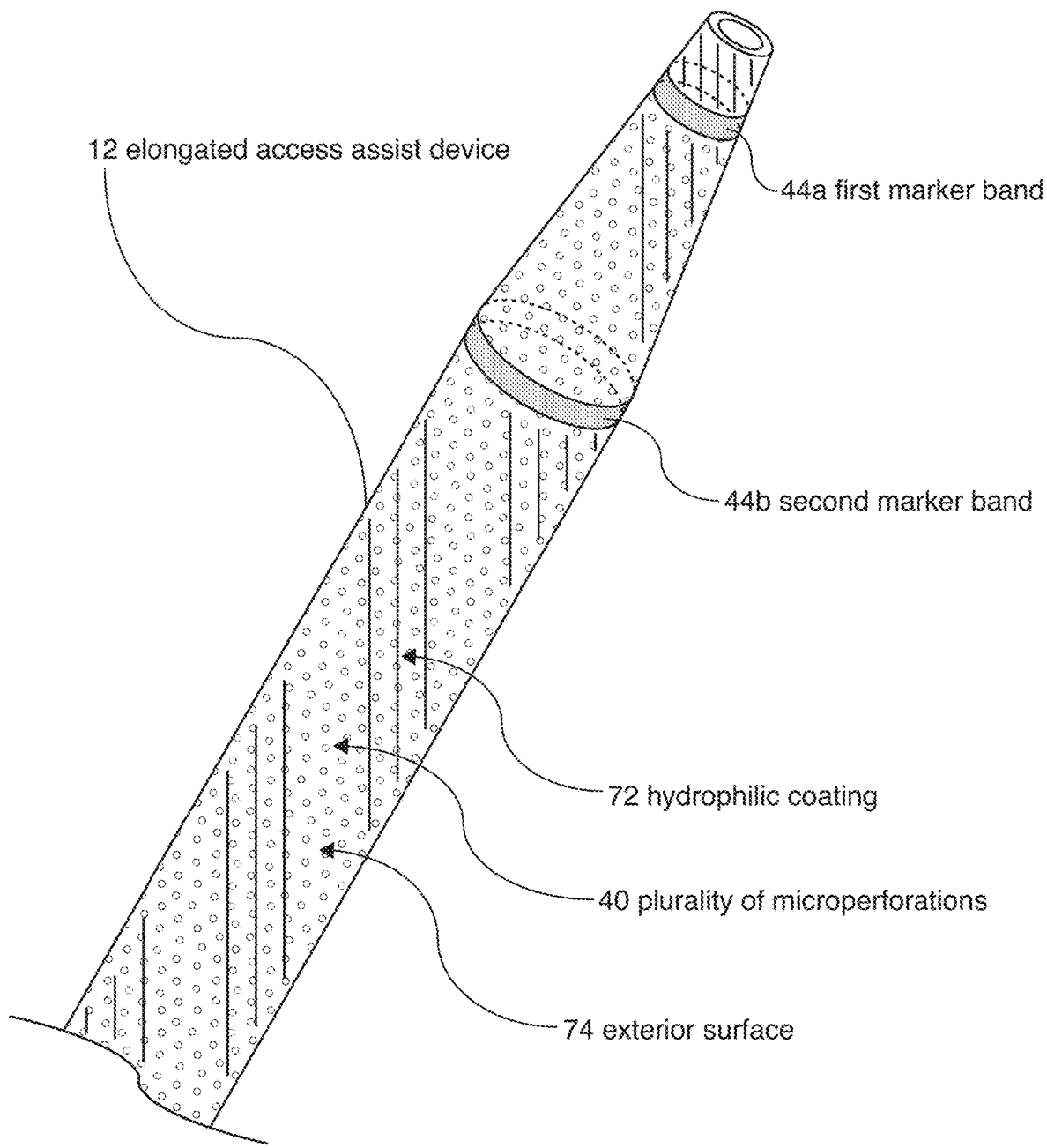

In many embodiments, the catheter system 10 includes a hydrophilic coating 72 located on at least a portion of an exterior surface 74 of the elongated access assist device 12, as indicated by FIGS. 27-33. Similar to the plurality of microperforations 40, the hydrophilic coating 72 may be located on substantially the entire exterior surface 74, as shown in FIGS. 27 and 28, or may be located on one or multiple portions of the exterior surface 74. For example, FIG. 29 shows that the hydrophilic coating 72 may be located on only a body portion of the elongated access assist device 12, but not on the tapered portion 36. In some embodiments, as illustrated in FIG. 30, the hydrophilic coating 72 is located only on an exterior surface 74 of the tapered portion 36 of the elongated access assist device 12. FIG. 31 shows the hydrophilic coating 72 located on the tapered portion 36, as well as extending proximally onto part of the body portion of the elongated access assist device 12. In some embodiments, as shown in FIG. 32, the hydrophilic coating 72 is located on two distinct portions of the elongated access assist device 12. FIG. 33 shows that the hydrophilic coating 72 may be located on more than two distinct portions of the elongated access assist device 12. Of course, the embodiments shown in FIGS. 27-33 demonstrate only a few possible arrangements of the hydrophilic coating 72, and are not intended to be limiting embodiments.

In many embodiments, the hydrophilic coating 72 comprises a lubricious coating which further, along with the conical tip design, the saline perfusion, and the diameters of the elongated access assist device 12 and the primary device, helps the catheter system 10 navigate through tortuous anatomy to reach an occlusion site with minimized shelf effect along the way.

Figure 34:
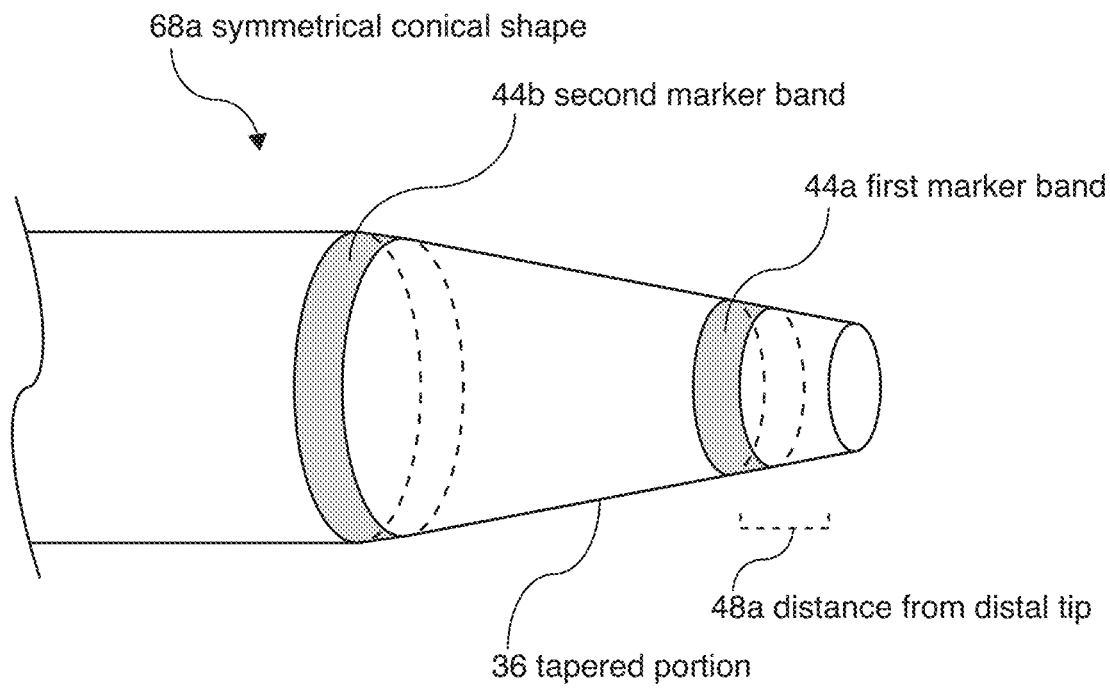
FIGS. 34, 35, 36, 37, 38, 39, 40, 41, 42, 43, 44, 45, 46, and 47 illustrate perspective views of a tapered portion of an elongated access assist device including at least one marker band, according to some embodiments.
Figure 35:
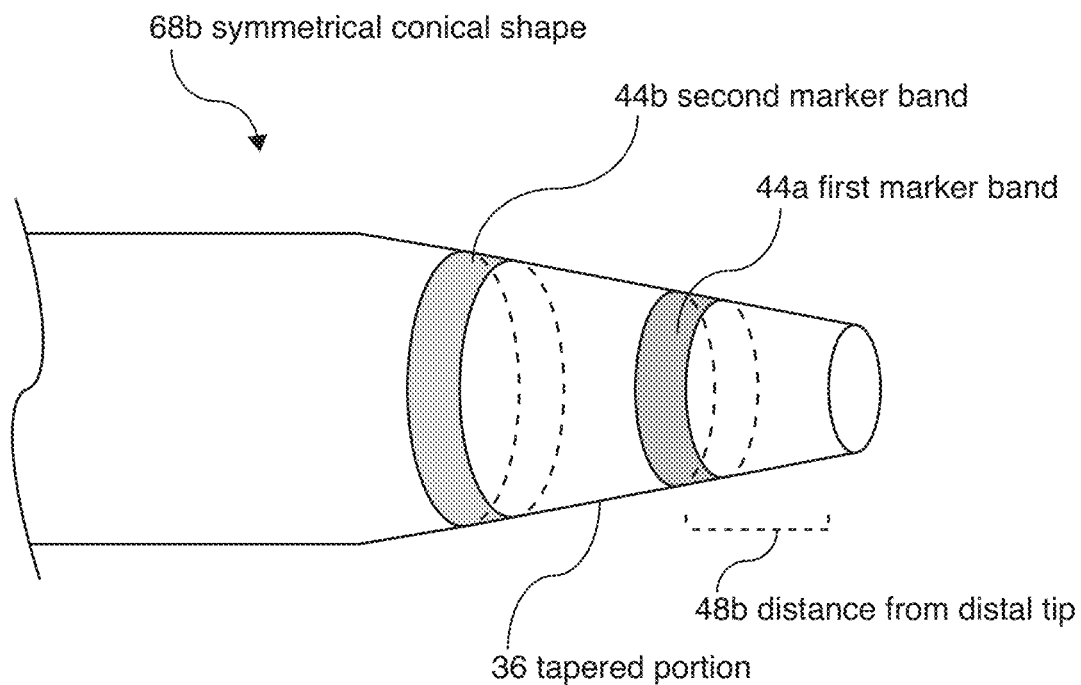

FIGS. 34-47 illustrate different embodiments of the elongated access assist device 12, including varying shapes of the tapered portion 36 and varying numbers and sizes of marker bands. FIG. 34 shows an embodiment where the tapered portion 36 defines a symmetrical conical shape 68a, similar to that shown in the previous Figures. FIG. 34 also shows the first marker band 44a and second marker band 44b located at what may be considered the "typical" positions; where the first marker band 44a is located adjacent the distal tip 46 and the second marker band 44b is located proximal (e.g., at the "beginning" of) the tapered portion 36. In contrast, FIG. 35 illustrates a substantially similar symmetrical conical shape 68b, but shows the first marker band 44a located proximally compared to the "typical" position and the second marker band 44b located distally compared to the "typical" position. As previously stated, in many embodiments, the first and second marker bands 44a, 44b comprise radiopaque material. In some embodiments, radiopaque material is used for radiopacity and visualization of the device as the device tracks through the neurovasculature during a procedure. The radiopaque material may comprise at least one of platinum and iridium. In some embodiments, both the first and second marker bands 44a, 44b comprise platinum. Both the first and second marker bands 44a, 44b may comprise iridium. One marker band 44a or 44b may comprise platinum while the other marker band 44b or 44a comprises iridium. Either or both of the first and second marker bands 44a, 44b may comprise a combination of platinum and iridium, or may comprise a different radiopaque material.

FIGS. 34 and 35 also illustrate the distance of the marker band 44a from the distal tip 46, indicated as distance from distal tip 48a in FIG. 34 and distance from distal tip 48b in FIG. 35. In some embodiments, the first marker band 44a is located adjacent the distal tip 46. The distance from distal tip 48a may be about 0.5-1 mm, and the distance from distal tip 48b may be about 1-2 mm. The distance from distal tip 48a may be smaller than 0.5 mm or larger than 1 mm. The distance from distal tip 48b may be smaller than 1 mm or larger than 2 mm.

Figure 36:
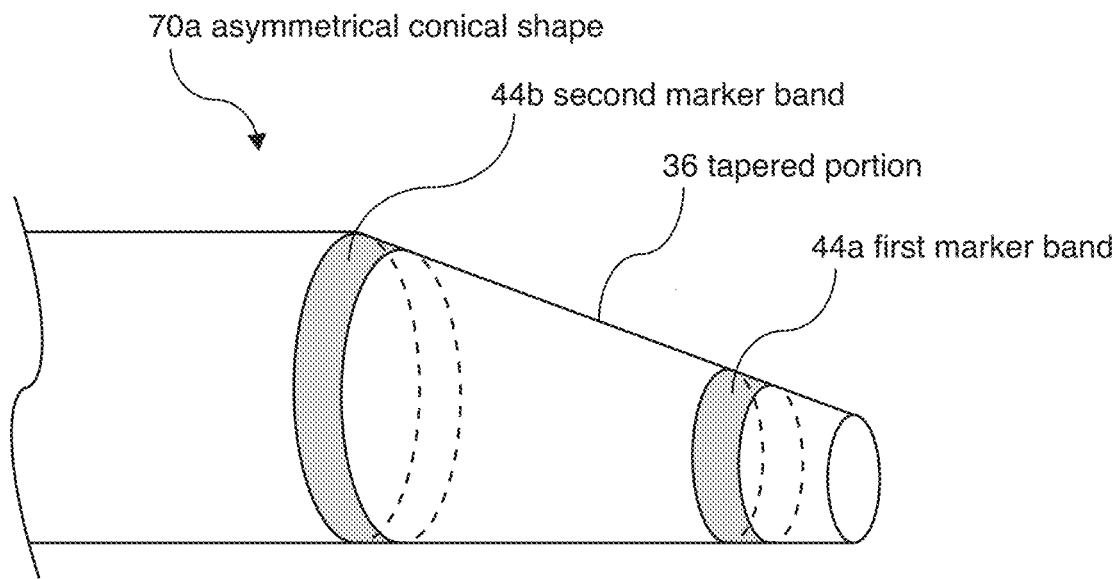
Figure 37:
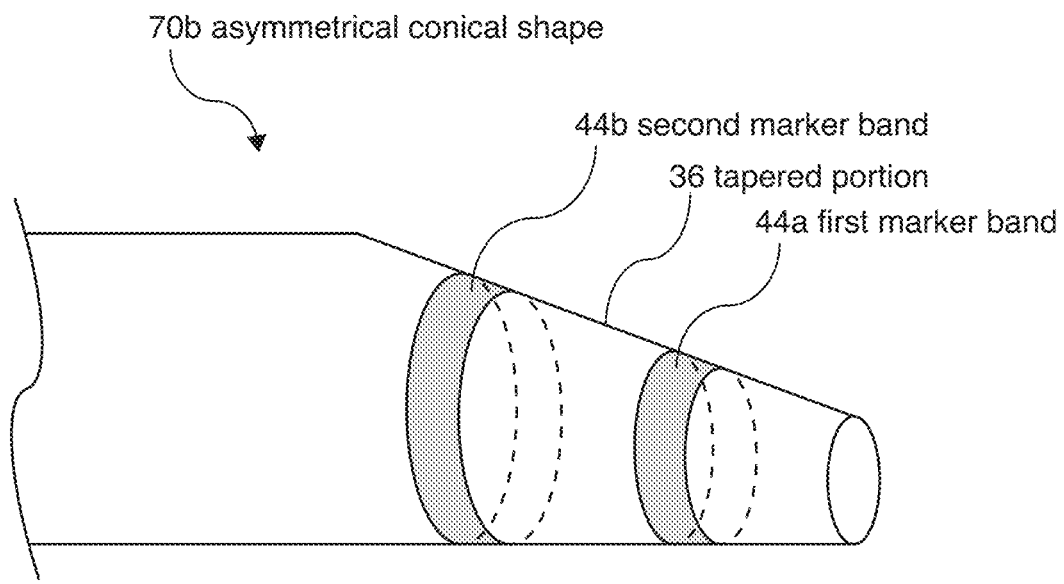

FIGS. 36 and 37 illustrate other embodiments of the elongated access assist device 12, where the tapered portion 36 defines an asymmetrical conical shape 70a, 70b. In some embodiments, the asymmetrical conical shape 70a, 70b defines an offset shape where one side of the tapered portion 36 is straight and another side extends down at an angle from the body of the device 12 to the distal tip 46, as shown in FIGS. 36 and 37. FIGS. 36 and 37 also include the first and second marker bands 44a, 44b, where FIG. 36 shows the marker bands 44a, 44b in the "typical" position, and FIG. 37 shows them in an adjusted position. It should be noted that though not shown in the Figures, at least one of the marker bands 44a, 44b may be located more proximally than just proximal to the tapered portion 36. For example, at least one of the marker bands 44a, 44b may be located on a body portion of the elongated access assist device 12 away from the tapered portion 36. In most embodiments though, at least one of the marker bands 44a, 44b is located closer to the distal end 16 of the elongated access assist device 12 than the proximal end 14 of the elongated access assist device 12.

Figure 38:
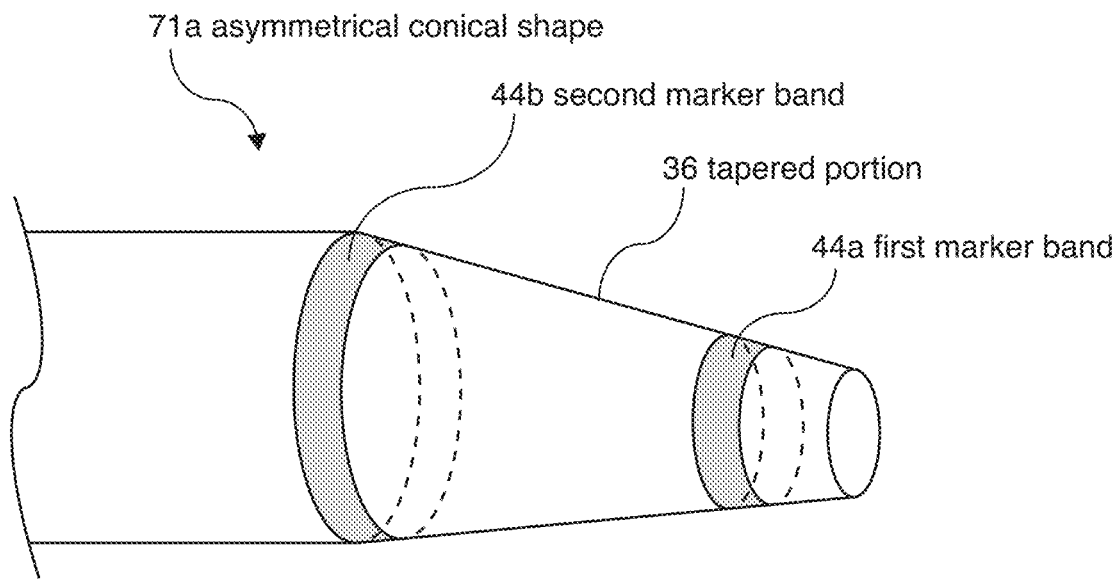
Figure 39:
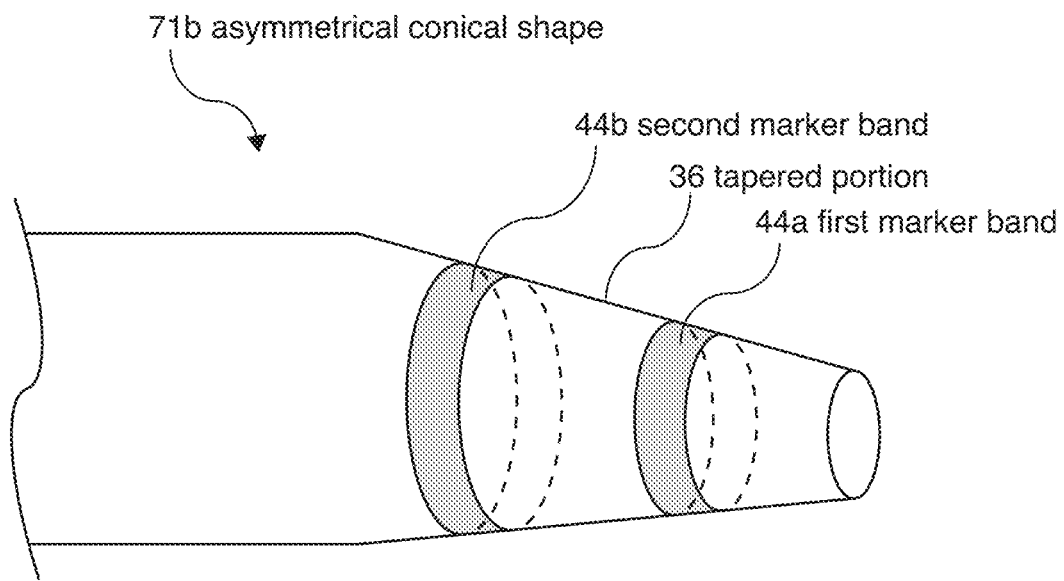

FIGS. 38 and 39 show additional embodiments of the elongated access assist device 12, where the tapered portion 36 defines an asymmetrical conical shape 71, 71b. As illustrated, the asymmetrical conical shape 71a, 71b is not quite the offset shape shown in FIGS. 36 and 37, as both sides of the tapered portion 36 are slanted. It should be noted that the tapered portion 36 may define any number of shapes, including shapes beyond those illustrated in the Figures. FIGS. 38 and 39 also include the first and second marker bands 44a, 44b, where FIG. 38 may be considered to show the marker bands 44a, 44b in the "typical" position and FIG. 39 may be considered to show the marker bands 44a, 44b in an altered position.

Figure 40:
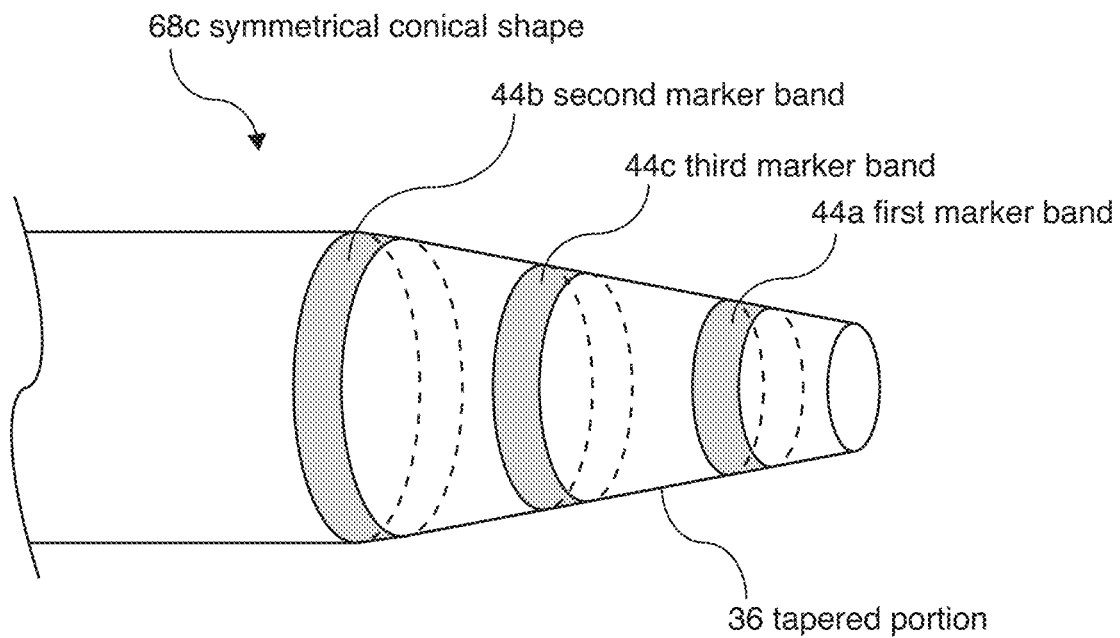
Figure 41:
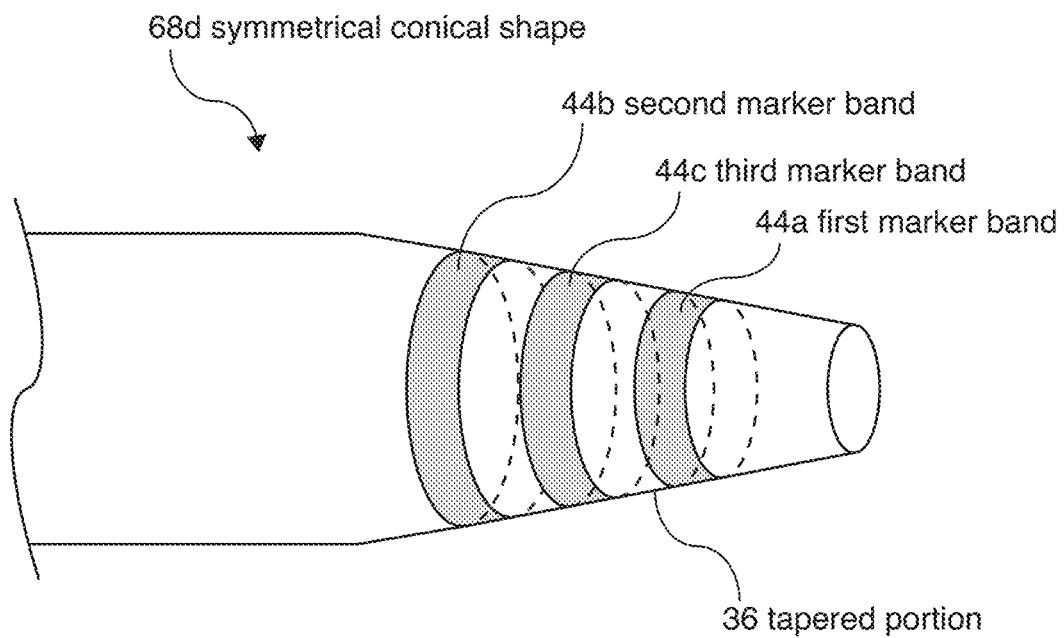

FIGS. 40 and 41 show further embodiments of the elongated access assist device 12, where the tapered portion 36 defines a symmetrical conical shape 68c, 68d. In many embodiments, the symmetrical conical shapes 68a, 68b, 68c, and 68d define substantially the same shape but the embodiments include differences regarding the marker bands 44a, 44b, and/or 44c. For example, FIG. 34 shows the tapered portion 36 defining the symmetrical conical shape 68a, with the first and second marker bands 44a, 44b in the "typical" position. Similarly, FIG. 40 shows the tapered portion 36 defining the symmetrical conical shape 68c with the first and second marker bands 44a, 44b in the "typical" position. FIG. 40 also includes a third marker band 44c, which is shown located between the first and second marker bands 44a, 44b. The third marker band 44c may be located substantially evenly between the first marker band 44a and the second marker band 44b, as illustrated in FIGS. 40 and 41, or may be located closer to either the first marker band 44a or the second marker band 44b.

Similar to the first and second marker bands 44a, 44b, the third marker band 44c may comprise at least one of platinum and iridium. In some embodiments, all three marker bands 44a, 44b, 44c comprise platinum. All three marker bands 44a, 44b, 44c may comprise iridium. In some embodiments, two marker bands comprise platinum while the third comprises iridium. Two marker bands may comprise iridium while the third comprises platinum. At least one of the first, second, and third marker bands 44a, 44b, 44c may comprise a combination of platinum and iridium. At least one of the first, second, and third marker bands 44a, 44b, 44c may comprise a different radiopaque material. At least one of the first, second, and third marker bands 44a, 44b, 44c may comprise a combination of platinum, iridium, and/or a different radiopaque material.

Figure 42:
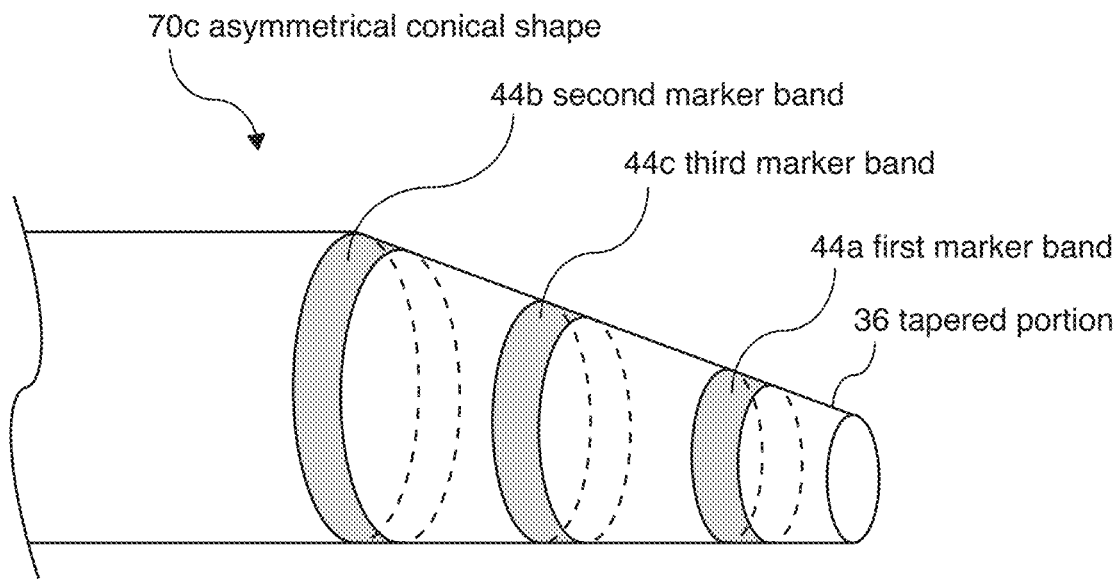
Figure 43:
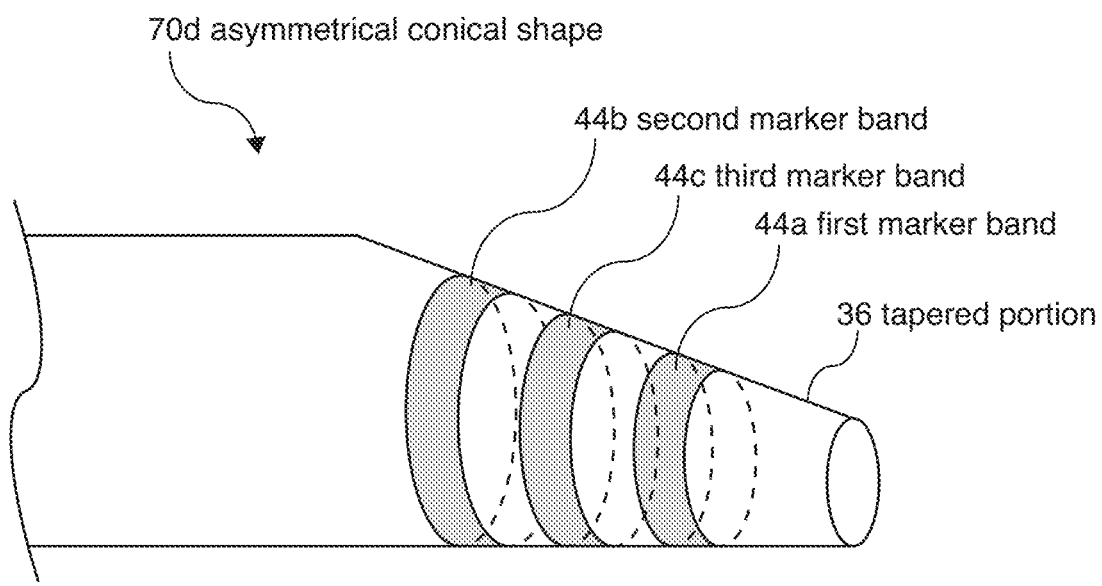

FIGS. 42 and 43 illustrate embodiments of the elongated access assist device 12 where the tapered portion 36 defines an asymmetrical conical shape 70c, 70d. Similar to the asymmetrical conical shape 70a, 70b shown in FIGS. 36 and 37, the asymmetrical conical shape 70c, 70d may define an offset conical shape where one side extends substantially straight from the body portion of the elongated access assist device 12 and the other side extends at an angle from the body toward the distal tip 46. Like FIGS. 40 and 41, FIGS. 42 and 43 show embodiments comprising a first marker band 44a, a second marker band 44b, and a third marker band 44c. In some embodiments, the third marker band 44c is located on the body of the elongated access assist device 12, rather than the tapered portion 36.

Figure 44:
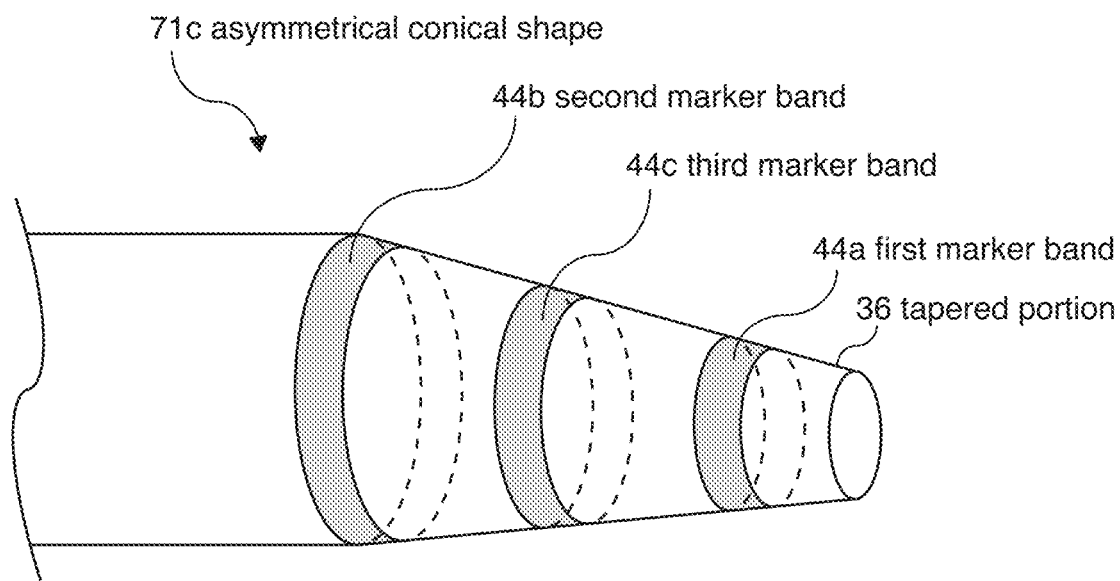
Figure 45:
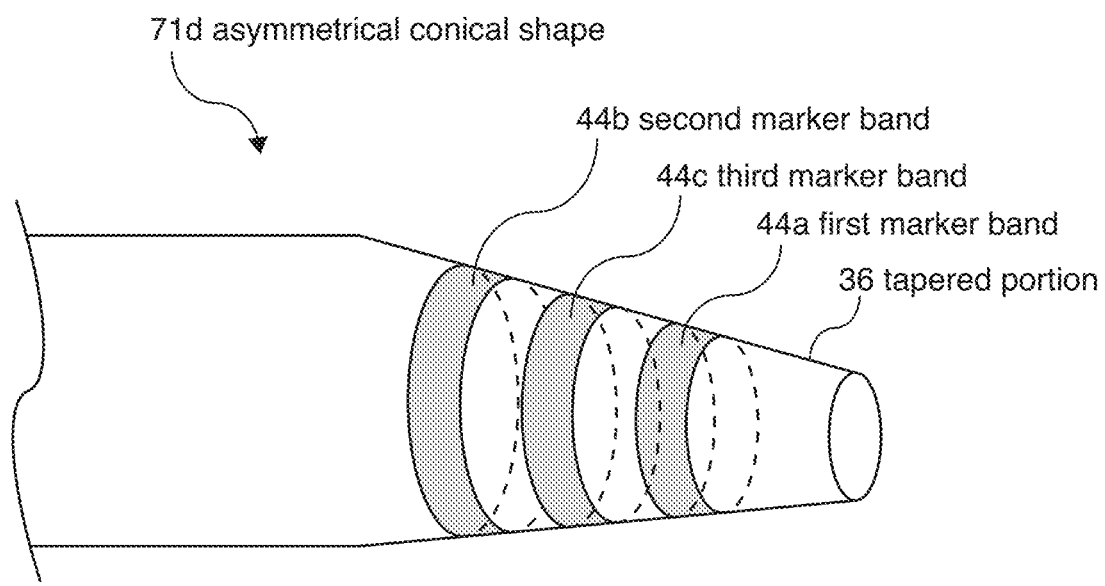
Figure 46:
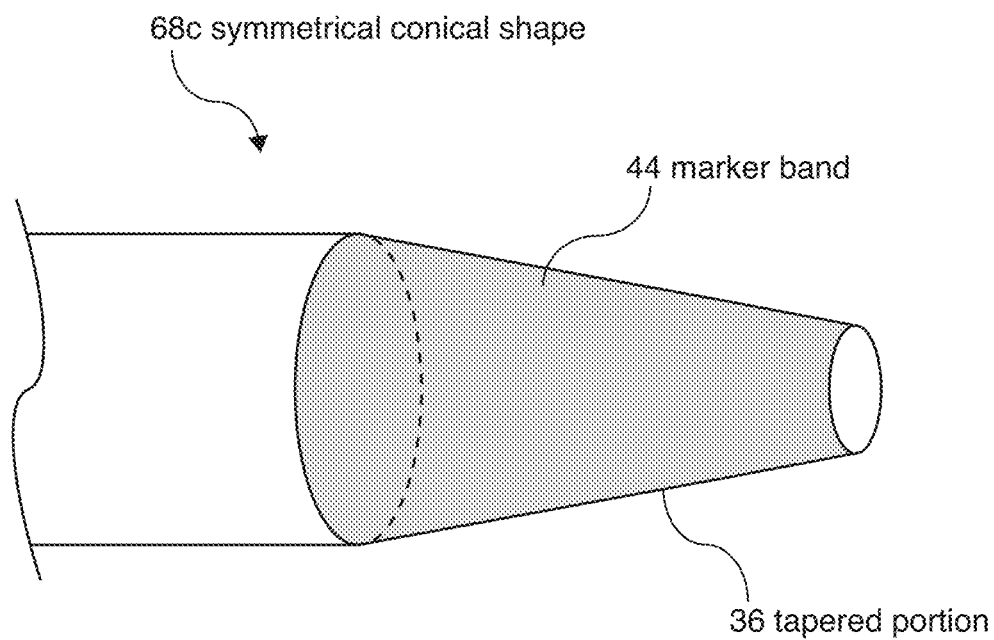

FIGS. 44 and 45 show embodiments of the elongated access assist device 12 where the tapered portion 36 defines an asymmetrical conical shape 71c, 71d, which may be substantially similar to the asymmetrical conical shape 71a, 71b illustrated in FIGS. 38 and 39. Like FIGS. 40-43, FIGS. 44 and 45 illustrate that, in some embodiments, the elongated access assist device 12 comprises a third marker band 44c in addition to the first marker band 44a and second marker band 44b. In some embodiments, the elongated access assist device 12 comprises more than three marker bands. The elongated access assist device 12 may comprise a single marker band 44, as demonstrated in FIG. 46. In some embodiments, the single marker band 44 comprises substantially the entire tapered portion 36 of the device 12. The single marker band 44 may be smaller than illustrated in FIG. 46, such that the marker band 44 takes up a smaller portion of the tapered portion 36. For example, the marker band 44 may be configured to cover a distal half of the tapered portion 36. The marker band 44 may be configured to cover a proximal half of the tapered portion 36. In some embodiments, the marker band 44 is configured to cover a central portion of the tapered portion 36. The marker band 44 may also be larger than illustrated in FIG. 46, such that the marker band 44 takes up substantially all of the tapered portion 36 and at least a portion of the body of the elongated access assist device 12.

Figure 47:
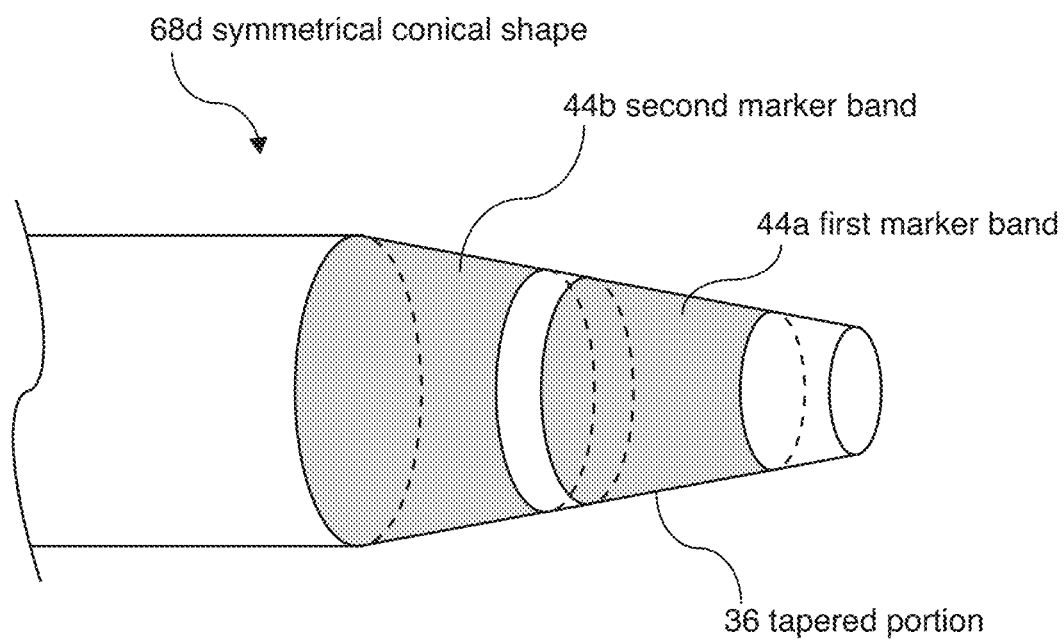

FIG. 47 demonstrates that the first and second marker bands 44a, 44b may define a different size than shown in the previous Figures. For example, as shown in FIG. 47, the first and second marker bands 44a, 44b may be wider than the first and second marker bands 44a, 44b shown, for example, in FIGS. 34-45. The first and second marker bands 44a, 44b may also be narrower than the first and second marker bands shown in FIGS. 34-45. In some embodiments, the first marker band 44a is wider than previously depicted while the second marker band 44b is narrower than previously depicted, or vice versa. On any given embodiment of the elongated access assist device 12, the first, second, and third marker bands 44a, 44b, 44c are not necessarily the same size. Similar to how two or all three of the marker bands 44a, 44b, 44c may comprise the same material, two or all three of the marker bands 44a, 44b, 44c may define the same size. In some embodiments, each of the first marker band 44a, the second marker band 44b, and the third marker band 44c define a different size and/or comprise a different material.

Figure 48:
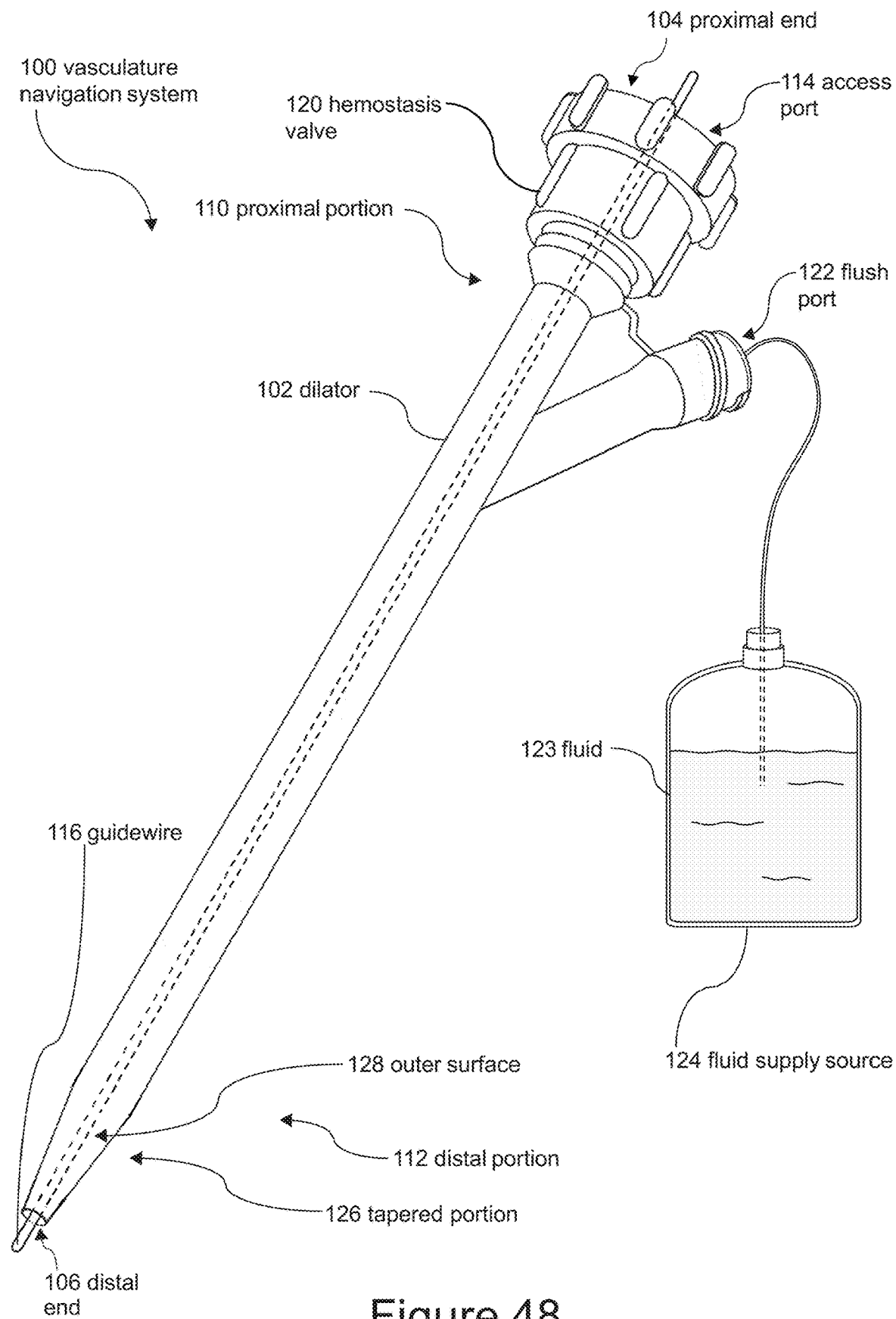
FIG. 48 illustrates a perspective view of a vasculature navigation system, according to some embodiments.

FIG. 48 illustrates an embodiment of a vasculature navigation system 100. It should be noted that the vasculature navigation system 100 may be similar to the catheter system 10 shown in FIGS. 1-47 and previously discussed in this disclosure. For example, as shown in FIG. 48, the vasculature navigation system 100 may include an access port 114, a flush port 122, a hemostasis valve 120, and a fluid supply source 124 that may be substantially the same as the access port 24, flush port 32, hemostasis valve 30, and fluid supply source 34 of the catheter system 10. In addition, the vasculature navigation system 100 may include a guidewire 116 and a tapered portion 126 substantially similar to the guidewire 26 and tapered portion 36 of the catheter system 10. Moreover, FIG. 48 includes parallel broken lines extending along the center of the dilator 102, which illustrate the location and/or path of the guidewire 116 along the internal portion of the dilator 102.

In some embodiments, as illustrated in FIG. 48, the vasculature navigation system 100 comprises a dilator 102 having a proximal end 104 and a distal end 106 located opposite the proximal end 104. The vasculature navigation system 100 may include a guidewire lumen extending between the proximal end 104 and the distal end 106, wherein the guidewire lumen is configured to receive the guidewire 116. In some embodiments, the guidewire lumen is also configured to receive fluid 123 from the fluid supply source 124, as will be discussed further with reference to FIG. 49. The dilator 102 may also include a proximal portion 110 and a distal portion 112 located opposite the proximal portion 110, as shown in FIG. 48. In some embodiments, and similar to the catheter system 10, the proximal portion 110 includes an access port 114 configured to receive the guidewire 116, a hemostasis valve 120 configured to control fluid flow between the proximal portion 110 and the distal portion 112, and a flush port 122 located distal to the hemostasis valve 120 and configured to couple to the fluid supply source 124. The distal portion 112 may include a distal port located at the distal end 106 and configured to further receive the guidewire 116, as illustrated in FIG. 48.

The dilator 102 may also include a tapered portion 126 defining at least part of the distal portion 112 of the dilator 102. In some embodiments, an outer surface 128 of the tapered portion 126 tapers down toward the distal end 106. The tapered portion 126 may define a symmetrical, conical shape, similar to the tapered portion 36 illustrated in FIGS. 34, 35, 40, 41, 46 and 47. In some embodiments, the tapered portion 126 defines a short length. For example, the tapered portion 126 may define a length of about 3-5 mm. The tapered portion 126 may define a greater length, for example 1, 2, 5, 10, or 20 cm, as previously discussed in this disclosure. The tapered portion 126 may define a length of less than 3 mm. The tapered portion 126 may define a length between 5 mm and 1 cm. In some embodiments, the tapered portion 126 includes a rounded, or "bull-nose" tip, rather than a blunt tip.

Figure 49:
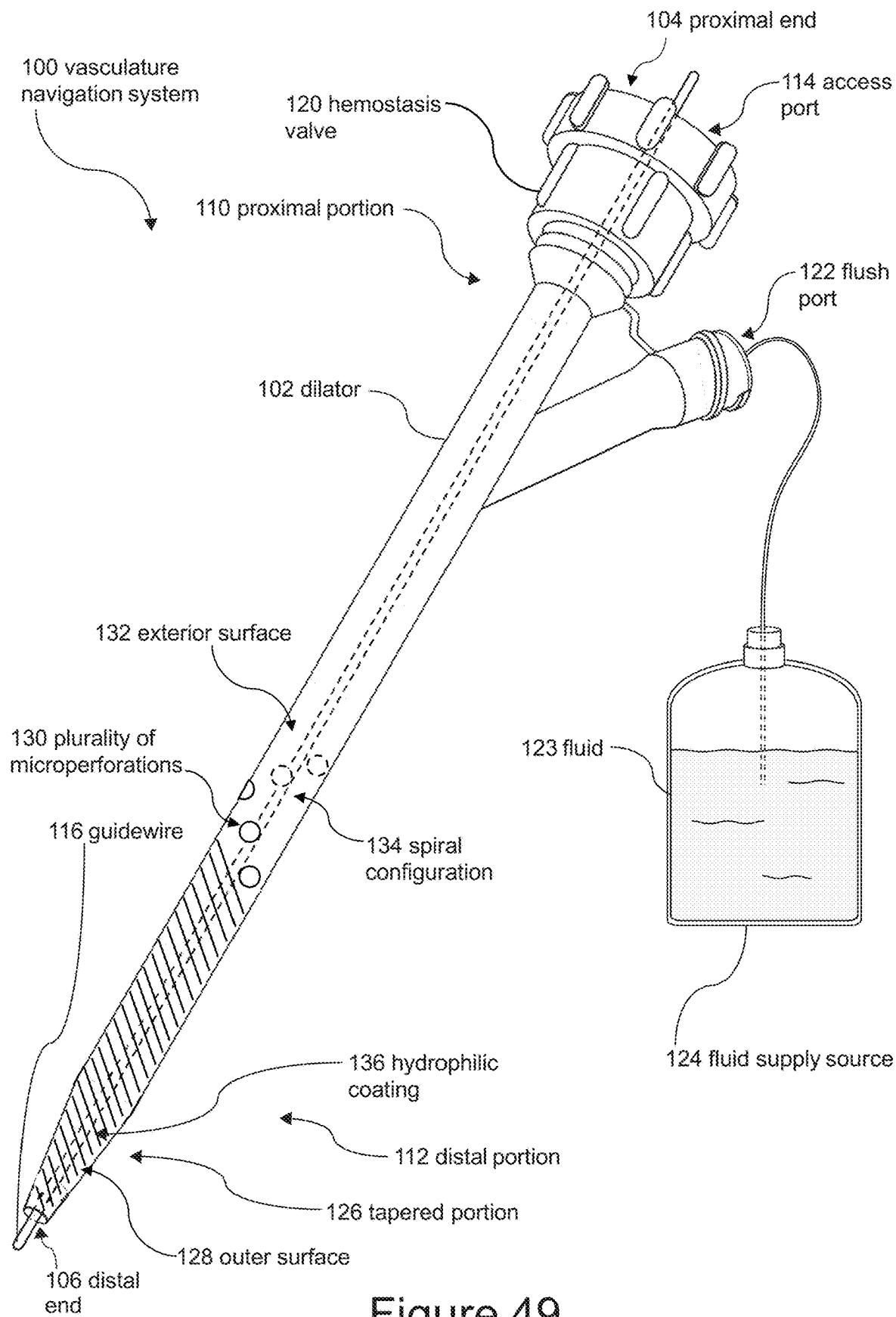
FIG. 49 illustrates a perspective view of a vasculature navigation system including a hydrophilic coating and a plurality of microperforations, according to some embodiments.

FIG. 49 is similar to FIG. 48, and includes additional elements of the vasculature navigation system 100. For example, in some embodiments, the system 100 includes a plurality of microperforations 130 coupled to at least a portion of an exterior surface 132 of the dilator 102, including a "back" surface of the dilator 102, as indicated by the microperforations shown in dashed lines. As illustrated in FIG. 49, the plurality of microperforations 130 may be located between the proximal portion 110 and the distal portion 112. In some embodiments, the plurality of microperforations 130 are located more on the proximal portion 110, closer to the proximal end 104 than the distal end 106. In some embodiments, the plurality of microperforations 130 are located more on the distal portion 112, closer to the distal end 106 than the proximal end 104. The plurality of microperforations 130 may be located substantially at a central portion of the dilator 102, in terms of the working length. Each microperforation of the plurality of microperforations 130 may define an aperture, or simple hole or opening, without a valve or other sort of mechanism obstructing and/or covering either an internal or external portion of each microperforation.

In some embodiments, the plurality of microperforations 130 are configured to release fluid 123 from the fluid supply source 124. The fluid 123 may be released through the plurality of microperforations 130 in a substantially continuous flow. In some embodiments, the fluid 123 is released in discrete bursts, such as in separate ejections, waves, and the like. The system 100 may include a valve coupled to at least one of the flush port 122 and the fluid supply source 124, the valve comprising a pressure activated valve configured to control fluid flow from at least one of the flush port 122 and the fluid supply source 124. The valve may be configured to prevent backflow and/or entrance of air if the fluid supply source 124 becomes disconnected.

The fluid supply source 124 may be pressurized. In some embodiments, the fluid supply source 124 is pressurized to an extent sufficient to enable propulsion of the dilator 102 upon release of fluid 123 via the plurality of microperforations 130. The fluid 123 may, in turn, be pressurized within the dilator 102 to the extent sufficient to enable propulsion. In some embodiments, at least one of the fluid 123 and the fluid supply source 124 is pressurized to about 300 psi. The fluid 123 may comprise saline. The release of fluid 123 through the plurality of microperforations 130 may also help keep the dilator 102 centered within the vasculature (e.g., within a particular blood vessel) of the patient.

In some embodiments, the fluid 123 comprises a therapeutic agent released to provide treatment, rather than propulsion. For example, when the vasculature navigation system 100 is used during a neurological or vascular procedure, the fluid 123 may comprise heparinized saline. The fluid 123 may comprise other medication and/or therapeutic agents, like warm saline, cold saline, and contrast dye, to name a few. In some embodiments, the fluid 123 is configured to provide both propulsion and therapeutic effect.

FIG. 49 also illustrates that, in some embodiments, the system 100 comprises a hydrophilic coating 136 located on the distal portion 112 of the dilator 102. The hydrophilic coating 136 may be configured to reduce friction between the dilator 102 and the patient's vasculature. In some embodiments, the combination of the plurality of microperforations 130 and the hydrophilic coating 136 is also configured to enable navigation of the dilator 102 through the patient's vasculature by reducing friction between the dilator 102 and the patient's vasculature. As illustrated in FIG. 49, the plurality of microperforations 130 may be located just proximal to the hydrophilic coating 136 such that the fluid 123 released from the plurality of microperforations 130 is configured to flow distally over the hydrophilic coating 136. In some embodiments, substantially continuous lubrication of the hydrophilic coating 136, by the fluid 123, enables better navigation of the dilator 102. It should be noted that the guidewire lumen may be configured to receive the guidewire 116 and fluid 123 simultaneously, such that the guidewire 116 may be used to assist navigation of the dilator 102 while the fluid 123 is released from the plurality of microperforations 130. Similar to FIG. 48, FIG. 49 includes dashed parallel lines representing the location of the guidewire 116 within an interior of the dilator 102.

In some embodiments, the hydrophilic coating 136 is configured to cover at least a portion of the distal portion 112 of the dilator 102, including the tapered portion 126. The hydrophilic coating 136 may cover the distal 10 cm of the dilator 102. In some embodiments, the hydrophilic coating 136 is configured to cover the distal 20 cm of the dilator 102. The hydrophilic coating 136 may cover a portion of the distal portion 112 less than 10 cm long. The hydrophilic coating 136 may cover a portion of the distal portion 112 greater than 20 cm long. The hydrophilic coating 136 may cover a portion of the distal portion 112 between 10 and 20 cm long. It should be noted that the distal portion 112 and the proximal portion 110 may define unequal lengths. For example, the distal portion 112 may be considered the distalmost 20 cm of the dilator 102, while the proximal portion 110 may be considered the remaining 140 cm of the dilator 102, in an embodiment where the total working length of the dilator 102 is 160 cm. Stated another way, the terms "proximal portion 110" and "distal portion 112" should not necessarily be interpreted as "proximal half" and "distal half." The distal portion 112 may also be defined as the area including the hydrophilic coating 136, while the proximal portion 110 "starts" with the plurality of microperforations 130 and extends to the proximal end 104.

Similar to the elongated access assist device 12 of the catheter system 10, the dilator 102 may be configured to be received by a primary device. In some embodiments, when the dilator 102 is received by a primary device, at least the tapered portion 126 extends distal a distal end of the primary device. The tapered portion 126 and a portion of the non-tapered distal portion 112 may be configured to extend from the primary device. In some embodiments, the hydrophilic coating 136 on the dilator 102 is configured to reduce friction between the dilator 102 and the primary device. Similar to reducing friction in vasculature, the combination of the plurality of microperforations 130 and the hydrophilic coating 136 may also reduce friction between the dilator 102 and the primary device, especially during insertion and/or removal of the dilator 102 from the primary device.

Primary devices may include, but are not limited to, guide catheter(s), aspiration catheter(s), sheath(s), delivery catheter(s) and/or any kind of treatment catheter used within a patient's vasculature to deploy stents, treat blood clots, and/or any number of other uses. The potential uses of the vasculature navigation system 100 are not limited to any particular type of procedure or part of the body, and may be used to generally improve trackability with any catheter through the patient's body. For example, the system 100 may be useful for removing blood clots from either or both lungs by entering the patient through the leg or groin and navigating to a pulmonary artery. The system 100 may also be used in a radial approach to a patient's kidneys, bowel, liver, and/or other abdominal organs. The system 100 can also be used to treat atherosclerosis in the extremities. The system 100 may navigate through venous and arterial systems throughout the body, including, but not limited to, cardiac systems, abdominal systems, and neurovascular systems. In many cases, traditional treatment options for a number of diagnoses—including pulmonary emboli, aortic stenosis, and atherosclerosis, among others-require the use of large catheters that are often difficult to navigate, especially through small vessels and tortuous anatomy. The system 100 enables better navigation to difficult-to-reach treatment locations, and, in some embodiments, is configured for use with many traditional types/models of catheters. The following table represents some different size embodiments of the dilator 102 and indicates which current catheter model is compatible. It should be noted that "outer diameter" refers to the outer diameter of the dilator 102 along substantially the entire length other than the tapered portion 126.

| Outer Diameter | Length | Compatible Catheters |
|---|---|---|
| 0.057" | 160 cm | Stryker ® CAT ™ 6 |
| | | Penumbra ® ACE ™ 60 |
| | | Penumbra ® RED ™ 62 |
| | | Microvention ® SOFIA ™ 5Fr |
| 0.068" | 160 cm | Stryker ® Vecta ™ 74 |
| | | Medtronic ® React ™ 71 |
| | | Penumbra ® JET ™ 7 |
| | | Imperative ® Care Zoom ™ 71 |
| | | Ceronovus ® LBC |
| 0.085" | 132 cm | Penumbra ® Neuron MAX ® |
| | | Penumbra ® BENCHMARK BMX ™ |
| | | Balt ® Ballast ™ |
| | | Cook Medical ® Flexor ® Shuttle ® |
| 0.095" | 160 cm | Penumbra ® CAT ™ 8 Indigo ® System |
| | | Cook Medical ® 8Fr Flexor ® Ansel Sheath |
| 0.12" | 160 cm | 10Fr thrombectomy systems |
| | | 10Fr delivery sheaths |
| 0.15" | 160 cm | Penumbra ® CAT ™ 12 Indigo ® System |

The dimensions in the table above are included as non-limiting examples. In some embodiments, the length of the dilator 102 defines a length other than 132 cm or 160 cm. The dilator 102 may be longer than 160 cm, shorter than 132 cm, or between 132 and 160 cm. The dilator 102 may also define an outer diameter other than the example dimensions included in the table. In some embodiments, the dilator 102 defines an outer diameter of 0.055 inches. The guidewire 116 may define a diameter of 0.013 inches. The guidewire 116 may define a diameter of 0.014 inches. In some embodiments, the guidewire 116 defines a diameter larger than 0.014 inches, such as 0.035 inches. The guidewire 116 may define a diameter between 0.014 inches and 0.035 inches, or greater than 0.035 inches. In some embodiments, the inner diameter of the dilator 102 (i.e., the guidewire lumen) is 0.018 inches. The inner diameter may be consistent throughout the length of the dilator 102, such that even though the outer diameter decreases at the tapered portion 126, the inner diameter is the same at the proximal end 104 and the distal end 106. As indicated by the inner and outer diameter dimensions, in some embodiments, the dilator 102 comprises a thick-walled diameter.

As previously discussed in this disclosure with reference to the catheter system 10, the elongated access assist device 12 may be sized to provide support to the primary device, as well as reduce shelf effect. Similarly, the dilator 102 may be sized to provide support to any of the primary devices shown in the table above, as well as to reduce shelf effect. In many embodiments, the dilator 102 defines an outer diameter, as shown in the table, and the primary device defines an inner diameter. In order to maximize support of the primary device by the dilator 102, and to minimize the shelf effect created by the gap between the outer diameter and the inner diameter, it may be ideal to reduce the size of the gap. For example, in some embodiments, the outer diameter of the dilator 102 defines a diameter that comprises about 90% of the inner diameter of the primary device. The outer diameter of the dilator 102 may encompass a percentage other than 90% of the inner diameter. For example, the outer diameter may be 85%, 95%, 97%, 99%, etc. of the inner diameter.

In some embodiments, the outer diameter of the dilator 102 is about 95% of the inner diameter of the primary device. In some embodiments, the outer diameter of the dilator 102 is about 91% of the inner diameter of the primary device. In some embodiments, the outer diameter of the dilator 102 is about 92% of the inner diameter of the primary device. In some embodiments, the outer diameter of the dilator 102 is about 93% of the inner diameter of the primary device. In some embodiments, the outer diameter of the dilator 102 is about 94% of the inner diameter of the primary device. In some embodiments, the outer diameter of the dilator 102 is about 96% of the inner diameter of the primary device. In some embodiments, the outer diameter of the dilator 102 is about 97% of the inner diameter of the primary device. In some embodiments, the outer diameter of the dilator 102 is about 98% of the inner diameter of the primary device. In some embodiments, the outer diameter of the dilator 102 is about 99% of the inner diameter of the primary device. In some embodiments, the outer diameter of the dilator 102 is about 99.9% of the inner diameter of the primary device. The inner diameter may be a whole percentage (e.g., 95%) of the outer diameter. In some embodiments, the inner diameter is a tenth of a percentage (e.g., 95.4%) of the outer diameter.

Figure 50A:
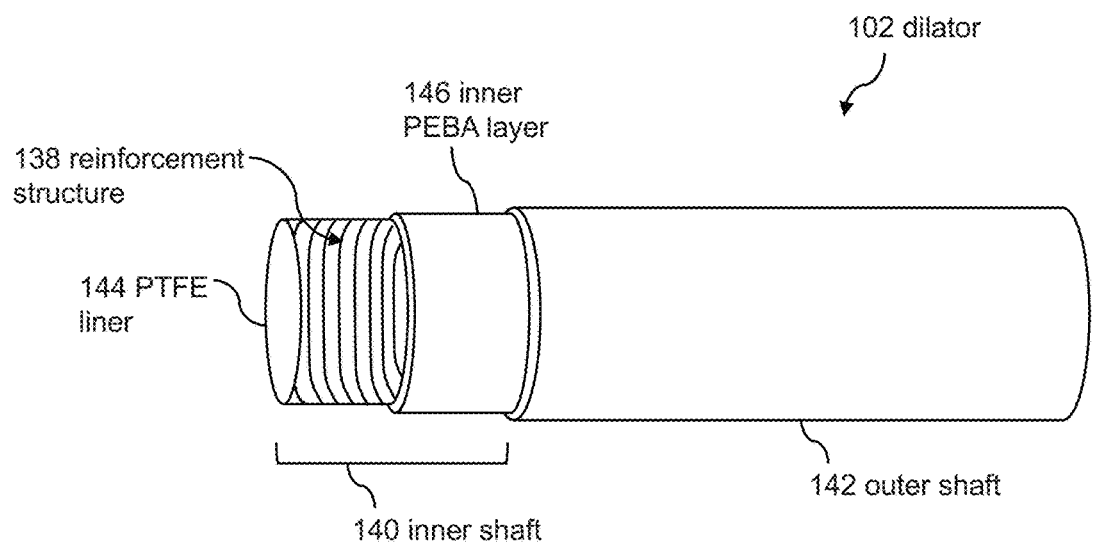
FIGS. 50A and 50B illustrate layers of a dilator of a vasculature navigation system, according to some embodiments.
Figure 50B:
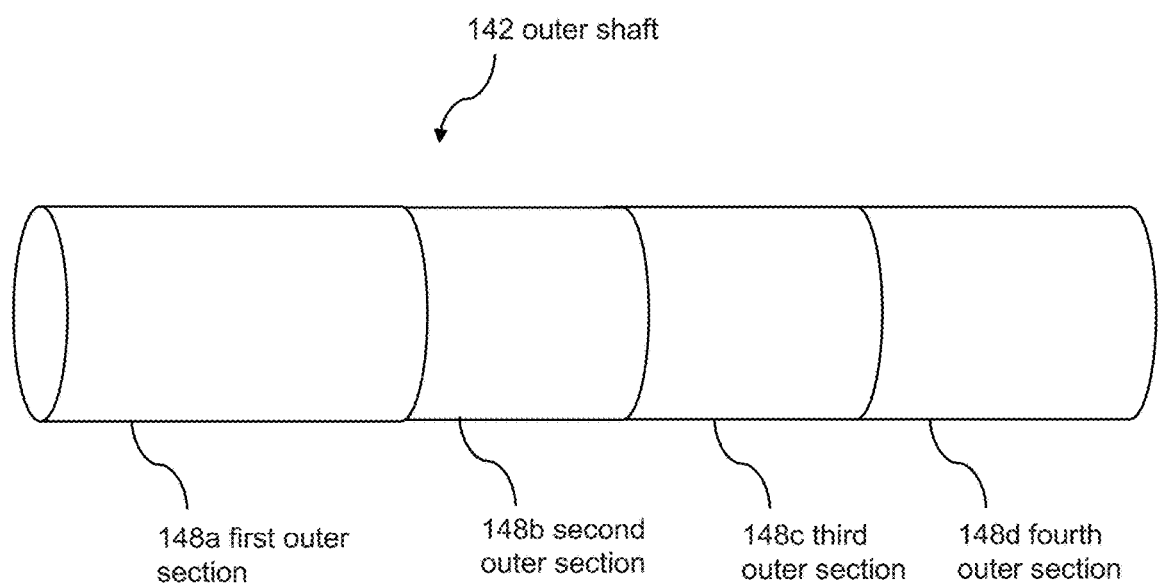

Referring now to FIGS. 50A and 50B, different layers of the dilator 102 are shown. As illustrated in FIG. 50A, in some embodiments, the dilator 102 comprises a coaxial design including an inner shaft 140 and an outer shaft 142. The inner shaft 140 may comprise two layers-a PTFE liner 144 and an inner polyether block amide (PEBA) layer 146.

It should be noted that, though not illustrated in FIG. 50B, both the PTFE liner 144 and the inner PEBA layer 146 may be configured to extend substantially the full length of the dilator 102, within the outer shaft 142. In some embodiments, the PTFE liner 144 contributes lubricity to the dilator 102 to ease loading and/or movement of the guidewire 116 within the dilator 102 by reducing friction between the guidewire 116 and the dilator 102. The inner PEBA layer 146 may be thought of as a "jacket" that covers the PTFE liner 144, adding support and structural integrity to the inner shaft 140 while maintaining an appropriate degree of softness and flexibility. The inner PEBA layer 146 may also increase the kink resistance of the dilator 102. In some embodiments, the outer diameter of the inner shaft 140 is about 0.024-0.025 inches.

As illustrated in FIG. 50A, the dilator 102 may also comprise a reinforcement structure 138 located within a wall of the dilator 102. In some embodiments, the reinforcement structure 138 defines a coil shape and is wound over the PTFE liner 144. The inner PEBA layer 146 and outer shaft 142 may then be coated over the reinforcement structure 138 such that the structure 138 is substantially enclosed within the wall of the dilator 102. The reinforcement structure 138 may not be fully enclosed within the wall, and at least a portion of the structure 138 may be present on an outer diameter of the inner PEBA layer 146 on an inner diameter of the outer shaft 142. In some embodiments, the reinforcement structure 138 is located within substantially an entire length of the dilator 102. The reinforcement structure 138 may terminate at a location proximal to the tapered portion 126, such that the reinforcement structure 138 is not located in a distalmost tip of the dilator 102. In some embodiments, the reinforcement structure 138 comprises a round wire.

FIG. 50B demonstrates that, in some embodiments, the outer shaft 142 comprises a first outer section 148a, a second outer section 148b, a third outer section 148c, and a fourth outer section 148d. Unlike the layers of the inner shaft 140, which comprise true layers where the inner PEBA layer 146 is coated on top of the PTFE liner 144, each of the outer sections 148 may represent a change in material along the length of the outer shaft 142. Stated differently, rather than layering on top of one another, each of the sections 148 may be located adjacent one another. There may be some minimal layering at the transition points between sections 148. The outer shaft 142 may define a substantially consistent outer diameter throughout the proximal portion 110 and the distal portion 112 until just proximal the tapered portion 126. It should be noted that the first outer section 148a may be considered the most proximal section, while the fourth outer section 148d may be considered the most distal section. For the sake of clarity of the drawings, the tapered portion 126 is not included in FIGS. 50A and 50B.

In some embodiments, each of the first, second, and third outer sections 148a, 148b, 148c comprise PEBA material, like the inner PEBA layer 146 of the inner shaft 140. The different sections 148 may be distinguished based on the durometer grade of the PEBA of each section. For example, in some embodiments, the first outer section 148a comprises 72D PEBA, the second outer section 148b comprises 55D PEBA, and the third outer section 148c comprises 35D PEBA. Like the second outer section 148b, the inner PEBA layer 146 may also comprise 55D PEBA. Each of the outer sections may also be distinguished based on length. In some embodiments, the first outer section 148a defines a length of about 140 cm, the second outer section 148b defines a length of about 4 cm, and the third outer section 148c defines a length of about 6 cm. The fourth outer section 148d may define a length of about 8 cm and may comprise a different polymer than PEBA. In some embodiments, the fourth outer section 148d comprises a polyether or polyester-based thermoplastic polyurethane (TPU) blend, such as a NEUSoft™ 62 A TPU blend produced by Avient™. Any number of TPU blends made by different manufacturers may be suitable for creating the dilator 102.

Figure 51:
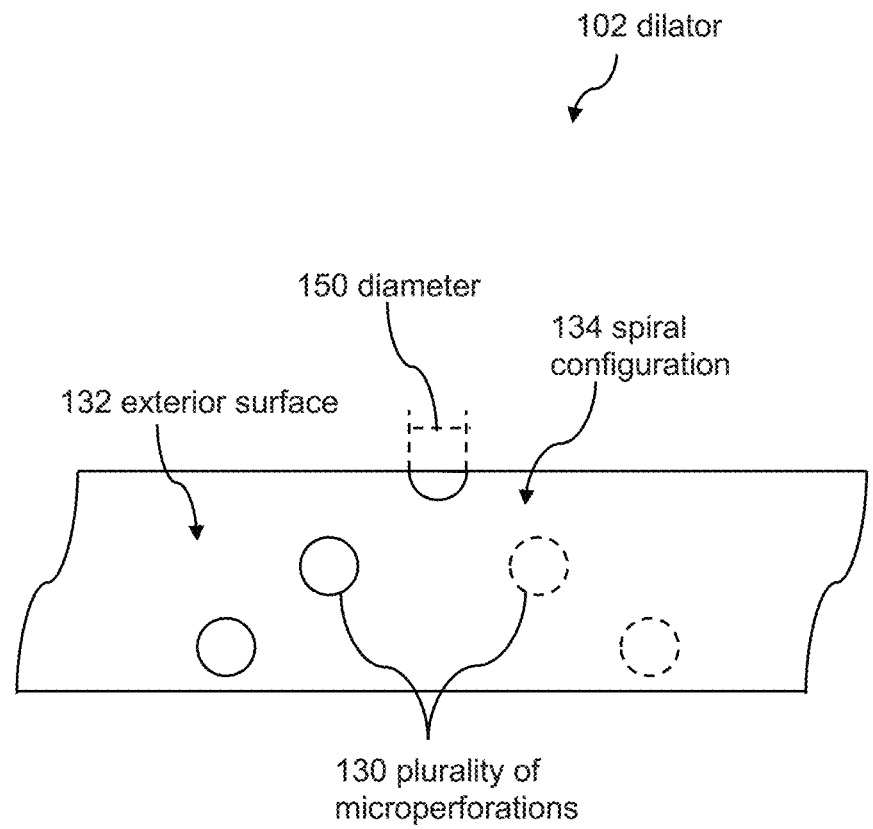
FIG. 51 illustrates a side view of a dilator of a vasculature navigation system including a plurality of microperforations, according to some embodiments.

FIG. 51 illustrates a close-up view of the plurality of microperforations 130 located on the exterior surface 132 of the dilator 102. As shown in both FIGS. 49 and 51, in some embodiments, the plurality of microperforations 130 is arranged in a spiral configuration 134 around 360 degrees of the dilator 102. As previously mentioned, the microperforations shown in dashed lines may be considered to represent microperforations located on the "back" side of the dilator 102. Each microperforation of the plurality of microperforations 130 may be evenly spaced from an adjacent microperforation, and, in some embodiments, the spacing between microperforations is about 1 cm at a 90 degree angle. The spacing may comprise a distance greater than 1 cm. In some embodiments, the microperforations are closer to one another than 1 cm. The even spacing of the plurality of microperforations 130 may contribute to a high degree of symmetry of the dilator 102.

In some embodiments, as shown in FIGS. 49 and 51, the dilator 102 includes a relatively small number of microperforations, especially compared to the plurality of microperforations 40 of the elongated access assist device 12 of the catheter system 10. As illustrated in the Figures, the plurality of microperforations 130 may include five microperforations. In some embodiments, the plurality of microperforations 130 includes two, three, four, six, or more than six microperforations.

Each microperforation of the plurality of microperforations 130 may define a diameter 150. In some embodiments, the diameter 150 is about 0.01 inches. The diameter 150 may be slightly larger, such as 0.012 inches. In some embodiments, the diameter 150 is smaller than 0.01 inches. As a result of creating the plurality of microperforations 130 via laser cutting the wall of the dilator 102, the plurality of microperforations 130 may define a funnel shape, where the diameter on the exterior surface 132 is larger than the diameter on the interior surface of the dilator 102.

It should be noted that though not illustrated with marker bands, the dilator 102 may comprise at least one marker band, similar to the elongated access assist device 12. The marker band(s) of the dilator 102 may be located in a similar and/or the same location as the marker band(s) 44 of the elongated access assist device 12. For example, the tapered portion 126 may include at least one marker band.

Materials

With regard to the materials that comprise the various components of the catheter system 10, a wide array of biocompatible materials may be used. For example, any one of Nylon 12, Copolyester, Polyolefin, Polyurethane, Polyether Block Amide, PTFE, Platinum, Iridium, Tungsten, and a hydrophilic coating may comprise any one or multiple components of the system 10. In addition, any one or multiple components of the system 10 may comprise a combination of the listed materials. A person having ordinary skill in the art of medical devices, particularly neurovascular devices, will understand that materials used in the system 10 may include materials not listed in this disclosure. Materials used may include a combination of any one or multiple listed materials with any one or multiple materials not listed here.

Similar to the materials of the catheter system 10, a wide array of biocompatible materials may also be used to comprise the various components of the vasculature navigation system 100. Similar components between the two systems 10, 100 may be comprised of substantially similar materials. In particular regarding the hydrophilic coating, a proprietary hydrophilic coating blend produced by Biocoat® (of Horsham, Pa., USA) may be used. In some embodiments, the hydrophilic coating is applied via a dip coating process and cured with UV light and/or heat. The hydrophilic coating may define a very thin layer over the outer shaft 142 that does not significantly contribute to the outer diameter of the outer shaft 142. In some embodiments, the Biocoat® formula outperformed hydrophilic coatings from other producers, and was found to be more durable with less flaking and a good lubricity that greatly reduced the coefficient of friction.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

The various features and processes described above may be used independently of one another, or may be combined in various ways. All possible combinations and subcombinations are intended to fall within the scope of this disclosure. In addition, certain methods, events, states, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

The term "substantially" is used to mean "completely" or "nearly completely." For example, the disclosure includes, "The plurality of microperforations may be configured to facilitate a substantially continuous release of fluid." In this context, "substantially continuous" means that the release of fluid may be continuous or nearly continuous. For example, there may be short (e.g., less than one minute) interruption(s) in fluid release during a procedure, and the release of fluid would still be considered "substantially continuous."

The term "about" is used to mean "approximately." For example, in discussing the outer diameter of the elongated access assist device compared to the inner diameter of a primary device, the disclosure includes, "The outer diameter may be about 90% of the inner diameter." In this context, "about 90%" is used to mean "approximately 90%." When discussing diameters, "about" may encompass +/−2% of the stated value. For example, an embodiment where the outer diameter is between 88% and 92% of the inner diameter would fall into the understanding of "about 90%," as used in this disclosure.

The term "spaced" is used to mean "located at a distance from one another." For example, the disclosure includes "the plurality of microperforations are substantially evenly spaced and dispersed across the tapered portion." In this context, "spaced" indicates that each microperforation in the plurality of microperforations is located at a distance from each other microperforation. Additionally, the use of "substantially evenly spaced" indicates that the microperforations are evenly spaced or nearly evenly spaced. An embodiment where the spacing between each microperforation is not exactly equal, but is within a 10% margin of error, would fall into the understanding of "substantially evenly spaced," as used in this disclosure.

The term "dispersed" is used to mean "distributed or spread over a wide area." For example, the disclosure includes, "the plurality of microperforations are substantially evenly spaced and dispersed across the tapered portion." In this context, "dispersed" indicates that the plurality of microperforations are distributed or spread across the tapered portion, as shown in FIGS. 6 and 8-11, as well as 28-33. An embodiment where the plurality of microperforations are located on at least 85% of the tapered portion would fall into the understanding of "dispersed across the tapered portion," as used in this disclosure.

The term "adjacent" is used to mean "next to or adjoining." For example, the disclosure includes, "In many embodiments, the elongated access assist device 12 includes an access port 24 and a flush port 32 located adjacent a proximal end of the elongated access assist device 12." In this context, the access port and flush port may be understood as located next to or adjoining the proximal end of the elongated access assist device, as shown in FIG. 3. For example, the access port may be considered adjoining the proximal end and the flush port may be considered next to the proximal end, but both are adjacent the proximal end.

The disclosure may refer to a "face of the occlusion." In some embodiments, the "face of the occlusion" should be interpreted as the "site of the occlusion." The "face of the occlusion" may also be used to refer simply to "the occlusion."

The disclosure may refer to both an elongated access assist device and a vascular navigation system. It should be appreciated that a vascular navigation system may include an elongated access assist device. In some embodiments, the terms are used interchangeably. The disclosure may include embodiments whereby the elongated access assist device is specifically used in neurovascular treatment. Also, the disclosure may include embodiments whereby the vascular navigation system is specifically used in neurovascular treatment. Additionally, the disclosure may include embodiments whereby the elongated access assist device is used in non-neurovascular treatments, e.g., cardiothoracic treatments, abdominal treatments, and treatments of a patient's extremities. Moreover, the disclosure may include embodiments whereby the vascular navigation system is used in non-neurovascular treatments, e.g., cardiothoracic treatments, abdominal treatments, and treatments of a patient's extremities.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

What is claimed is:

1. A vasculature navigation system, comprising:
    a dilator having a proximal end and a distal end located opposite the proximal end, the dilator comprising a guidewire lumen extending between the proximal end and the distal end, the dilator defining a proximal portion and a distal portion located opposite the proximal portion;
    an access port located at the proximal end of the dilator, the access port configured to receive a guidewire;
    a distal port located at the distal end of the dilator, the distal port configured to further receive the guidewire;
    a hemostasis valve coupled to the proximal portion of the dilator, the hemostasis valve configured to control fluid flow between the proximal portion and the distal portion;
    a flush port coupled to the proximal portion of the dilator and located distal to the hemostasis valve;
    a tapered portion defining at least part of the distal portion of the dilator, wherein an outer surface of the tapered portion tapers downward toward the distal end;
    a plurality of microperforations coupled only to an exterior surface of the proximal portion of the dilator; and
    a hydrophilic coating located only on the tapered portion of the dilator, wherein the plurality of microperforations and the hydrophilic coating enable navigation of the dilator through the patient's vasculature by reducing friction between the dilator and the patient's vasculature.

2. The vasculature navigation system of claim 1, wherein each microperforation of the plurality of microperforations defines a diameter of about 0.01 inches on the exterior surface of the dilator.

3. The vasculature navigation system of claim 1, wherein each microperforation of the plurality of microperforations defines an aperture.

4. The vasculature navigation system of claim 1, further comprising:
    a fluid supply source coupled to the flush port; and
    a fluid located within the fluid supply source and configured to flow from the fluid supply source through the flush port into the dilator,
    wherein the fluid supply source is pressurized to an extent sufficient to enable propulsion of the dilator upon release of the fluid via the plurality of microperforations.

5. The vasculature navigation system of claim 4, wherein the plurality of microperforations are configured to release a substantially continuous flow of fluid from the fluid supply source.

6. The vasculature navigation system of claim 4, wherein the fluid is pressurized within the dilator to the extent sufficient to enable propulsion of the dilator as the fluid is released from the plurality of microperforations.

7. The vasculature navigation system of claim 4, wherein the fluid supply source comprises a supply of saline.

8. The vasculature navigation system of claim 4, wherein the plurality of microperforations is located proximal the hydrophilic coating, and wherein the fluid released from the plurality of microperforations is configured to flow over the hydrophilic coating.

9. The vasculature navigation system of claim 1, wherein the plurality of microperforations is arranged in a spiral configuration around the exterior surface of the dilator.

10. The vasculature navigation system of claim 9, wherein each microperforation of the plurality of microperforations is evenly spaced from an adjacent microperforation.

11. The vasculature navigation system of claim 10, wherein the plurality of microperforations is coupled to the proximal portion of the dilator.

12. The vasculature navigation system of claim 1, wherein the dilator comprises a reinforcement structure located within a wall of the dilator, the reinforcement structure defining a coil shape.

13. The vasculature navigation system of claim 12, wherein the reinforcement structure is located within substantially an entire length of the dilator.

14. The vasculature navigation system of claim 13, wherein the reinforcement structure comprises a round wire.

15. The vasculature navigation system of claim 1, wherein the dilator is configured to be received by a primary device such that at least the tapered portion of the dilator extends distal a distal end of the primary device, and wherein the dilator comprises a hydrophilic coating configured to reduce friction between the dilator and the primary device.

16. The vasculature navigation system of claim 15, wherein the primary device comprises one of a guide catheter, an aspiration catheter, a sheath, and a delivery catheter.

17. The vasculature navigation system of claim 15, wherein the dilator defines an outer diameter and the primary device defines an inner diameter, wherein the outer diameter of the dilator is about 90% of the inner diameter of the primary device.

18. The vasculature navigation system of claim 1, wherein the hydrophilic coating is located on a portion of the distal portion of the dilator, the portion defining a length of twenty centimeters.

19. The vasculature navigation system of claim 1, wherein the tapered portion defines a conical shape.

20. The vasculature navigation system of claim 1, wherein the distal end comprises a rounded end.

\* \* \* \* \*